United States Patent
Uematsu et al.

(10) Patent No.: US 8,105,312 B2
(45) Date of Patent: Jan. 31, 2012

(54) SYRINGE WITH CONNECTOR, CONNECTOR FOR SYRINGE, AND SYRINGE

(75) Inventors: Raita Uematsu, Higashihiroshima (JP); Takehiko Yuki, Hiroshima (JP); Naotsugu Ito, Hiroshima (JP); Ryoji Fujii, Hiroshima (JP); Tadashi Okiyama, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 240 days.

(21) Appl. No.: 11/547,055

(22) PCT Filed: Feb. 7, 2005

(86) PCT No.: PCT/JP2005/001778
§ 371 (c)(1),
(2), (4) Date: Oct. 2, 2006

(87) PCT Pub. No.: WO2005/099791
PCT Pub. Date: Oct. 27, 2005

(65) Prior Publication Data
US 2007/0265577 A1  Nov. 15, 2007

(30) Foreign Application Priority Data

| | | |
|---|---|---|
| Apr. 7, 2004 | (JP) | 2004-113596 |
| Apr. 7, 2004 | (JP) | 2004-113597 |
| Apr. 7, 2004 | (JP) | 2004-113598 |
| Apr. 7, 2004 | (JP) | 2004-113600 |
| Apr. 7, 2004 | (JP) | 2004-113601 |
| Apr. 7, 2004 | (JP) | 2004-113602 |

(51) Int. Cl.
*A61M 39/00* (2006.01)

(52) U.S. Cl. .......... 604/533; 604/534; 604/535
(58) Field of Classification Search .......... 604/200, 604/284, 600, 507, 533, 187, 111, 85–87; 411/122, 167
See application file for complete search history.

(56) References Cited

U.S. PATENT DOCUMENTS

| | | | |
|---|---|---|---|
| 2,490,728 A * | 12/1949 | Cox | 411/277 |
| 3,052,241 A | 9/1962 | Myerson et al. | |
| 4,405,312 A * | 9/1983 | Gross et al. | 604/29 |
| 4,596,571 A | 6/1986 | Bellotti et al. | |

(Continued)

FOREIGN PATENT DOCUMENTS

JP  4-83255  7/1992

(Continued)

*Primary Examiner* — Jackie Ho
*Assistant Examiner* — Imani Hayman
(74) *Attorney, Agent, or Firm* — Wenderoth, Lind & Ponack, L.L.P.

(57) ABSTRACT

The present invention aims at offering: a syringe connectable to a port in a fixed manner as well as capable of demonstrating high operational performance even in the case of direct connection where a connector is not used; a connector used for the syringe; and a syringe able to attach the connector thereto. For the attainment of the above objectives, the medical syringe of the present invention is a medical syringe including a cyrindrical connection supporting member which enhances the holding force of a luer part inserted into a port when the medical syringe is connected to the port. The connection supporting member is set by sliding along the luer or a syringe body in a state of being movable between a first position near a tip of the luer and a second position away from the tip of the luer. The medical syringe is characterized in that, when the connection supporting member is moved to the second position, the tip of the luer part is exposed.

11 Claims, 43 Drawing Sheets

U.S. PATENT DOCUMENTS

| | | | |
|---|---|---|---|
| 4,995,871 A * | 2/1991 | Sasaki et al. | 604/110 |
| 5,100,394 A | 3/1992 | Dudar et al. | |
| 5,135,489 A | 8/1992 | Jepson et al. | |
| 5,158,554 A | 10/1992 | Jepson et al. | |
| 5,167,648 A | 12/1992 | Jepson et al. | |
| 5,171,234 A | 12/1992 | Jepson et al. | |
| 5,188,620 A | 2/1993 | Jepson et al. | |
| 5,211,638 A | 5/1993 | Dudar et al. | |
| 5,411,499 A | 5/1995 | Dudar et al. | |
| 5,658,260 A | 8/1997 | Desecki et al. | |
| 5,776,125 A | 7/1998 | Dudar et al. | |
| 5,797,897 A | 8/1998 | Jepson et al. | |
| 5,871,500 A | 2/1999 | Jepson et al. | |
| 5,899,888 A | 5/1999 | Jepson et al. | |
| 5,964,785 A | 10/1999 | Desecki et al. | |
| 6,048,337 A * | 4/2000 | Svedman | 604/313 |
| 6,164,044 A | 12/2000 | Porfano et al. | |
| 6,189,292 B1 | 2/2001 | Odell et al. | |
| 6,193,697 B1 | 2/2001 | Jepson et al. | |
| 6,210,372 B1 * | 4/2001 | Tessmann et al. | 604/181 |
| 6,213,996 B1 | 4/2001 | Jepson et al. | |
| 6,217,568 B1 | 4/2001 | Jepson et al. | |
| 6,250,052 B1 | 6/2001 | Porfano et al. | |
| 6,261,266 B1 | 7/2001 | Jepson et al. | |
| 6,263,641 B1 | 7/2001 | Odell et al. | |
| 6,306,118 B1 | 10/2001 | Crawford et al. | |
| 6,447,498 B1 | 9/2002 | Jepson et al. | |
| 6,605,076 B1 | 8/2003 | Jepson et al. | |
| 6,792,743 B2 | 9/2004 | Odell et al. | |
| 2001/0047154 A1 | 11/2001 | Jepson et al. | |
| 2002/0069616 A1 | 6/2002 | Odell et al. | |
| 2002/0147429 A1 * | 10/2002 | Cowan et al. | 604/187 |
| 2007/0079894 A1 * | 4/2007 | Kraus et al. | 141/319 |

FOREIGN PATENT DOCUMENTS

| | | |
|---|---|---|
| JP | 6-66641 | 3/1994 |
| JP | 7-110284 | 11/1995 |
| JP | 11-318869 | 11/1999 |
| JP | 2002-505980 | 2/2002 |
| JP | 2003-024454 | 1/2003 |
| JP | 3456241 | 10/2003 |

* cited by examiner

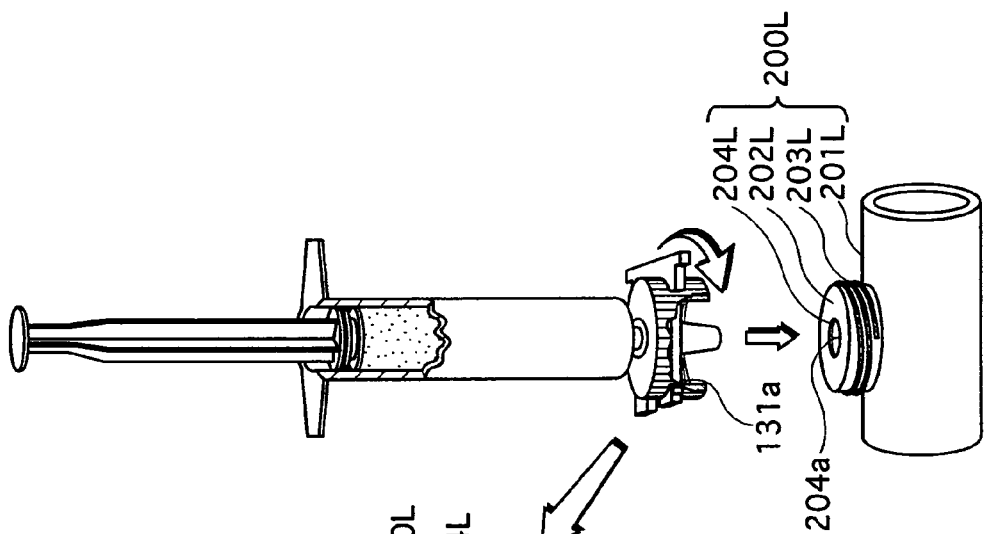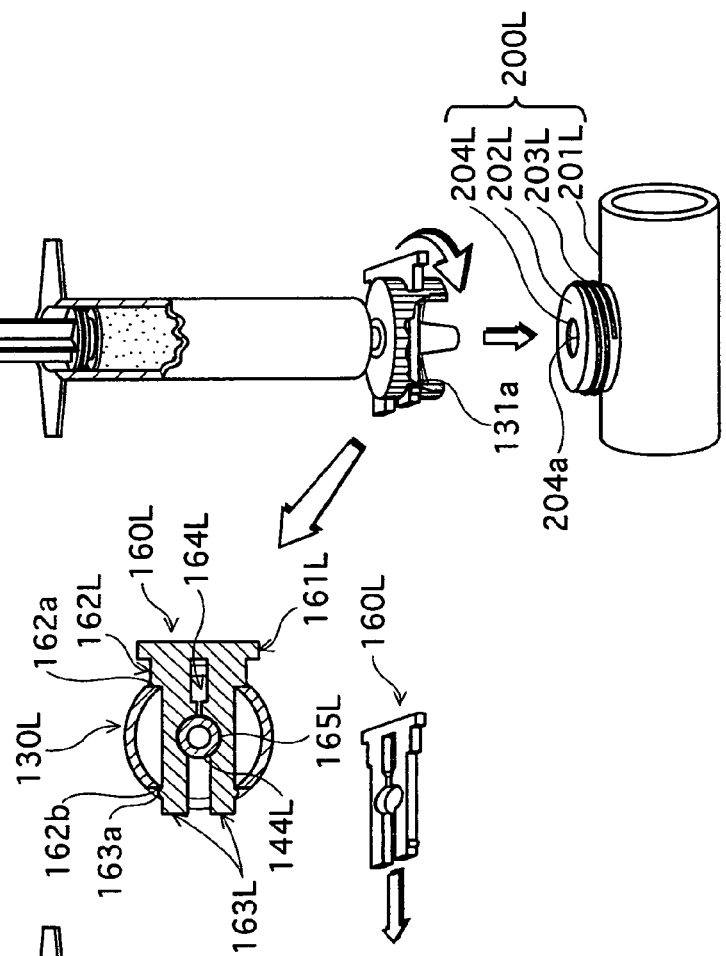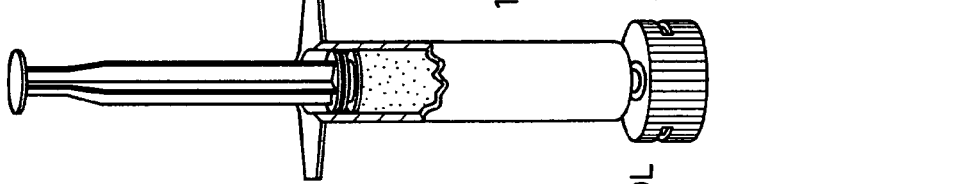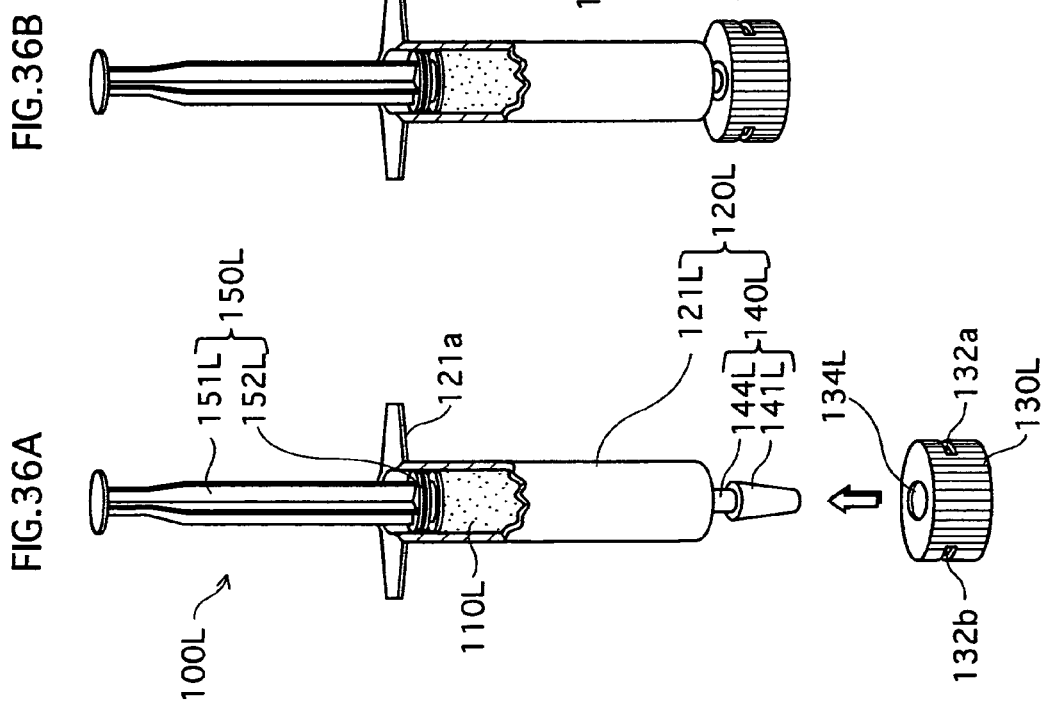

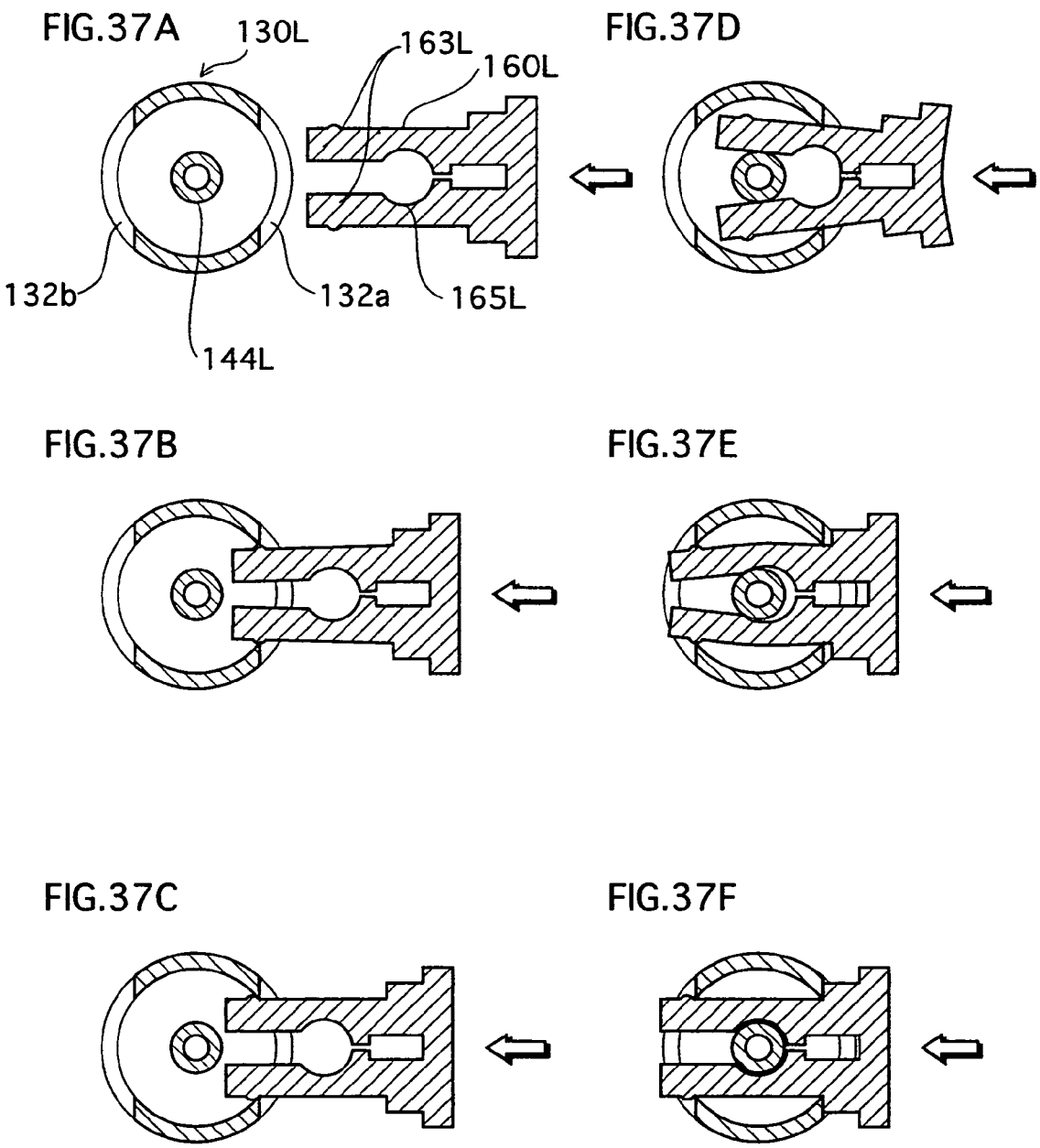

SYRINGE WITH CONNECTOR, CONNECTOR FOR SYRINGE, AND SYRINGE

TECHNICAL FIELD

The present invention relates to a connector-attached syringe, a connector used for a syringe and a syringe.

BACKGROUND

In the medical field, syringes (i.e., medical instruments for injection) are used in a variety of different ways.

For example, in a typical syringe, a female taper connector, such as a needle hub having a needle tube, is generally attached to a luer part located at the tip of syringes, and such syringes are used to draw blood from patients and to inject medication held in the syringes to patients.

In addition, syringes may be used in a system referred to as a pipeline system, such as a transfusion line system and a blood collection line system. In the pipeline system, a syringe is connected to an external port of the line system, and then medication in the syringe is applied therefrom, or reversely fluid is drawn from the line. To connect a syringe to such a line system, a direct connection method (also known as luer slip) and a fixed connection method are used. In the direct connection method, the luer part is inserted directly into the port of the line system. In the fixed connection method, a luer part 1141L of a syringe 1000L is connected to a port 1200L by screwing them together using a connector (lockout) 1130L, as shown in FIGS. 41A to 41C.

Prefilled syringes are also used in medical practices. Prefilled syringes are syringes containing prefilled medication in the syringe body. In this case, the nozzle tip of the syringe body is sealed by resin, for example, and the tip is opened before use and a plunger is inserted into the opening to thereby discharge the medication. Such prefilled syringes facilitate a rapid procedure by reducing the trouble and time required for administration of medication to patients and medication mixing.

As to syringes connectable to the port of the above-mentioned line system in a fixed manner (referred to as luer-lock syringes), it is often the case that a locknut is already attached to the luer part. A stepped portion, whose diameter is different from that of the rest of the luer part, is provided in the luer part. The luer part is preliminarily inserted into the locknut, which is kept in place by the stepped portion. This structure is adopted in order to reliably connect the syringe and the line system and enable a quick connection operation.

However, such a connector-attached syringe has a problem that the luer part cannot be connected to the direct connection port since the locknut is in the way, as shown in FIG. 42.

Another problem is that, when attempting to attach a needle hub to the connector-attached syringe at the luer part, the user cannot see the right positional relationship between the luer part and the needle hub since the lock nut is in the way, as shown in FIG. 43, and cannot connect the luer part and needle hub successfully. In addition, since the lockout is set on the luer part, the length of a portion of the luer part exposing outside is insufficient, which leads to a problem of not being able to make the needle hub adequately hold onto the luer part.

Thus, immediate improvement is desired in the versatility of lockout-attached syringes due to the requirements for speedy and accurate responses in medical field.

SUMMARY

One Embodiment of the present invention includes: a syringe connectable to a port in a fixed manner as well as capable of demonstrating high operational performance even in the case of direct connection where a connector is not used; a connector used for the syringe; and a syringe able to attach the connector thereto.

In order to solve the above problems, one embodiment of the present invention is a connector-attached syringe having a connector for connecting a syringe unit to a port. The connector is disposed at a luer part in the syringe unit which includes a syringe body and a plunger. Here, the luer part includes an engaging portion for engaging with the connector. The connector includes a first opening for engaging with the engaging portion in the syringe axial direction and a second opening larger than the first opening and allowing for the luer part to be freely insertable and removable thereto and from in the syringe axial direction. The first and second openings communicate with each other. In some embodiments, the first and second openings may communicate with each other via a passage.

Further more, in the present invention, the engaging portion may be a step positioned between a tip and a base of the luer part.

First, according to such structures of the present invention, the luer part is inserted into the second opening (insertion hole) of the connector, and than slid into the first opening (engaging hole) so that the base side of the luer part next to the engaging portion is fitted into the engaging hole of the connector, and whereby the connector is attached to the syringe while these two are engaged with each other. Thus, the user is able to attach the connector to the syringe and connect the syringe, using the connector, to a fixed connection port of a transfusion line system or the like.

Second, in one embodiment, the connector can be readily detached from the luer part engaged with the engaging hole of the connector by relatively moving the luer part to the insertion hole.

Thus, the connector can be detached from the luer part so as not to be in the way when the luer part is connected to the direct connection port. As a result, the luer part can be reliably connected to a direct connection port of a transfusion line system or the like where a connector is not used. Thus, the syringe of the present invention exhibits high versatility.

A prefilled syringe having a conventional structure has problems regarding operational performance such as the connector obstructing the view of the user, thus making it difficult to determine the positioning of the luer part and the needle hab. Additionally, the needle hub cannot be deeply placed in and attached to the luer part due to the presence of the connector. However, the present invention is able to fundamentally solve these conventional problems since the connector is readily detachable from the connector.

Additionally, in one embodiment, the passage is provided between the first and second openings so that these openings communicate with each other. Herewith, the luer part is forcedly shifted through the passage and moved to the engaging hole to be thereby reliably fitted when the syringe is used.

To solve the above problems, one embodiment of the present invention is also a connector-attached syringe having a connector for connecting a syringe unit to a port. The connector is disposed at a luer part in the syringe unit which includes a syringe body and a plunger. Here, a first engaging portion for engaging with a second engaging portion on the connector is disposed on the outer peripheral surface of the syringe body. When an external force is applied, according to a predetermined operation, to one of the connector and the syringe unit in a direction different from a syringe axial direction, the engagement of the first and second engaging portions is released.

Here, the first engaging portion may be, on the outer peripheral surface of the body of the syringe, a tip portion of the luer part, which has a larger diameter than the remaining portion (a stepped region in which a convex and a concave portions are provided side by side).

Specifically, a body of the connector may be tubular, and the second engaging portion may be on an extension portion which extends from the body of the connector. Here, the first and second engaging portions are engaged with each other by inserting the luer part into the body of the connector and elastically contacting the extension portion with the outer peripheral surface of the syringe body. The engagement is released when the second engaging portion is detached from the outer peripheral surface by performing the predetermined operation on one of the connector and the syringe unit.

First, according to such a structure of the present invention, the connector can be attached to the syringe while these two are engaged with each other by inserting the luer part into the connector and engaging the second engaging portion of the connector with the first engaging portion of the body of the syringe. Thus, the user is able to engage the connector with the syringe and connect the syringe, using the connector, to a fixed connection port of a transfusion line system or the like.

Second, in one embodiment of the present invention, an external force is applied to the connector in a direction different from the syringe axial direction (e.g. in the syringe radial direction) according to a predetermined operation to detach the second engaging portion of the connector provided, for example, on the extention portion from the first engaging portion on the syringe. Herewith, the first and second engaging portions are disengaged, and whereby the connector can be readily detached from the luer part.

Thus, the connector can be detached from the luer part so as not to be in the way when the luer part is connected to the direct connection port. As a result, the luer part can be reliably connected to a direct connection port of a transfusion line system or the like where a connector is not used. Thus, the syringe of the present invention exhibits high versatility.

A prefilled syringe having a conventional structure has problems regarding operational performance such as that the connector obstructs the view of the user and makes it difficult to determine the positioning of the luer part and the needle halo and that the needle hub cannot be deeply placed in and attached to the luer part due to the presence of the connector. However, embodiments of the present invention are able to fundamentally solve these conventional problems since the connector is readily detached from the connector.

To solve the above problems, embodiments of the present invention are also a connector-attached syringe having a connector attached to a luer part jutting out from a syringe unit which includes a syringe body and a plunger. The connector is used for fixedly holding the syringe unit on a port. Here the luer part includes an engaging portion for engaging with the connector. The connector includes a tubular body portion with a base and a constraint portion encircling a periphery of the body portion and exerting constraint effects on the base by shifting in the axial direction of the body portion. The base includes a plurality of swingable petal-shaped members. In a first state where the petal-shaped members are closed due to the constraint effects exerted on the base, the engaging portion is engaged with the petal-shaped members in the axial direction. In a second state where the petal-shaped members are open due to the base being free from the constraint effects, the luer part is freely insertable and removable into and from the connector in the axial direction via an open hole formed in a substantially central region of the base when the petal-shaped members are open.

As to embodiments of the present invention, the constraint portion may be a nut having a screw on an internal peripheral surface thereof. Here, the body portion is in the shape of a substantial cylinder, and has a screw, which corresponds to the nut, on a section of the outer peripheral surface of the cylinder. The section is a range where the constraint portion is movable. In the first state, part of the body portion corresponding to the section is closed, taking on a shape of a cylinder. In the second state, the part of the body portion is open, spreading like open tweezers towards the base in the axial direction.

Here, in the connector-attached syringe, the luer part may have, on the base side thereof, a reduced-diameter section, and the engaging portion may be a step created by the reduced-diameter section.

Furthermore, one embodiment of the present invention is a connector for fixedly holding a syringe unit on a port and being disposed at a luer part jutting out from the syringe unit which includes a syringe body and a plunger. The connector comprises: a tubular body portion with a base; and a constraint portion encircling a periphery of the body portion and exerting constraint effects an the base by shifting in the axial direction of the body portion. Here, the base of the body portion includes a plurality of swingable petal-shaped members. In a first state where the petal-shaped members are closed due to the constraint effects exerted on the base, the luer part is engaged with the petal-shaped members in the syringe axial direction. In a second state where the petal-shaped members are open due to the base being free from the constraint effects, the luer part is freely insertable and removable into and from the connector via an open hole formed in a substantially central region of the base when the petal-shaped members are open.

In the connector above, the constraint portion may be a nut having a screw on an internal peripheral surface thereof. Here, the body portion is in the shape of a substantial cylinder, and has a screw, which corresponds to the nut, on a section of the outer peripheral surface of the cylinder. The section is a range where the constraint portion is movable. In the first state, part of the body portion corresponding to the section is closed, taking on a shape of a cylinder, and in the second state, the part of the body portion is open, spreading like open tweezers towards the base in the axial direction.

One embodiment of the present invention is also a procedure method for treatment and diagnosis using the connector-attached syringe Above.

With the connector-attached syringe of embodiments of the present invention, the connector can readily change the state between the first and the second states. Accordingly, the connector-attached syringe is capable of engaging the luer part of the syringe with the petal-shaped members of the base as well as making the luer part freely insertable and removable via the open hole on the base. That is, the connector-attached syringe allows for a selective use of the syringe between the luer-lock type and the luer-slip type according to the connection style of a port on which the syringe is to be fixedly held.

As to the connector-attached syringe of embodiments of the present invention, the connector can be thus freely attached and detached according to the connection style of the port, and the detached connector can be used with another syringe. This results in a reduction in the cost burden on the user but does not cause a decrease in work performance when the syringe is used. In addition, the connector-attached syringe of the present invention can be connected to a port in either the luer-slip style or the luer-lock style, having high versatility for connection with a port.

Since having the same structure as the connector attached to the luer part in the connector-attached syringe above, the connector of one embodiment of the present invention also has similar advantageous effects as described above.

Therefore, the connector in one embodiment of the present invention is effective to enhance the versatility of the syringe when it is fixedly held on a port.

Furthermore, one embodiment of the present invention is a connector-attached syringe having a connector attached to a luer part jutting out from a syringe unit which includes a syringe body and a plunger. The connector is used for fixedly hold the syringe unit on a port. Here, the luer part includes an engaging portion for engaging with the connector. The connector includes a plurality of components, which individually have interlocking members for coupling mechanisms. The interlocking members are interlocked with each other to thereby couple the components and make the connector in the shape of a tube having a base. When made in the shape of the tube, the connector engages with the engaging portion of the luer part. When the coupling of the components is released, the luer part is freely insertable and removable into and from the connector.

As to the present invention, in the above-mentioned connector-attached syringe, the components may be symmetrical to each other and have end portions facing to each other. Here, a cutout is disposed on each of the end portions. The cutouts face to each other to form an engaging hole, which engages with the engaging portion of the luer part.

As to the present invention, in the above-mentioned connector-attached syringe, at least one of the coupling mechanisms may include a locking tab and a locked tab which interlock with each other when the components are coupled.

As to the present invention, in one of the above-mentioned connector-attached syringes, the luer part may have, on a base side thereof, a reduced-diameter section, and the engaging portion may be a step created by the reduced-diameter section.

Furthermore, one embodiment of the present invention has a connector for fixedly holding a syringe unit on a port and being disposed at a luer part jutting out from the syringe unit which includes a syringe body and a plunger. The connector comprises: a plurality of components, which individually have interlocking members for coupling mechanisms. The interlocking members interlock with each other to thereby couple the components and make the connector in the shape of a tube having a base. Here, when made in the shape of the tube the connector engages with the luer part. When the coupling of the components is released, the luer part is freely insertable and removable into and from the connector.

As to the present invention, in the above-mentioned connector, the components may be symmetrical to each other and have end portions facing to each other. Here, a cutout is disposed on each of the end portions, and the cutouts face to each other to form an engaging hole, which engages with an engaging portion of the luer part.

As to the present invention, in the above-mentioned connector, at least one of the coupling mechanisms may include a locking tab and a locked tab which interlock with each other when the components are coupled.

Furthermore, one embodiment of the present invention is a procedure method for treatment and diagnosis using the connector-attached syringe above.

The connector-attached syringe of this embodiment of the present invention has a structure in which the connector is freely attachable and detachable to and from the luer part of the syringe simply by changing the state of the connector between the state where the multiple components are coupled to form the tulle with a base and the state where the coupling is released. Accordingly, the connector-attached syringe allows for a selective use of the syringe between the luer-lock type and the luer-slip type according to the connection style of a port on which the syringe is to be fixedly held.

Additionally, with the connector-attached syringe, the connector may be detached from the syringe after used or when not used, and then the detached connector may be used with another syringe.

Herewith, the connector-attached syringe of the present invention reduces the cost burden an the user but does not cause a decrease in work performance when the syringe is used. In addition, the connector-attached syringe of the present invention can be connected to a port in either the luer-slip style or the luer-lock style, exhibiting high versatility for connection with a port.

Similarly to the connector attached to the connector-attached syringe above, the connector of the present invention can be easily attached and detached to and from the luer part of the syringe simply by Changing the state of the connector between the state where the multiple components are coupled to form the tube with a base and the state where the coupling is released. Herewith, the connector can be attachable and detachable according to need for example, the connector is engaged with the luer part of the syringe when the syringe and port are connected in the luer-lock style, and the connector is disengaged when they are connected in the luer-slip style.

As a result, the connector of the present invention is effective to enhance the versatility of the syringe for connection with a port.

In order to solve the above problems, in one embodiment of the present invention is a connector-attached medical syringe having a tubular connection supporting member and a pin for increasing, when a syringe unit including a syringe body and a plunger is connected to a port, a connecting force between a luer part of the syringe unit and the port. The luer part is inserted into the port. Here, the connection supporting member includes a first insertion hole disposed on the outer peripheral surface thereof and a second insertion hole disposed on an end portion thereof. The first insertion hole is for the pin to be inserted thereto. The pin includes a fit portion for being fitted with the luer part. The syringe unit freely changes a state thereof between (i) a connector hold state, in which, when the luer part is inserted into the second insertion hole, the pin is inserted into the first insertion hole along an insertion path until the fit portion is fitted with the luer part and (ii) a connector release state, in which the fitting of the fit portion and the luer part is released by pulling the pin out from the first insertion hole.

The syringe of the present invention may be a connector-attached medical syringe having a tubular connection supporting member and a pin for increasing, when a syringe unit including a syringe body and a plunger is connected to a port, a connecting force between a luer part of the syringe unit and the port. The luer part is inserted into the port. Here, the connection supporting member includes a first insertion hole disposed on the outer peripheral surface thereof and a second insertion hole disposed on an end portion thereof. The first insertion hole is for the pin to be inserted thereto. The pin includes a fit portion for being fitted with the luer part. The syringe unit freely changes a state thereof between (i) a connector hold state, in which, when the luer part is inserted into the second insertion hole, the pin is inserted into the first insertion hole along an insertion path until the fit portion is fitted with the luer part and (ii) a connector release state, in which the fitting of the fit portion and the luer part is released by pulling the pin out from the first insertion hole.

Herewith, the syringe can be used as a so-called luer-slip syringe by pulling out the pin and thereby disengaging the connector from the syringe. In addition, the syringe can be used also as a so-called luer-lock syringe by inserting the pin into the connector and thereby engaging the luer part and the connector.

That is, since the syringe functions as either type, its versatility increases.

In addition, the luer part may be in the shape of a substantially cylinder locally having a reduced-diameter section in vicinity of a central region or a base portion thereof. Here, the insertion path of the pin is a line connecting facing sections on the outer peripheral surface and passing in vicinity of the central axis of the connection supporting member. The fitting is made when the fit portion is fitted with the reduced-diameter section of the luer part in the vicinity of the central axis.

According to the structure, the central axis of the luer part coincides with or come close to that of the connector.

As to a connection-target instrument in the luer-lock style, an insertion point for the luer part is generally located in the middle of an engaging structure such as a threaded portion or a groove portion for engagement. Therefore, since the central axes of the luer part and connector substantially coincide, the insertion of the luer part into the port can be performed while the pin is being fitted with the luer part.

In addition, the fitting may be made so that the pin is freely rotatable around the central axis of the reduced-diameter section.

Accordingly, the syringe and the connection-target instrument in the luer-lock style can be connected and fixed to each other simply by rotating the connector without rotating the syringe itself.

In addition, the pin may include a handle portion to be grasped in a case of insertion and pullout. This facilitates easy insertion and pullout of the pin.

BRIEF DESCRIPTION OF THE DRAWINGS

FIG. 36 illustrates usage of a syringe according to Embodiment 17;

FIG. 37 shows the way of a coupling pin being inserted into a lock part according to Embodiment 17;

DETAILED DESCRIPTION

The following sequentially describes Embodiments 1 through 19 of medical syringes of the present invention with the aid of drawings.

1. Embodiment 1

1-1. Overall Structure of Prefilled Syringe

Figure 1:
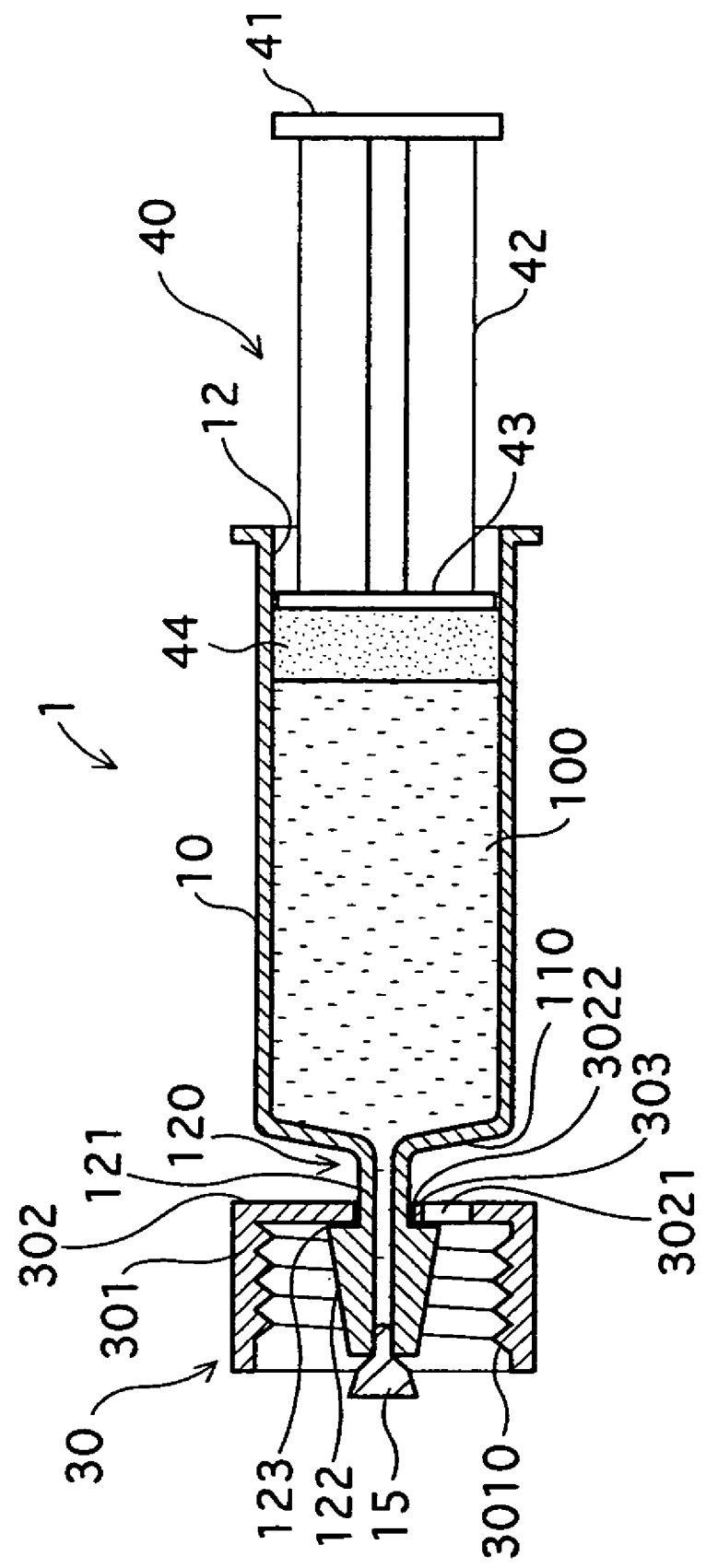
FIG. 1 is a cross sectional view showing a structure of a prefilled syringe of Embodiment 1.

FIG. 1 is a cross sectional diagram showing structures of a prefilled syringe and a connector (a locknut) according to Embodiment 1. Note that, here, a structure is adopted in which a prefilled syringe and a locknut are combined, however, the present invention may be applied to syringes other than prefilled syringes. For convenience of explanation, a plunger 40 is shown here in normal lateral view rather than in cross section.

As shown in FIG. 1, a prefilled syringe 1 may comprise a syringe body 10, the plunger (also referred to as a piston) 40 and the like.

In this embodiment, the syringe body 10 is a tubular body formed by injection molding a material with high chemical resistance, such as polyethylene, polypropylene, polycarbonate or polyvinyl chloride. The tip end of the syringe body 10 is sealed by a top face portion 110, and a luer part 120 juts or extends out from the center of the top face portion 110.

On the other hand, an opening 12 may be formed at the posterior end of the syringe body 10. Although the luer part 120 is formed by drawing to basically give a tapered shape, a stepped portion 123 is provided in a part of the tapered shape, which thereby forms a luer base portion 121 having a smaller diameter and a luer tip portion 122 located on the tip side of the luer part 120 having a larger diameter.

A lockout 30, to be hereinafter described, may be fitted to the stepped portion 123. In addition, the luer tip portion 122 may be formed in a tapered shape in compliance with ISO6/100 so that the regular needle hub 20 can be attached easily. In FIG. 1, a cap 20 is attached to the tip of the luer part 120.

In the following description, the longitudinal direction of the syringe body 10 is referred to as an "axial direction" while a direction perpendicular to the axial direction is referred to as a "radial direction".

The plunger 40 can be made of a resin material with high chemical resistance, similarly to the syringe body 10, and includes a plunger body 42 having a cruciform cross sectional shape for the purpose of reinforcement, at each end of which are formed disk-shaped end pieces having main surfaces in the radial direction. One of the end pieces is a pressing end portion 41 to be pressed by the user with a thumb, and the other end piece is a head portion 43 that is inserted inside the syringe body 10 in the axial direction.

A packing 44 is provided at the tip of the head portion 43 in a manner to make tight contact with the internal wall of the syringe body 10. Here, medication 100 is held in the syringe body 10, which is internally sealed by the packing 44 and the cap 20.

When using the prefilled syringe 1 having such a structure, the user removes the cap 20 to enable discharge of the medication 100. As the user pushes the pressing end portion 41 of the plunger 40 into the syringe body 10 with a thumb, the medication 100 is discharged from the tip of the luer part 120 according to the depressed amount of the plunger 40.

1-2. Structure of Lockout

The prefilled syringe 1 of Embodiment 1 includes the locknut 30, which is a connector easily detachable from the luer part 120, and which is attached so as to engage, in the axial direction, with the stepped portion 123 of the luer part 120. The locknut 30 is used in the medical field as a connection implement for connecting the prefilled syringe 10 to a fixed connection port of a transfusion line system or blood collection line system.

The locknut 30 has a cylindrical form with a bottom, being formed by injection molding a resin material with high mechanical strength. A screw thread is cut on the internal surface of a lateral side portion 301, which corresponds to the cylindrical part of the locknut 30, to thereby form a female screw 3010 in compliance with, for example, ISO594-2. The female screw 3010 may engage with a male screw 5010 to be hereinafter described.

A snowman-shaped hole 3020 formed by perforating two holes communicating with each other is provided on a main surface portion 302 that is the bottom of the locknut 30 (for detail, see FIG. 2). One of these two holes is a loose-insertion hole 3021 and is formed on the main surface portion 302 away from the center by perforation. The other hole is an engaging hole 3022 which is formed in the center of the main surface portion 302 by perforation. The loose-insertion hole 3021 has a diameter at least larger than that of the luer tip portion 122 so that the entire luer part 120 of the prefilled syringe 1 can be inserted into the hole with clearance therebetween. On the other hand, the engaging hole 2022 has a diameter slightly smaller than that of the luer tip portion 122 so that the stepped portion 123 of the luer part 120 is fitted thereto and the locknut 30 rotates with respect to the luer part 120. A passage 303 is formed between the loose-insertion hole 3021 and engaging hole 3022, having a diameter further smaller than that of the engaging hole 3022. The width of the passage 303 is slightly smaller than the diameter of the luer base portion 121 so that the luer part 120 shifts to the passage 303 side only when more than a certain amount of force is applied to the luer base portion 121.

1-3. Engagement of Syringe and Locknut

Figure 2A:
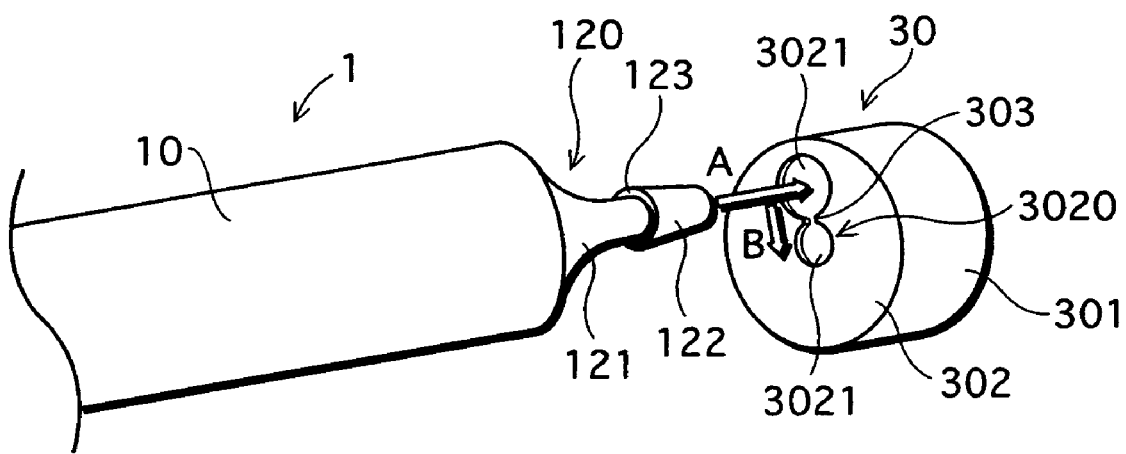
FIG. 2 shows the way to attach a locknut of Embodiment 1 to the prefilled syringe.
Figure 2B:
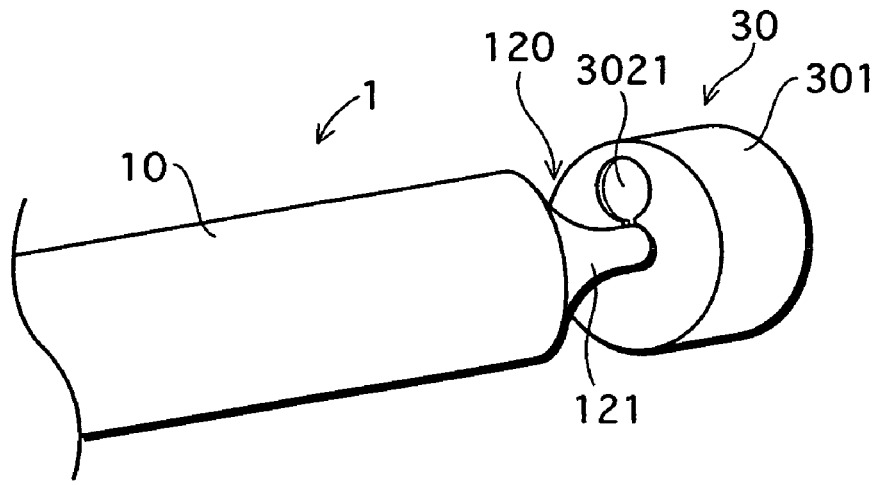

FIG. 2A shows how to attach the locknut 30 to the syringe 1 and FIG. 2B shows the lockout 30 after the attachment. As to the locknut 30 having the above structure, when using the prefilled syringe 1, the user first inserts the luer part 120 of the prefilled syringe 1 into the loose-insertion hole 3021 in the axial direction, as shown in FIG. 2A (FIG. 2A shows that the luer part 120 is about to be inserted in the direction A, i.e. the axial direction). Since the loose-insertion hole 3021 has a diameter sufficiently larger than that of the luer tip portion 122 of the luer part 120, the luer part 120 can be smoothly inserted into the locknut 30.

In the second step after the user has inserted the luer part 120 into the loose-insertion hole 3021 so as to assuredly insert the luer base portion 121 thereto, the user brings the lateral side of the luer base portion 121 into contact with the lateral surface of the loose-insertion hole 3021 and shifts the luer part 120 to the engaging hole 3022 via the passage 303 (FIG. 2A also shows that the luer part 120 is to be shifted in the direction B). In this process, the luer base portion 121 is forcedly shifted through the passage 303, then the stepped portion 123 shifts and becomes fitted into the small engaging hole 3022. Since the diameter of the engaging hole 3022 matches that of the stepped portion 123 and the passage 303 exists between the engaging hole 3022 and loose-insertion hole 3021, the stepped portion 123 of the luer part 120 abuts against the circumference of the engaging hole 3022 and is securely engaged in the axial direction, as shown in FIG. 2B.

After the lockout 30 having the snowman-shaped hole 3020 is engaged with the syringe body 10, these two can be readily detached from each other in the following manner. That is, the user shifts the luer part 120 from the engaging hole 3022 to the insertion hole 3021 as exerting some force on the luer part 120. This operation can be performed in a reversible and simple fashion (for example, in one hand), and the user is therefore able to easily attach the locknut 30 to the prefilled syringe 1 when required, and detach the locknut 30, when not required, to thereby use the prefilled syringe 1 alone.

Figure 3:
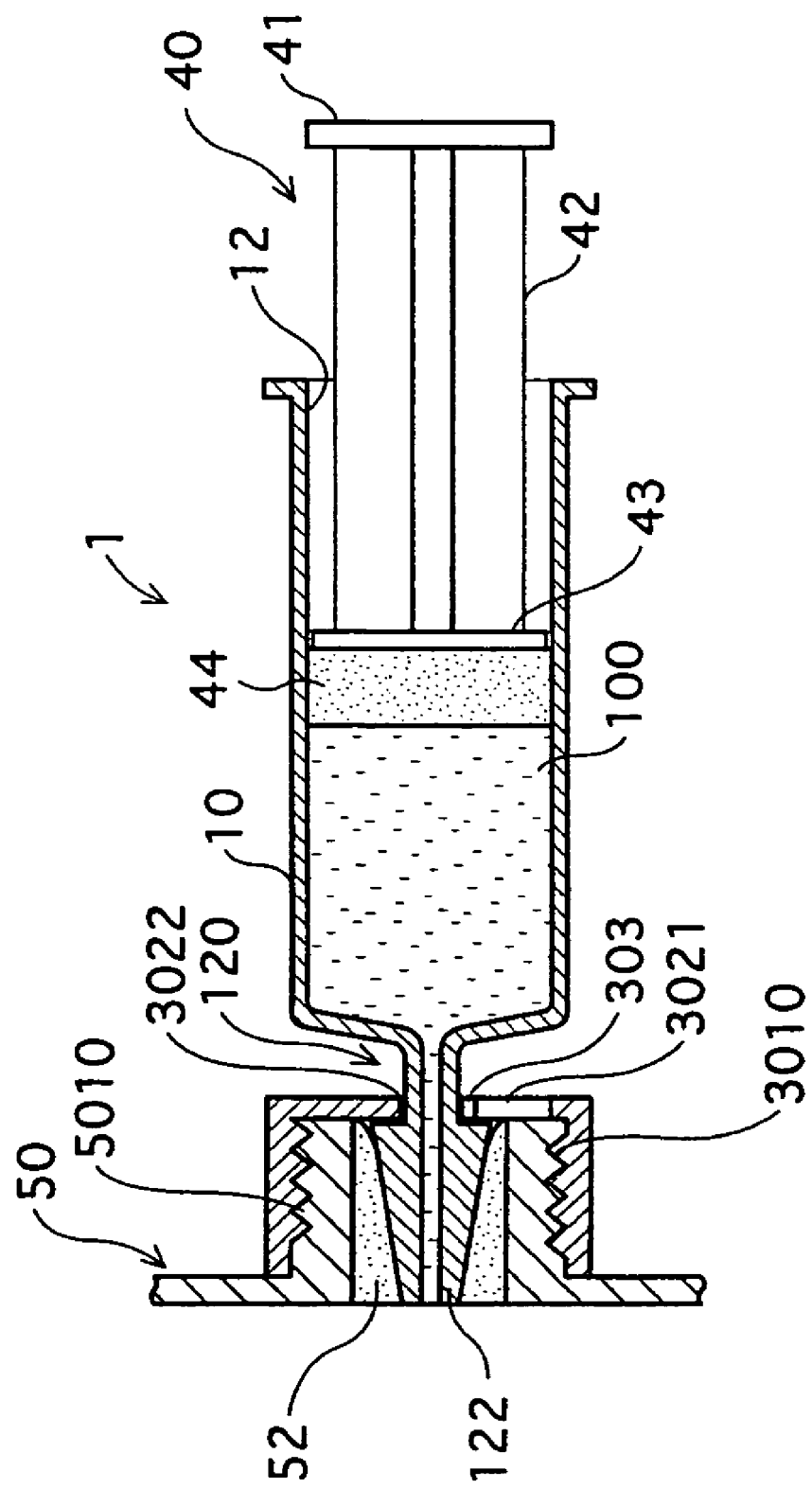
FIG. 3 shows the prefilled syringe of Embodiment 1 connected to a fixed connection port.

FIG. 3 is a cross sectional view showing that the prefilled syringe 1 is connected, using the locknut 30, to a fixed connection port 50 of a transfusion line system. As the male screw 5010 of the port 50 is screwed into the female screw 3010 of the lockout 30, the luer tip portion 122 of the luer part 120 of the prefilled syringe 1 canes in close contact with a packing 52 provided inside the port 50, and eventually gets inserted into the transfusion line while pressing the packing 52. At this point, in the locknut 30, the circumference of the engaging hole 3022 exerts pressure on the stepped portion 123 of the luer part 120 so that they tightly engage with each other. Thus, even if some degree of tension is applied to the prefilled syringe 1, the prefilled syringe 1 does not cane apart from the port 50 along the axial direction. As a result, the user is able to safely push the plunger 40 into the syringe body 10 accordingly and deliver a required amount of medication 100 to the inside of the port 50.

Figure 4:
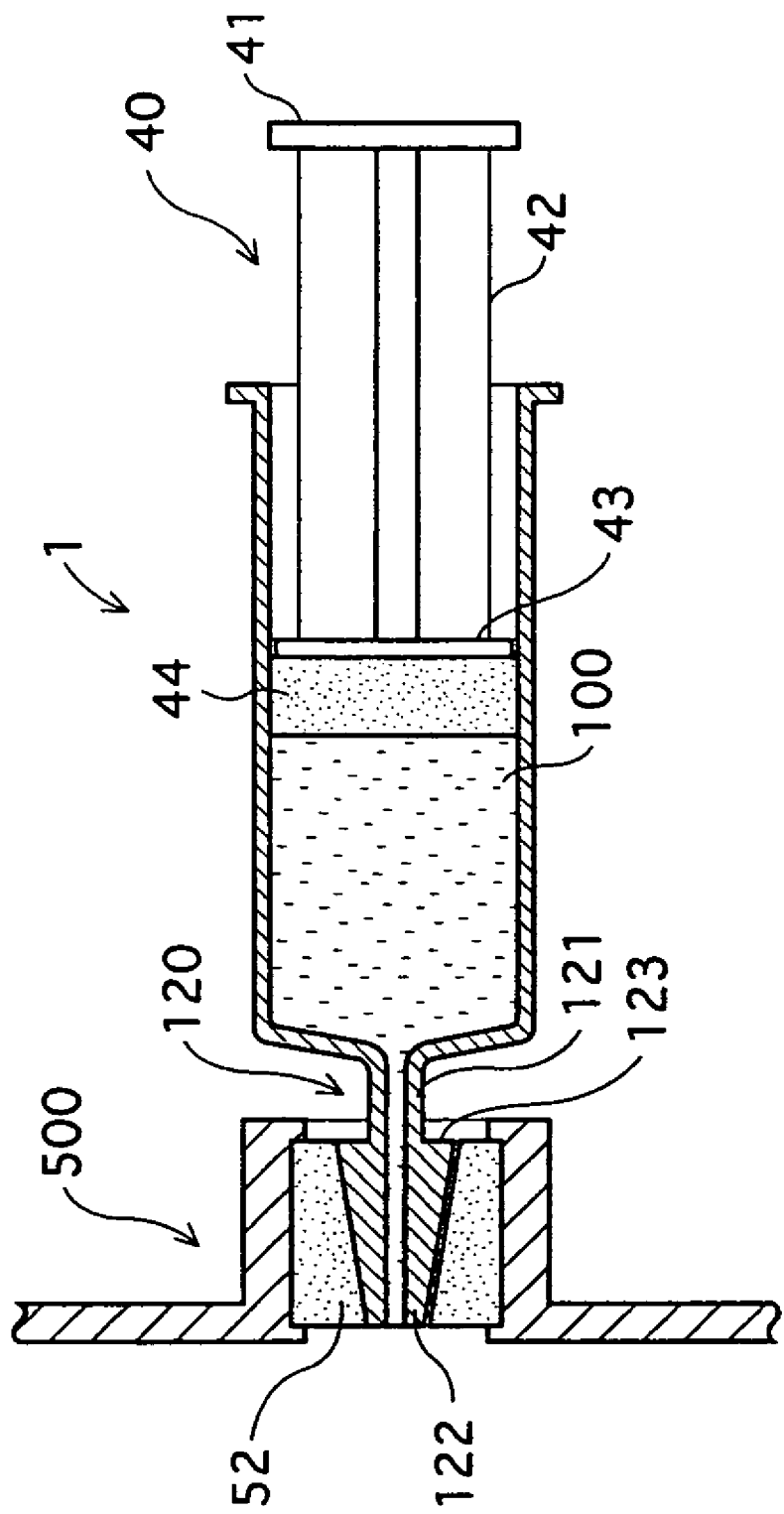
FIG. 4 shows the prefilled syringe of Embodiment 1 connected to a direct connection port.

On the other hand, FIG. 4 is a cross sectional view showing that the lockout 30 has been detached from the prefilled syringe 1, which is then connected to a direct connection port 500 of a transfusion line system. Thus, according to Embodiment 1, since the locknut 30 has been taken off, or otherwise may be an obstacle, the luer tip portion 122 of the prefilled syringe 1 is properly and tightly held by the packing 52 in the port 500, which makes a suitable connection between the prefilled syringe 1 and the port 500.

Figure 5:
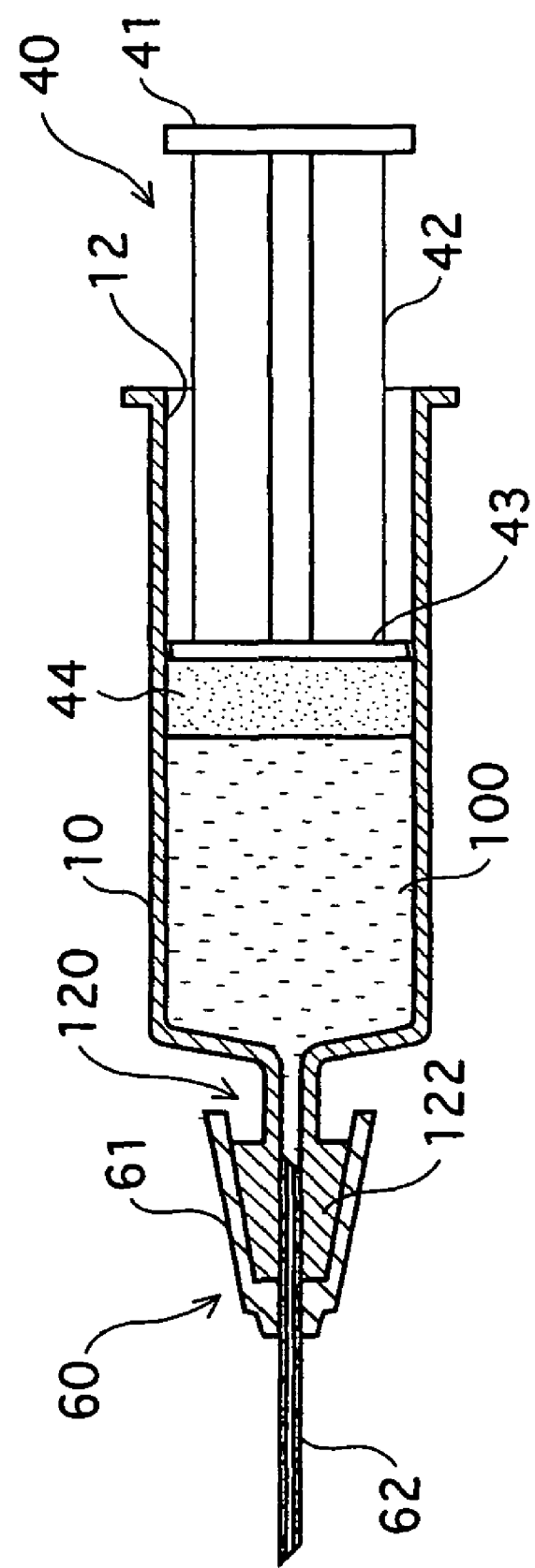
FIG. 5 shows the prefilled syringe of Embodiment 1 to which a conventional needle hub is attached.
Figure 43:
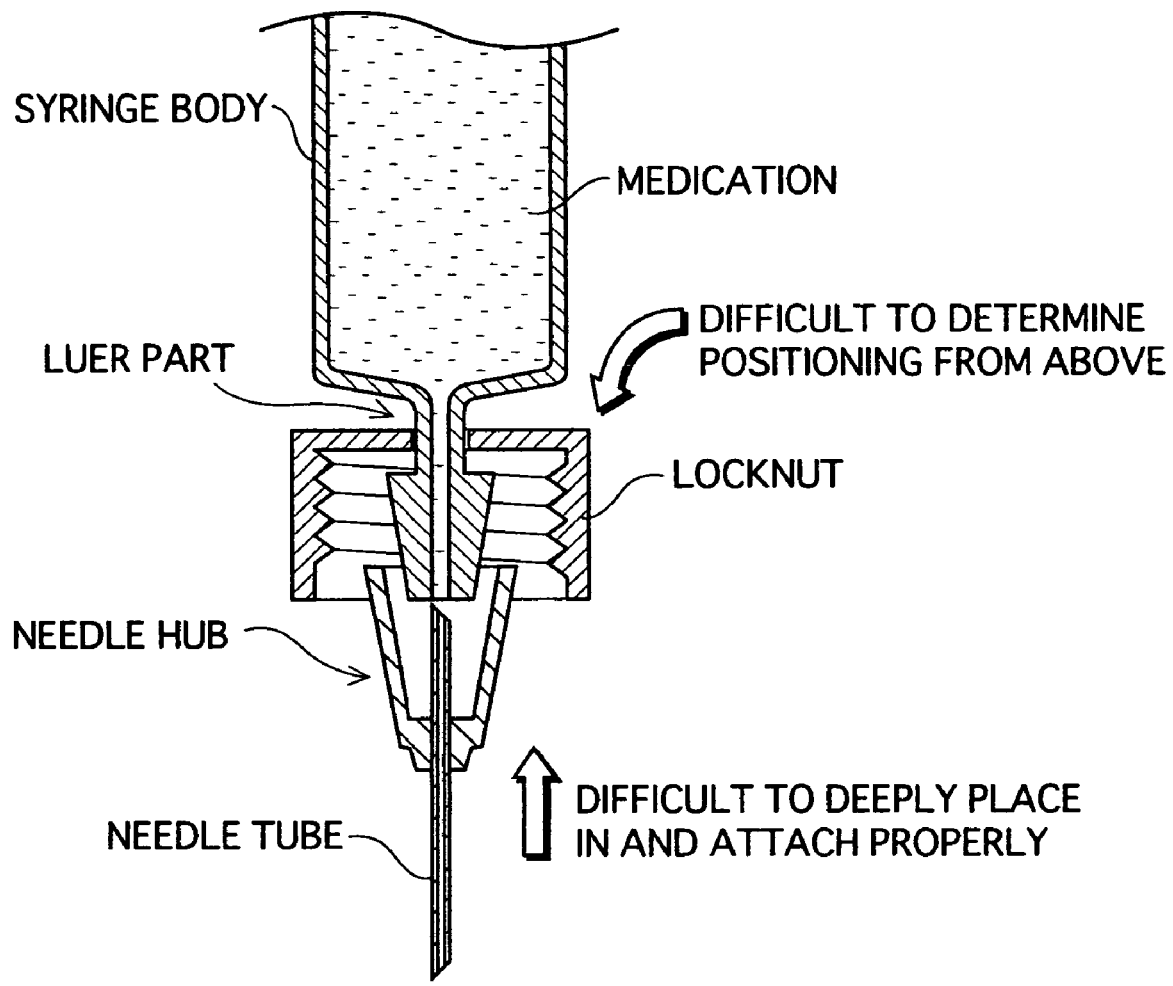
FIG. 43 shows a structure of a conventional locknut and a prefilled syringe.

FIG. 5 is a cross sectional view showing that the locknut 30 has been detached from the prefilled syringe 1 and a needle hub 60 is attached to the luer tip portion 122. The needle hub 60 has a structure in which a socket portion 61 composed of a resin material and formed to match the shape of the luer tip portion 122 holds a needle tube 62 which is an injection needle. With the conventional prefilled syringe in which the locknut is fixed and cannot be detached therefrom as shown in FIG. 43, the locknut obstructs the view of the user and makes it difficult to determine the positioning of the luer part and the needle hub, thereby creating the danger of the user mistakenly pricking himself/herself and coming into contact with infectious material. In addition, the conventional problem that the needle hub cannot be deeply placed in and attached to the luer part due to the presence of the lockout can be fundamentally solved by Embodiment 1 since the snowman-shaped hole 3020 enables easy detachment of the locknut 30 from the prefilled syringe 1.

Other Embodiments

Note that although in Embodiment 1 the snowman-shaped hole is formed by circular insertion and engaging holes communicating with each other via the passage, the following embodiments are also within the scope of the present invention.

2. Embodiment 2

Figure 6:
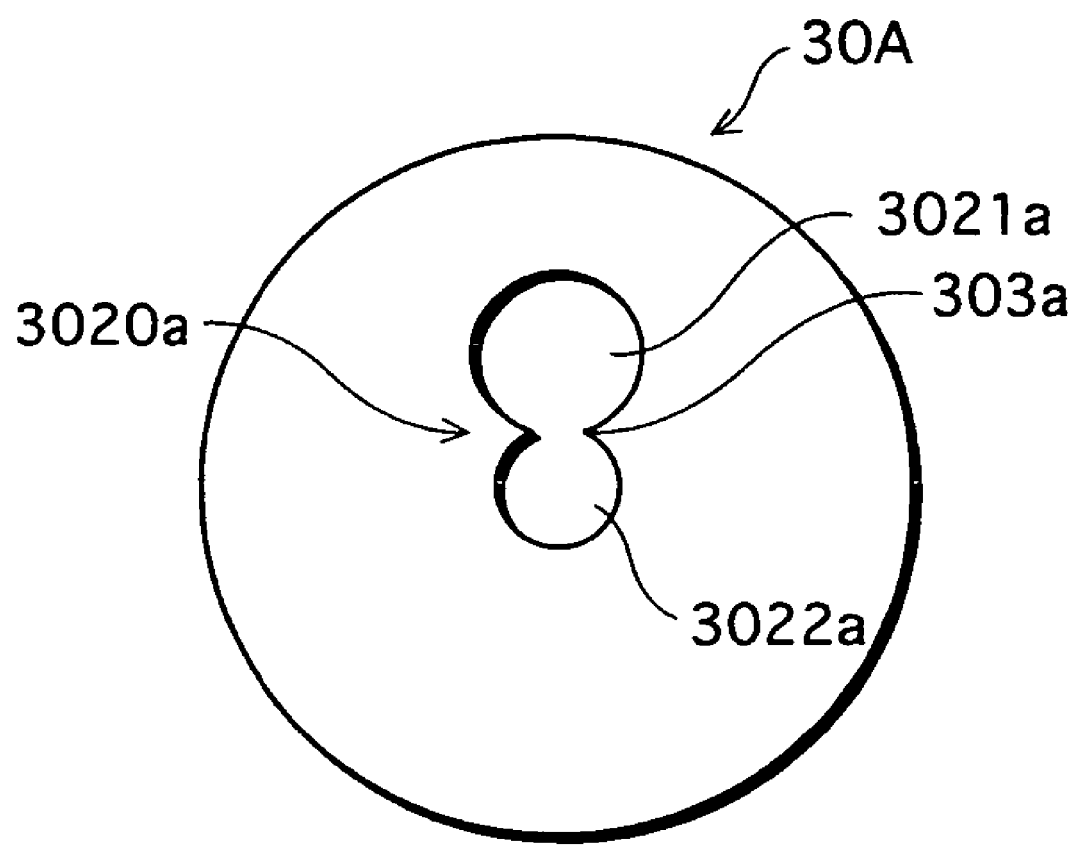
FIG. 6 shows a structure of a locknut of Embodiment 2.

With a snowman-shaped hole 3020a in a locknut 30A of Embodiment 2 shown in FIG. 6, arcs of a loose-insertion hole 3021a and an engaging hole 3022a are partially overlapped with each other, and two circumferences of these holes where they overlap form a passage 303a.

With the snowman-shaped hole 3020a having such a shape, the present invention is able to achieve an equivalent effect to that of Embodiment 1. In addition, since the passage 303a of Embodiment 2 is formed where the loose-insertion hole 3021a and engaging hole 3022a overlap, it is rather edged as compared with that of Embodiment 1, and the luer part 120 is reliably engaged with the engaging hole 3022a due to the shape.

3. Embodiment 3

Figure 7:
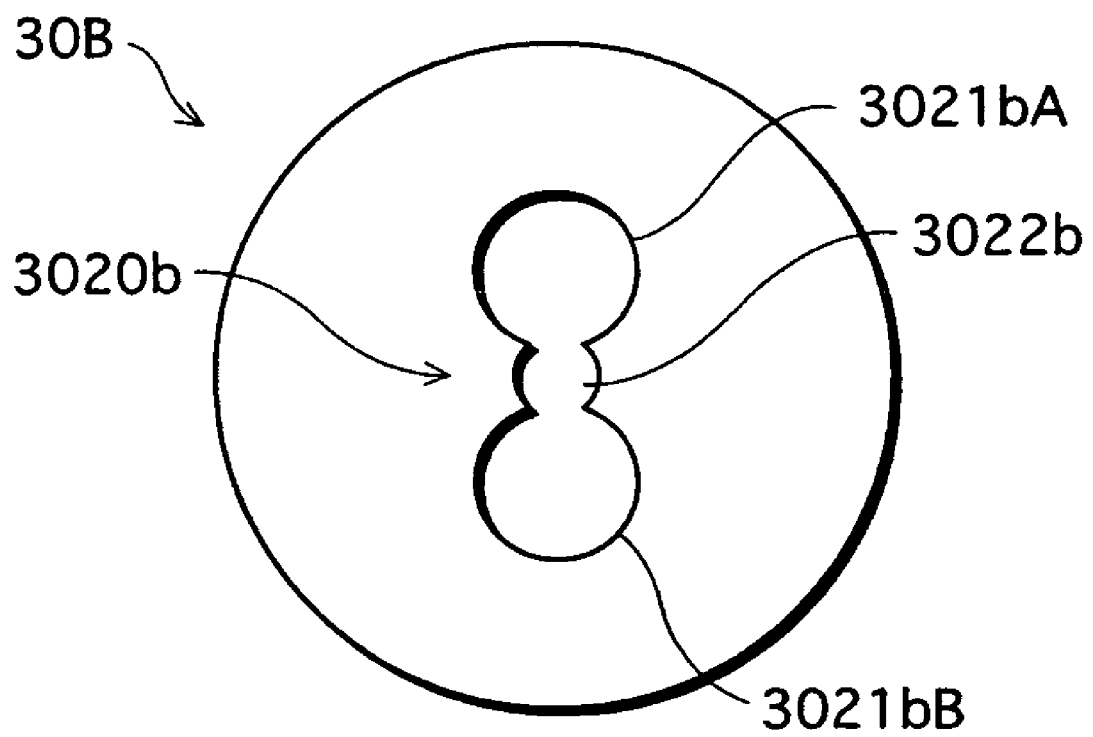
FIG. 7 shows a structure of a lockout of Embodiment 3.

With a snowman-shaped hole 3020b in a locknut 30B according to Embodiment 3 shown in FIG. 7, an engaging hole 3022b is formed between two insertion holes 3021bA and 3021bB. Although arcs of the engaging hole 3022b and each of the insertion holes 3021bA and 3021bB are partially overlapped with each other, these holes may be communicated with each other by passages therebetween. In addition, the insertion holes 3021bA and 3021bB need not have the same size and shape, but need to have sizes such that at least the stepped portion 123 of the luer part 120 can be inserted thereto with clearance therebetween.

With the snowman-shaped hole 3020b having such a structure, the user can detach the locknut 30 easily when using the syringe 1 since the luer part 120 can be shifted from the engaging hole 3022b to either of the two insertion holes 3021bA and 3021bB. This results in reducing the operational load on the user. Embodiment 3 is expected to achieve a very high level of convenience especially in medical practices which require the user to handle the prefilled syringe 1 and locknut 30 in one hand based on the treatment method using the prefilled syringe 1.

4. Embodiment 4

Figure 8:
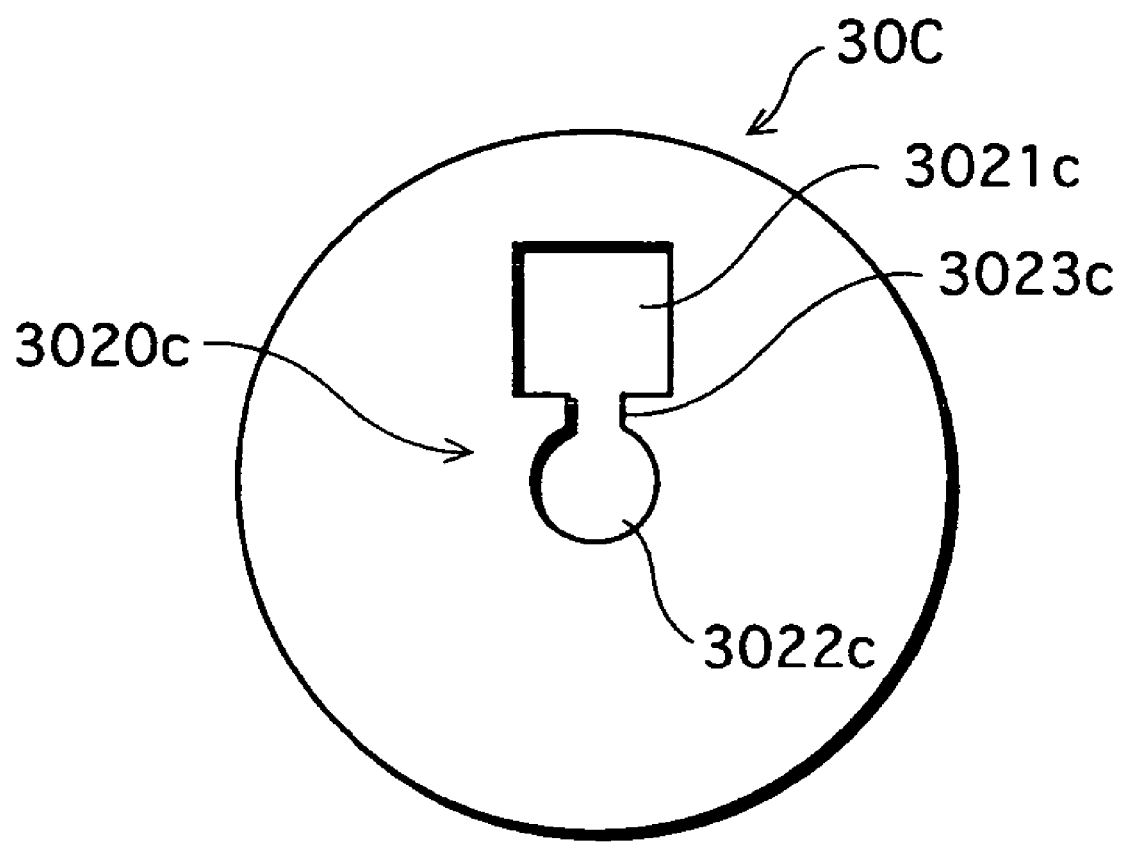
FIG. 8 shows a structure of a locknut of Embodiment 4.

With a snowman-shaped hole 3020c in a locknut 30C of Embodiment 4 shown in FIG. 8, a circular engaging hole 3022c is communicated with a rectangular loose-insertion hole 3021c via a passage 3023c.

With such a structure also, a similar effect to that of the locknut 30 of Embodiment 1 can be achieved. An additional advantage is that the user readily recognizes and distinguishes the loose-insertion hole 3021c and engaging hole 3022c without confusion and is able to properly use the lockout 30C since the shapes of these holes are distinctly different.

5. Embodiment 5

Figure 9:
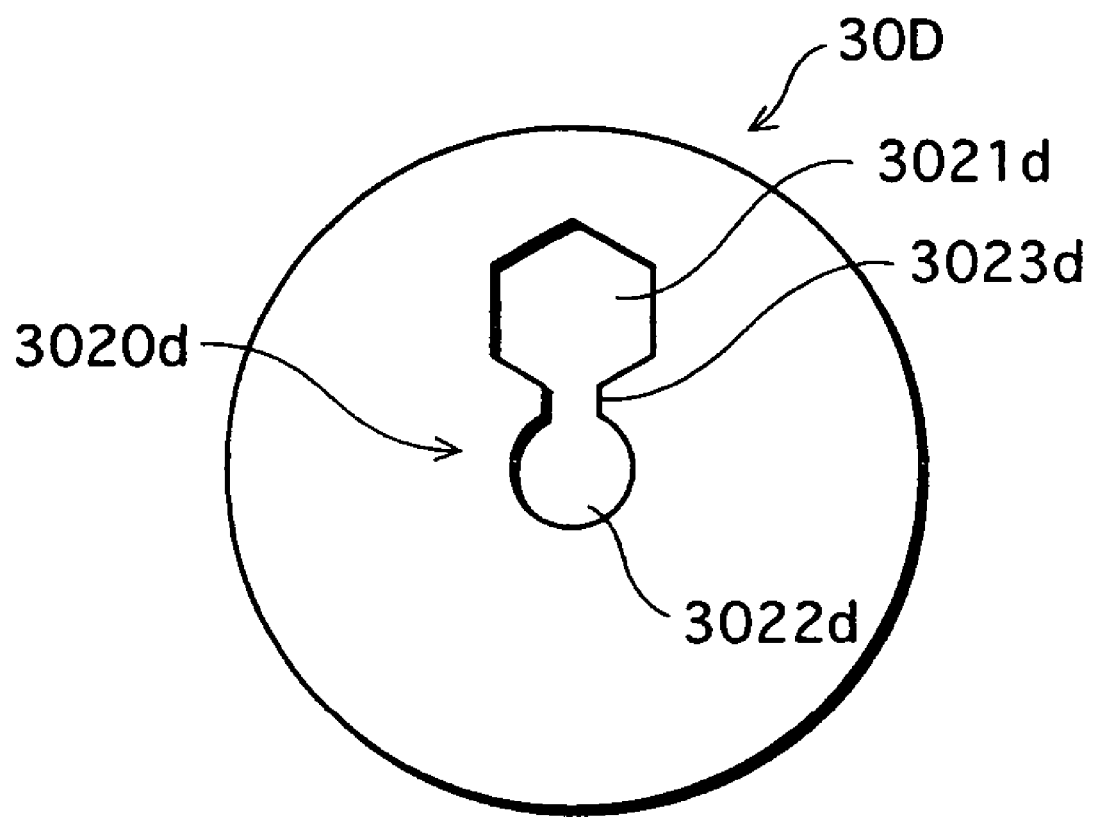
FIG. 9 shows a structure of a locknut of Embodiment 5.

With a snowman-shaped hole 3020d in a locknut 30D of Embodiment 5 shown in FIG. 9, a circular engaging hole 3022d is communicated with a hexagonal loose-insertion hole 3021d via a passage 3023d.

With such a structure also, a similar effect to that of the locknut 30 of Embodiment 1 can be achieved. Similarly to Embodiment 4, since the shapes of the loose-insertion hole 3021d and engaging hole 3022d are distinctly different, the user readily recognizes and distinguishes these two holes without confusion and is able to properly use the lockout 30D.

Additional Particulars Regarding Embodiments 1 through 5

Although the prefilled syringe 1 of the present invention has been explained with an example in which the needle hub 60 is attached after the lockout 30 being detached, the present invention is not limited to that case. Instead of a needle hub, a tubelike luer or a tube may be used. It is effective to attach, from the top, a cap or the like to the prefilled syringe 1 with a needle hub attached thereto so as to protectively cover the needle hub and needle tube for the purpose of avoiding accidental pricking. As such a cap, one similar to a cap for a vial container can be used.

Each embodiment described above discloses a structural example of a connector (locknut) in which a screw thread is cut to form a female screw. However, the present invention is not confined to this structure, and the prefilled syringe 1 may be appropriately connected to the port of a line system using a discontinuous thread, a cup joint, or another structure.

The luer part of the syringe used in the present invention does not necessarily have a circular cross section, and either one of the luer tip portion and the luer base portion or both have rectangular, elliptic, or triangle cross sections. Note however that it is preferable that the shape of the engaging hole be appropriately decided in accordance with the cross sectional shape of the stepped portion of the luer part so as to stably and reliably engage the luer part in the engaging hole of the locknut.

6. Embodiment 6

6-1. Overall Structure of Prefilled Syringe

Figure 10:
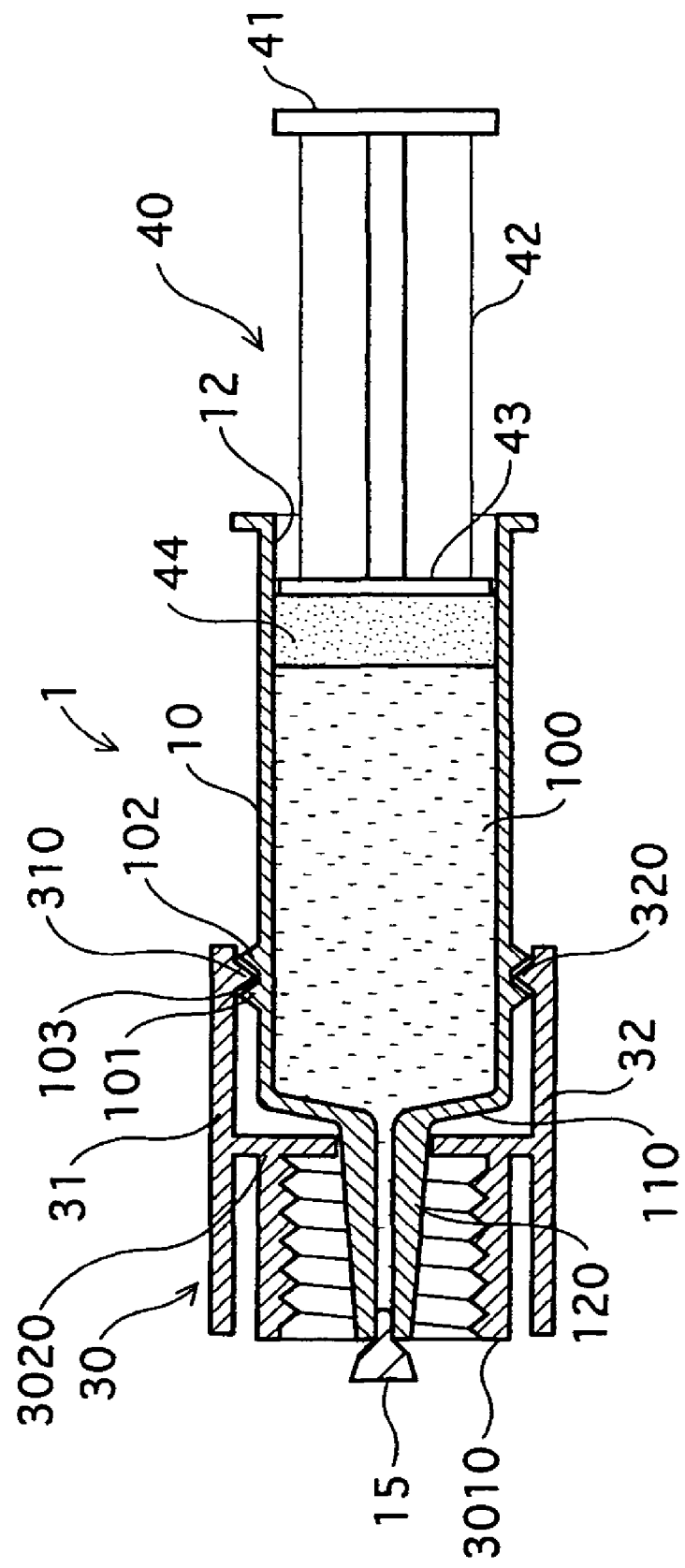
FIG. 10 is a cross sectional view showing a structure of a prefilled syringe of Embodiment 6.

FIG. 10 is a cross sectional view showing structures of a prefilled syringe and a connector (lockout) according to Embodiment 1. Note that Embodiment 6 has a structure in which a prefilled syringe and a locknut are combined, however, the present invention is applicable to syringes other than prefilled syringes. For convenience of explanation, the plunger 40 is shown here in normal lateral view rather than in cross section.

The prefilled syringe 1 shown in the figure may comprise the syringe body 10, the plunger (also referred to as a piston) 40 and the like. The syringe body 10 may be a tubular body formed by injection molding a material with high chemical resistance, such as polyethylene, polypropylene, polycarbonate or polyvinyl chloride. The tip end of the syringe body 10 is sealed by the top face portion 110, and the luer part 120 formed by drawing to give a tapered shape juts or extends out from the center of the top face portion 110. The luer part 120 is formed in a tapered shape in compliance with IS06/100 so that the normal needle hub 20 is easily attached thereto. In FIG. 10, the cap 20 is attached to the tip of the luer part 120. The prefilled syringe 1 of the present invention is configured, such that convex portions 101 and 102 and a concave portion 103, which form an engaging portion, are provided side by side, situated closer to the luer part 120, so as to encircle the circumference of the syringe body 10. These portions are for engaging with the locknut 30 to be hereinafter described.

On the other hand, the opening 12 is formed at the posterior end of the syringe body 10.

In the following description, the longitudinal direction of the syringe body 10 is referred to as an "axial direction" while a direction perpendicular to the axial direction is referred to as a "radial direction".

The plunger 40 is made of a resin material with high chemical resistance, similarly to the syringe body 10, and includes the plunger body 42 having a cruciform cross sectional shape for the purpose of reinforcement, at each end of which are formed disk-shaped end pieces having main surfaces in the radial direction. One of the end pieces is the pressing end portion 41 to be pressed by the user with a thumb, and the other end piece is the head portion 43 that is inserted inside the syringe body 10 in the axial direction.

The packing 44 is provided at the tip of the head portion 43 in a manner to make tight contact with the internal wall of the syringe body 10. Here, medication 100 is held in the syringe body 10, which is internally sealed by the packing 44 and the cap 20.

When using the prefilled syringe 1 having such a structure, the user removes the cap 20 to enable discharge of the medication 100. As the user pushes the pressing end portion 41 of the plunger 40 into the syringe body 10 with a thumb, the medication 100 is discharged from the tip of the luer part 120 according to the depressed amount of the plunger.

6-2. Structure of Locknut

The prefilled syringe 1 of Embodiment 6 is configured, such that the locknut 30, which is a connector easily detachable from the luer part 120, is attached thereto as shown in FIG. 10. The locknut 30 is used in the medical field as a connection implement for connecting the prefilled syringe 10 to a fixed connection port of a transfusion line system or blood collection line system.

The locknut 30 has a cylindrical shape having a bottom, and is formed by injection molding a resin material with high mechanical strength. A screw thread is cut on the internal surface of a lateral side portion 301, which corresponds to the cylindrical part of the locknut 30, to thereby form a female screw 3010 in compliance with, for example, ISO594-2. The female screw 3010 engages with the male screw 5010 to be hereinafter described.

A rib 3020 having in the center a perforation with a size such that the luer part 120 can be inserted, leaving no space therebetween, is formed in the lockout 30, and forms a bulkhead which divides the internal space of the lockout 30 into a syringe side and a port side. On the other hand, outside the locknut 30, two plate-like arms 31 and 32 are formed parallel to the syringe body 10 in the axial direction to make T Shapes with the rib. Tab projections 310 and 320 having triangular cross sections are formed on the inner sides of the tip ends of the arms 31 and 32. The shape of the projections 310 and 320 is made to be complementary to that of the concave portion 103 of the syringe body 10.

6-3. Detachment of Lockout from Syringe

Figure 11:
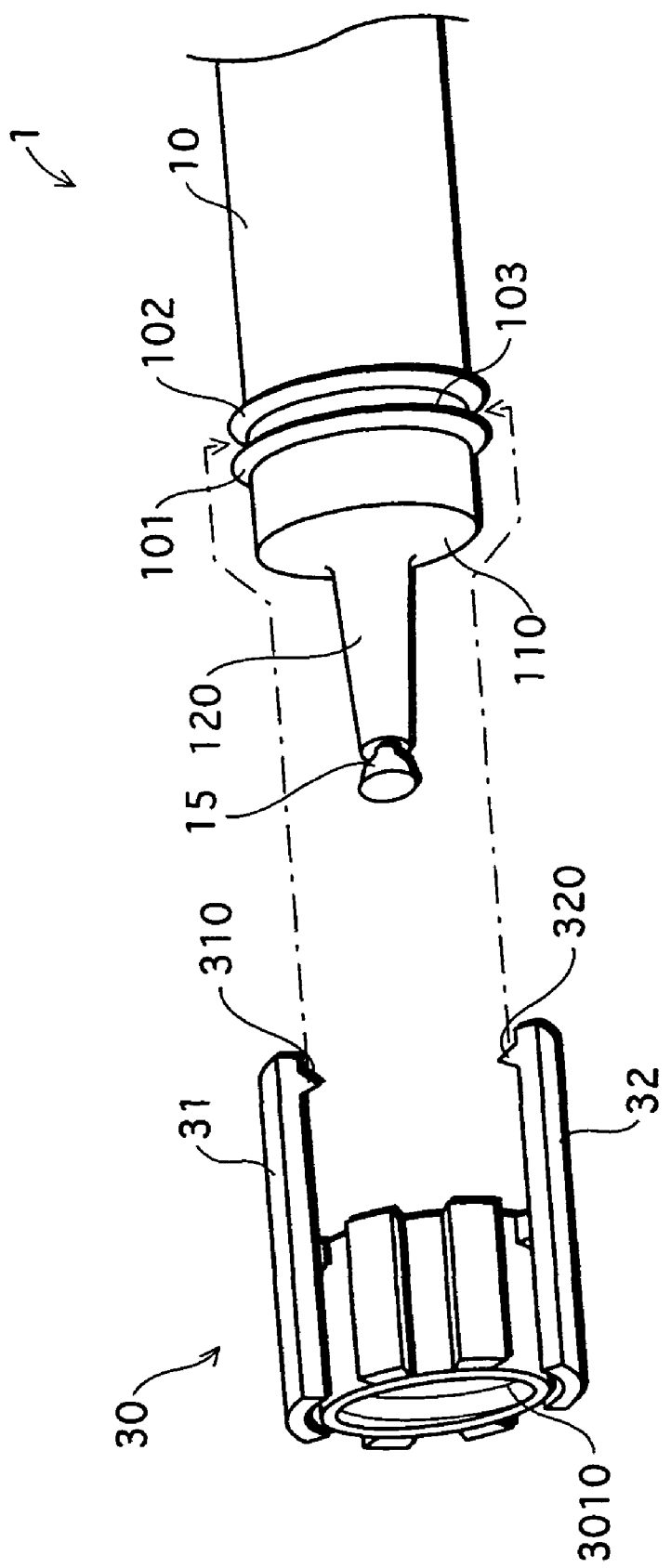
FIG. 11 shows the way to attach a locknut of Embodiment 6 to the prefilled syringe.

FIG. 11 shows the way of engaging the lockout 30 and the state of locknut 30 after the engagement.

As to the locknut 30 having the above structure, when the prefilled syringe 1 is used, the user first inserts the luer part 120 into the locknut 30 (here, the luer part 120 is inserted in the center of the rib 3020 inside the locknut 30) as shown in FIG. 11. At this point, the user makes sure that the luer part 120 is inserted so that the rib 3020 comes all the way to the base of the luer part 120.

In the second step, using the arms 31 and 32 extending from the locknut 30, the user engages the projections 310 and 320 provided on the inner sides of the arms 31 and 32 with the concave portion 103 of the syringe body 10 by elastically contacting and fitting them with each other. The shape of the projection 310 and 320 is formed so as to conform to the convex portions 101 and 102 and the concave portion 103, and therefore the locknut 30 is securely kept on the syringe body 10 by the engagement.

Figure 12:
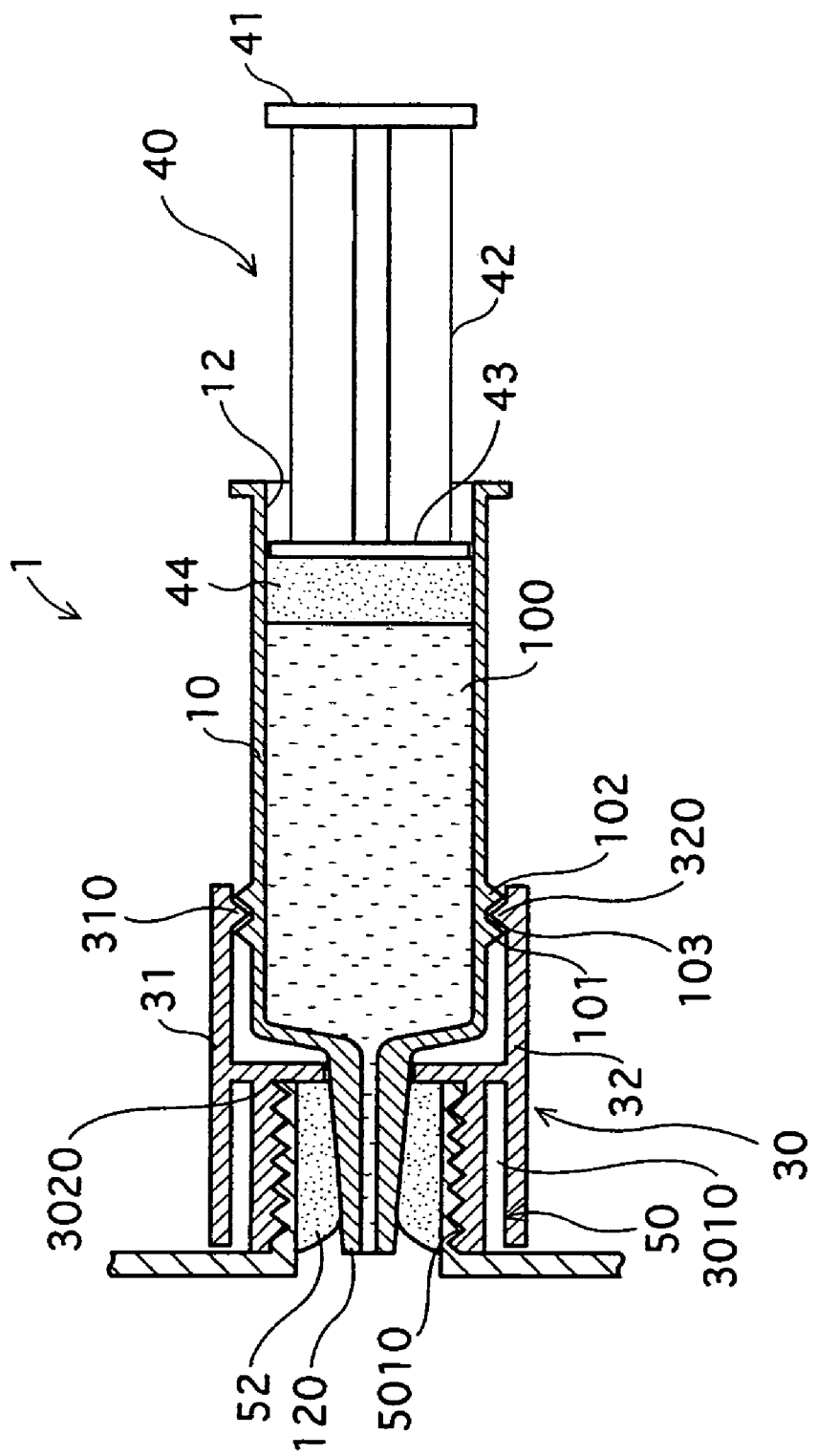
FIG. 12 shows the locknut of Embodiment 6 fitted to the prefilled syringe.

FIG. 12 is a cross sectional view showing the prefilled syringe 1 that is, using the lockout 30, connected to the fixed connection port 50 of a transfusion line system. As the male screw 5010 of the port 50 is screwed into the female screw 3010 of the lockout 30, the tip of the luer part 120 of the prefilled syringe 1 is tightly pressing the packing 52 provided inside the port 50, and eventually gets inserted into the transfusion line. The prefilled syringe 1 is not disengaged while in use because the syringe body 10 is securely fixed with the locknut 30 by the convex portions 101 and 102, concave portion 103, and projections 310 and 320, and besides the luer part 120 is supported by the rib 3020 in the lockout 30 to keep the luer part 120 in place. As a result, the user is able to safely push the plunger 40 into the syringe body 10 accordingly and deliver a required amount of medication 100 to the inside of the port 50.

According to Embodiment 6, after being engaged with the syringe body 10, the locknut 30 can be easily disengaged from the syringe 1 by performing a predetermined operation in the following manner. This operation can be performed in a reversible and simple fashion (for example, in one hand), and the user is therefore able to easily engage the locknut 30 with the prefilled syringe 1 when required, and detach the locknut 30, when not required, to thereby use the prefilled syringe 1 alone.

Figure 13:
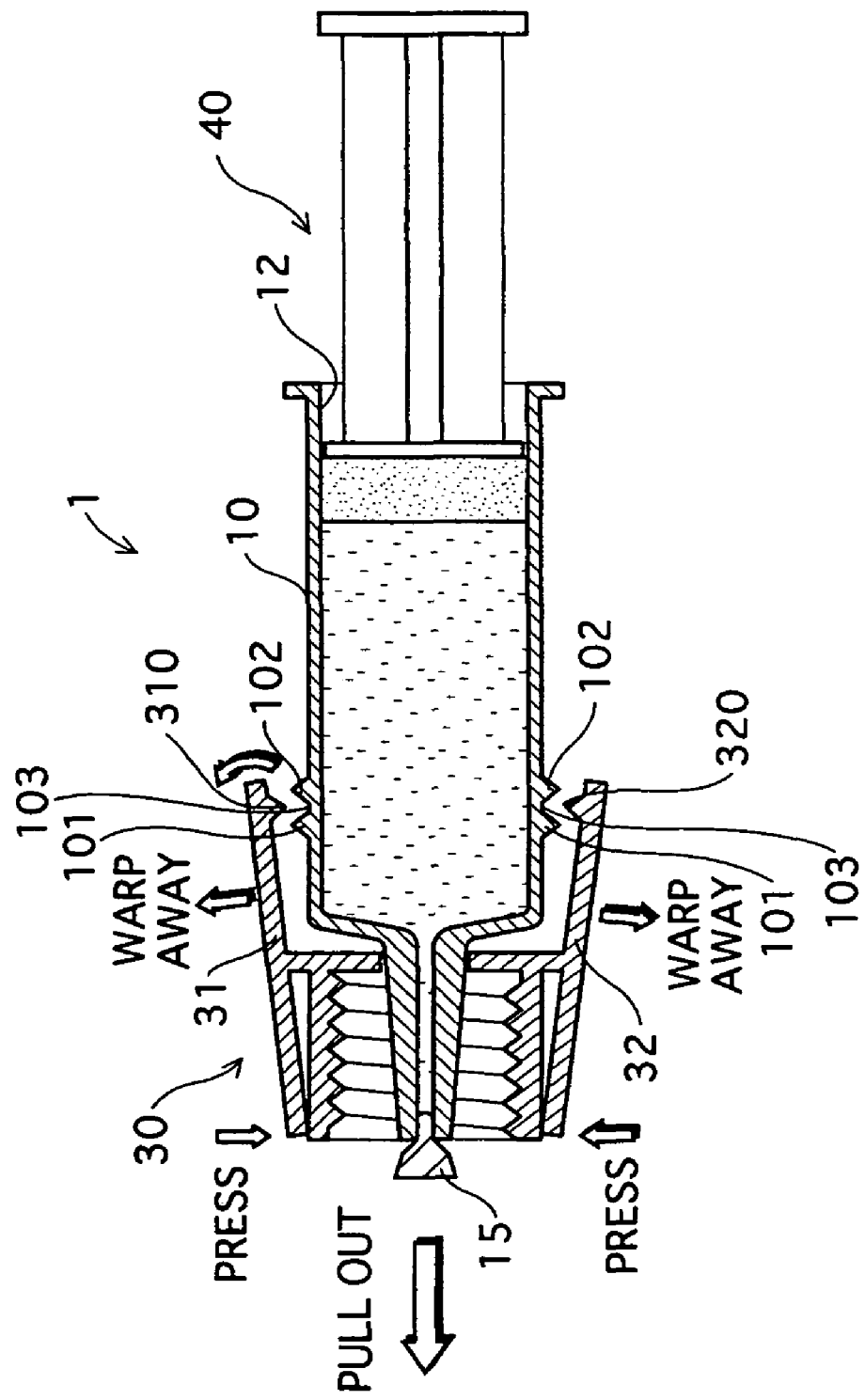
FIG. 13 is a cross sectional view of the prefilled syringe and locknut of Embodiment 6.

In a specific method of disengaging the locknut 30 (the predetermined operation), the user presses the arms 31 and 32 on the anterior side of the syringe 1, as shown in FIG. 13, which is a cross sectional view of the syringe 1 and locknut 30. In this embodiment, "the principle of leverage" may be applied, with the centers of the arms 31 and 32 being fulcrums while the points where the projections 310 and 320 abut on the convex portions 101 being working points. Accordingly, the ends of the arms 31 and 32 where the projections 310 and 320 are provided warp away from the syringe body 10 (i.e. an external force is applied to the locknut 30 in a direction different from the syringe axial direction). Herewith, the projections 310 and 320 detach and came free, at least, from the convex portion 102 and concave portion 103. While maintaining this state, the user is able to pull out the locknut 30 from the syringe 1 with a little force. Note that the locknut 30 can be easily disengaged from the syringe body 10 by spreading outward the ends of the arms 31 and 32 with the projections 310 and 320 by fingers, instead of pressing the arms 31 and 32 on the anterior side of the syringe 1.

It is desirable that the arms 31 and 32 be provided on the locknut 30 so that T shapes are formed with the rib, and points where the arms 31 and 32 abut on the rib become fulcrums. This, the user can easily disengage the locknut 30 from the syringe body 10 by pushing the posterior ends of the arms 31 and 32 to spread the anterior ends thereof.

Figure 14:
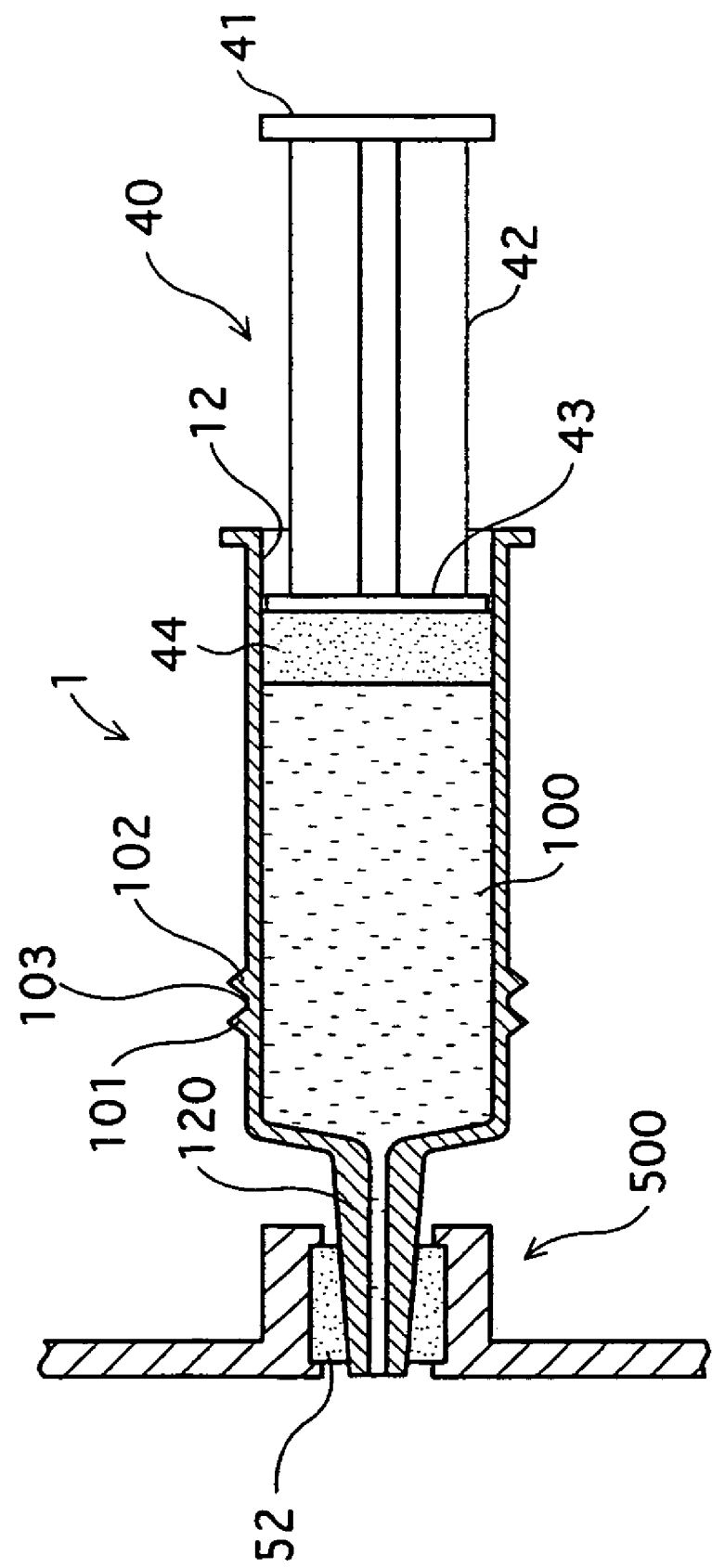
FIG. 14 is a cross sectional view showing the prefilled syringe of Embodiment 6 connected to a direct connection port of a transfusion line system.

FIG. 14 is a cross sectional view showing that the prefilled syringe 1 may be connected to the direct connection port 500 of a transfusion line system after the locknut 30 has been detached therefrom according to the above method. Thus, in Embodiment 6, since the lockout 30 has been removed, or may otherwise be an obstacle, the luer part 120 of the prefilled syringe 1 is properly and tightly held by the packing 52 in the port 500, which makes a suitable connection between the prefilled syringe 1 and the port 500.

Figure 15:
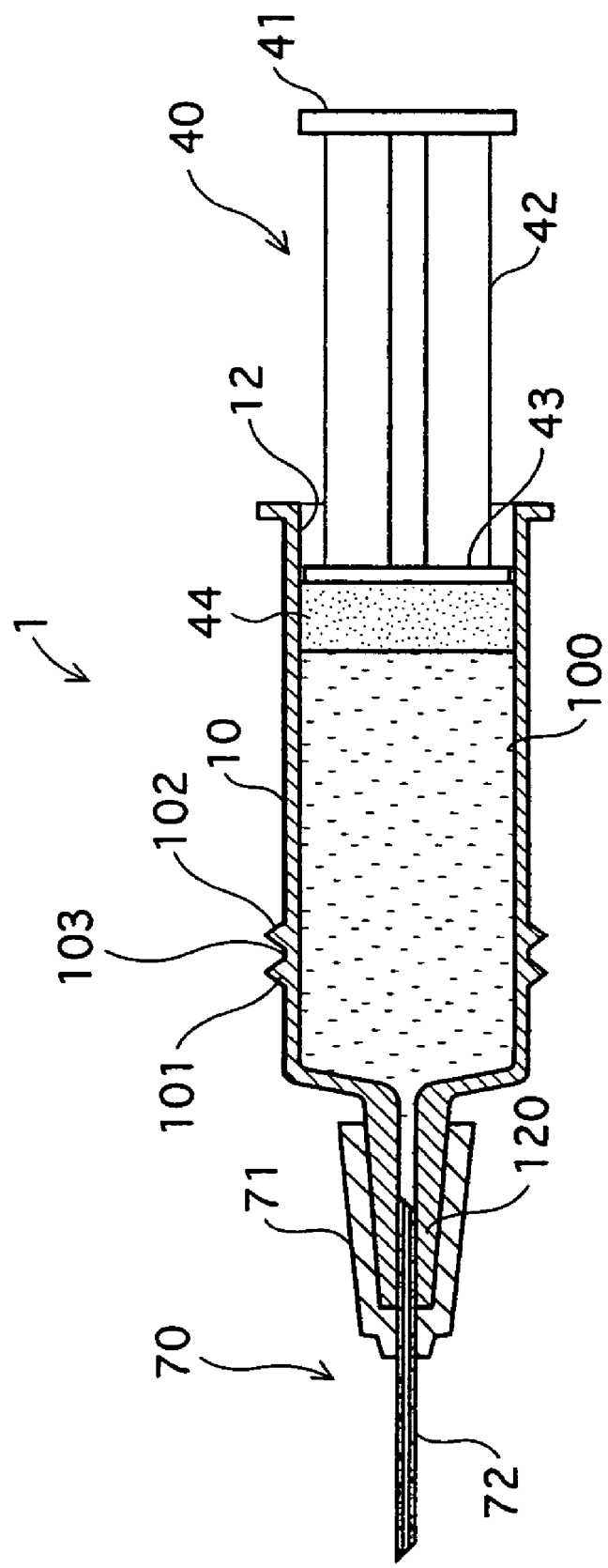
FIG. 15 is a cross sectional view showing a luer part of the prefilled syringe of Embodiment 6 to which a needle hub is attached.

FIG. 15 is a cross sectional view showing that the needle hub 70 is attached to the luer part 120 after the locknut 30 has been detached from the prefilled syringe 1. The needle hub 70 has a structure in which a socket portion 71 composed of a resin material and formed to match the shape of the luer part 120 holds a needle tube 72 which is an injection needle. With the conventional prefilled syringe in which the locknut is fixed and cannot be detached therefrom as shown in FIG. 43, the locknut obstructs the view of the user and makes it difficult to check on the positioning of the luer and the needle hub, thereby creating the danger of the user mistakenly pricking himself/herself and coming into contact with infectious material. In addition, the conventional problem that the needle hub cannot be deeply placed in and attached to the luer part due to the presence of the locknut can be fundamentally solved by Embodiment 6 since the user can readily detach the locknut 30 from the prefilled syringe 1 by handling the arms 31 and 32 in a simple fashion.

Other Embodiments

Note that Embodiment 6 has a structure in which one projection 310 or 320 having a triangular cross section is formed on the end of each arm 31 and 32 and fitted with the convex portions 101 and 102 and concave portion 103 of the syringe body 10. However, the following embodiments are also within the scope of the present invention.

7. Embodiment 7

Figure 16:
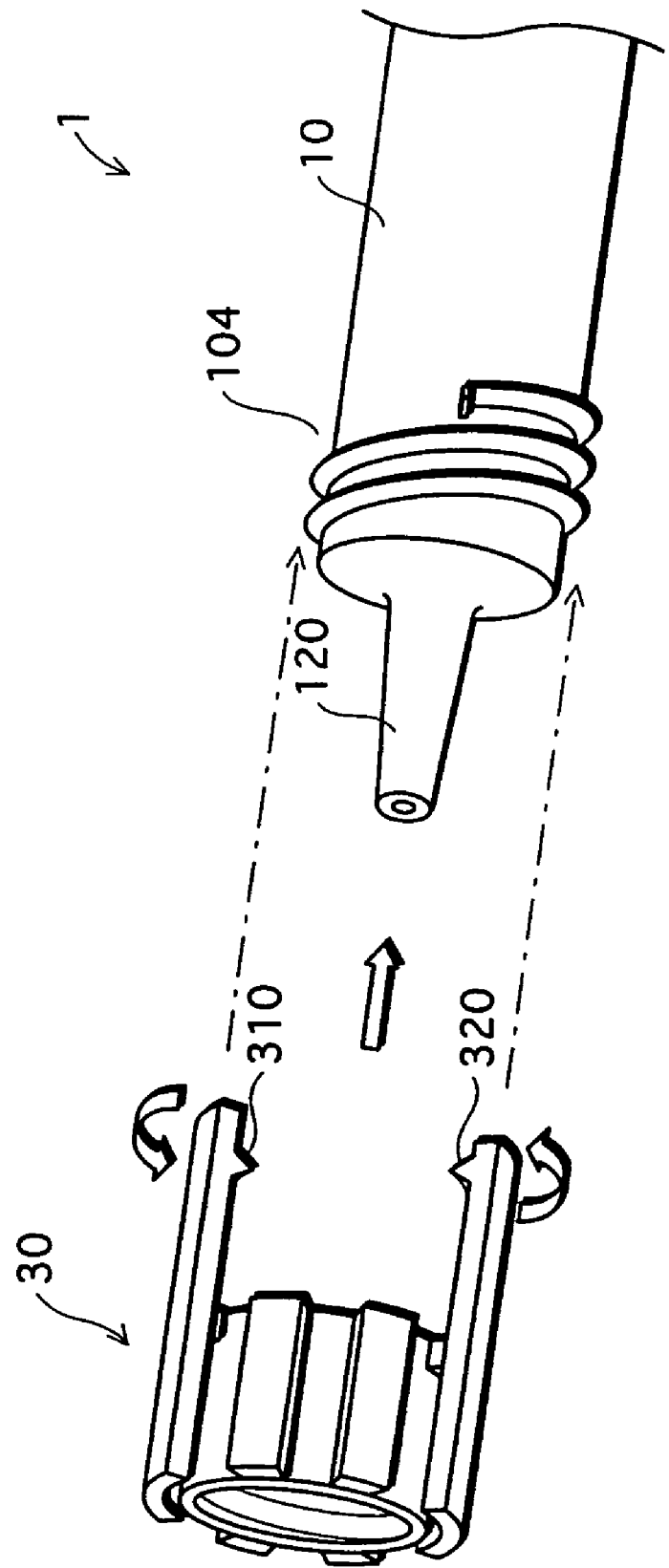
FIG. 16 shows a structure of a locknut and a prefilled syringe of Embodiment 7.

As to Embodiment 7 shown in FIG. 16, although the structure of the locknut 30 is substantially similar to that of Embodiment 1, the syringe body 10 has a slightly different structure. Embodiment 7 is characterized by a male screw portion 104 formed with a helical convex portion provided on the outer surface of the syringe body 10.

With using the syringe body 10 having the male screw portion 104 also, the present invention is able to achieve an equivalent effect to that of Embodiment 6. In addition, Embodiment 7 allows for a slight adjustment of the positional relationship between the syringe body 10 and the locknut 30 by changing the degree of screwing of the male screw portion 104 into the lockout 30 (i.e. how far the male screw portion 104 is screwed into the locknut 30). Consequently, Embodiment 7 achieves a good connection of the syringe 1 to a fixed connection port corresponding to the luer part 120 shorter than a conventional one.

8. Embodiment 8

Figure 17:
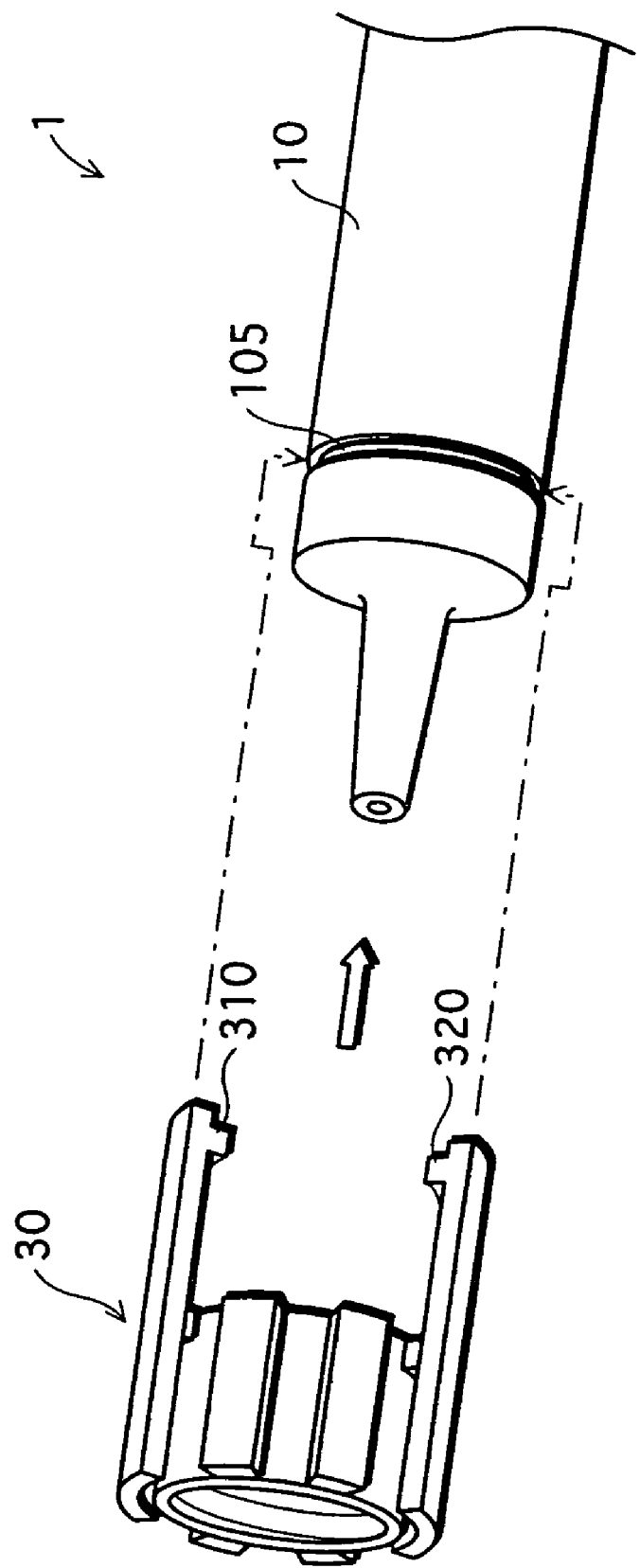
FIG. 17 shows a structure of a locknut and a prefilled syringe of Embodiment 8.

As to Embodiment 8 shown in FIG. 17, although the structure of the locknut 30 is substantially similar to that of Embodiment 6, the syringe body 10 has a slightly different structure. Embodiment 8 is configured to have a concave portion 105 which is formed by concaving the outer surface of the syringe body 10.

With using the syringe body 10 having the concave portion 105 also, Embodiment 8 is able to achieve an equivalent effect to that of Embodiment 6. In addition, since the syringe body 10 of Embodiment 8 has a smooth surface without the convex portions 101 and 102, a problem such as the convex portions 101 and 102 of the syringe body 10 catching the user's clothes while in use can be avoided. It is a matter of course that the syringe body 10 according to Embodiment 8 must have enough thickness for the formation of the concave portion 105.

9. Embodiment 9

Figure 18:
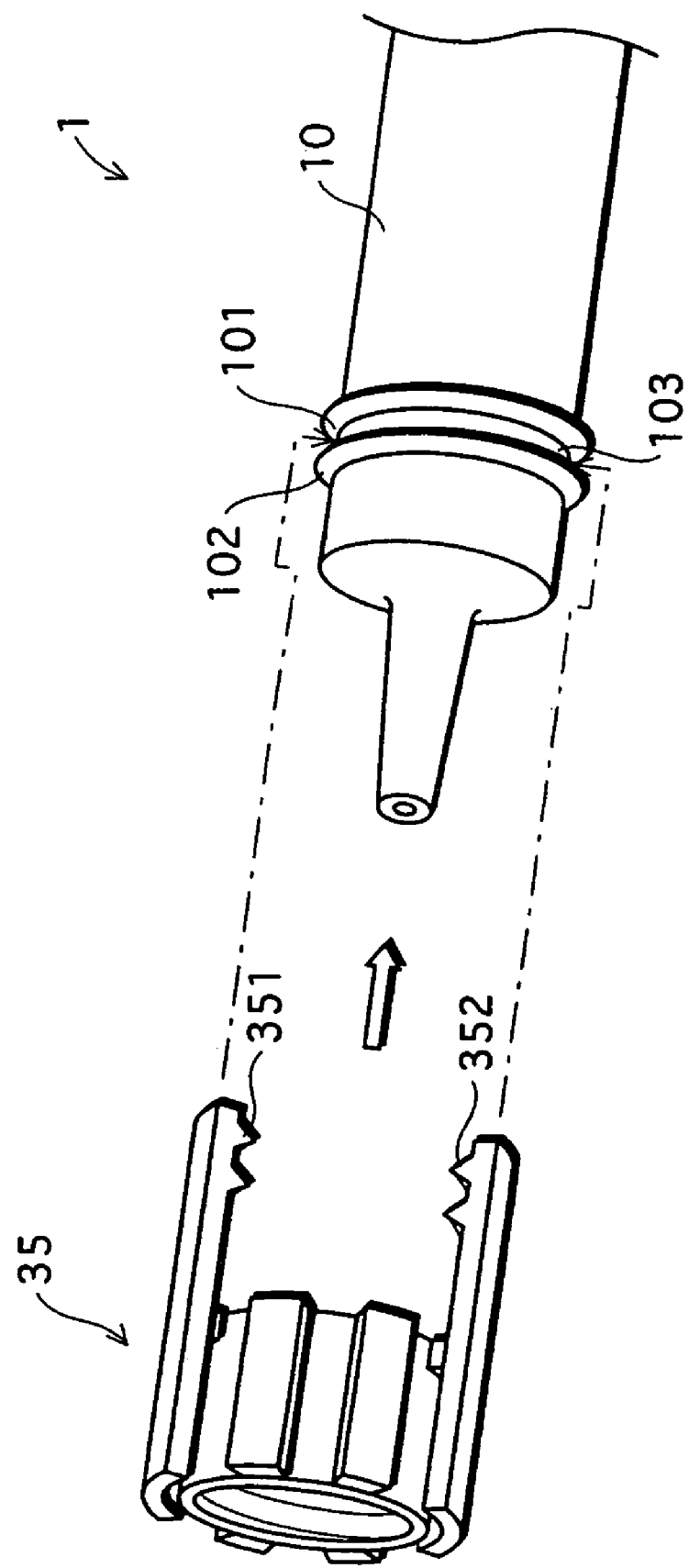
FIG. 18 shows a structure of a locknut and a prefilled syringe of Embodiment 9.

As to Embodiment 9 shown in FIG. 18, although the structure of the syringe body 10 is substantially similar to that of Embodiment 6, a locknut 35 has a slightly different structure. Embodiment 9 is characterized by projection sets 351 and 352, each of which includes multiple projections, formed on the inner sides of the tip ends of arms 36 and 37, respectively. Here, in the respective sets 351 and 352, the projections are provided with a predetermined distance therebetween.

With using the syringe body 10 having the lockout 35 also, Embodiment 9 is able to achieve an equivalent effect to that of Embodiment 6. Especially since the multiple projections of the sets 351 and 352 are fitted with the syringe body 10, Embodiment 9 allows for a more reliable fixation of the syringe 1 and locknut 35.

Additional Particulars Regarding Embodiments 6 through 9

Although the prefilled syringe 1 of the present invention has been explained with an example in which the needle hub 60 is attached after the locknut 30 being detached, the present invention is not limited to that case. Instead of a needle hub, a tubelike luer or a tube may be used. It is effective to attach, from the top, a cap or the like to the prefilled syringe 1 with a needle hub attached thereto so as to protectively cover the needle hub and needle tube for the purpose of avoiding accidental pricking. As such a cap, one similar to a cap for a vial container can be used.

Each embodiment described above discloses a structural example of a locknut having a female screw formed therein. However, the present invention is not confined to this structure, and the prefilled syringe 1 may be appropriately connected to the port of a line system using a discontinuous thread, a cup joint, or another structure.

In addition, although each embodiment above describes a structural example of a lockout having two arms, the present invention is not limited to the number of arms. Further more, instead of the arms, a tubular extension may be formed by extending the cylindrical body of the locknut in the axial direction, and projections may be provided on the inner side of the extension. In this case, it is desirable that the locknut and syringe be engaged with each other by not fitting engagement, but screwing engagement in view of the elastic deformation properties of the locknut.

The luer part of the syringe used in the present invention does not necessarily have a circular cross section, and may have a rectangular, elliptic or triangle cross section, for example. Note however that, in this case, a port and a needle hub matching the shape of the luer part have to be employed.

In addition, the present invention may have a structure in which multiple arms are provided that extend from the outer circumference of the top face portion positioned at the base of the luer part, and are engaged with the convex portion formed on the outer surface of the locknut. In this case, the structure is designed so that each arm is detached from the locknut by applying external forces to the syringe body in a direction different from the axial direction.

10. Embodiment 10

10-1. Overall Structure of Prefilled Syringe

Figure 19:
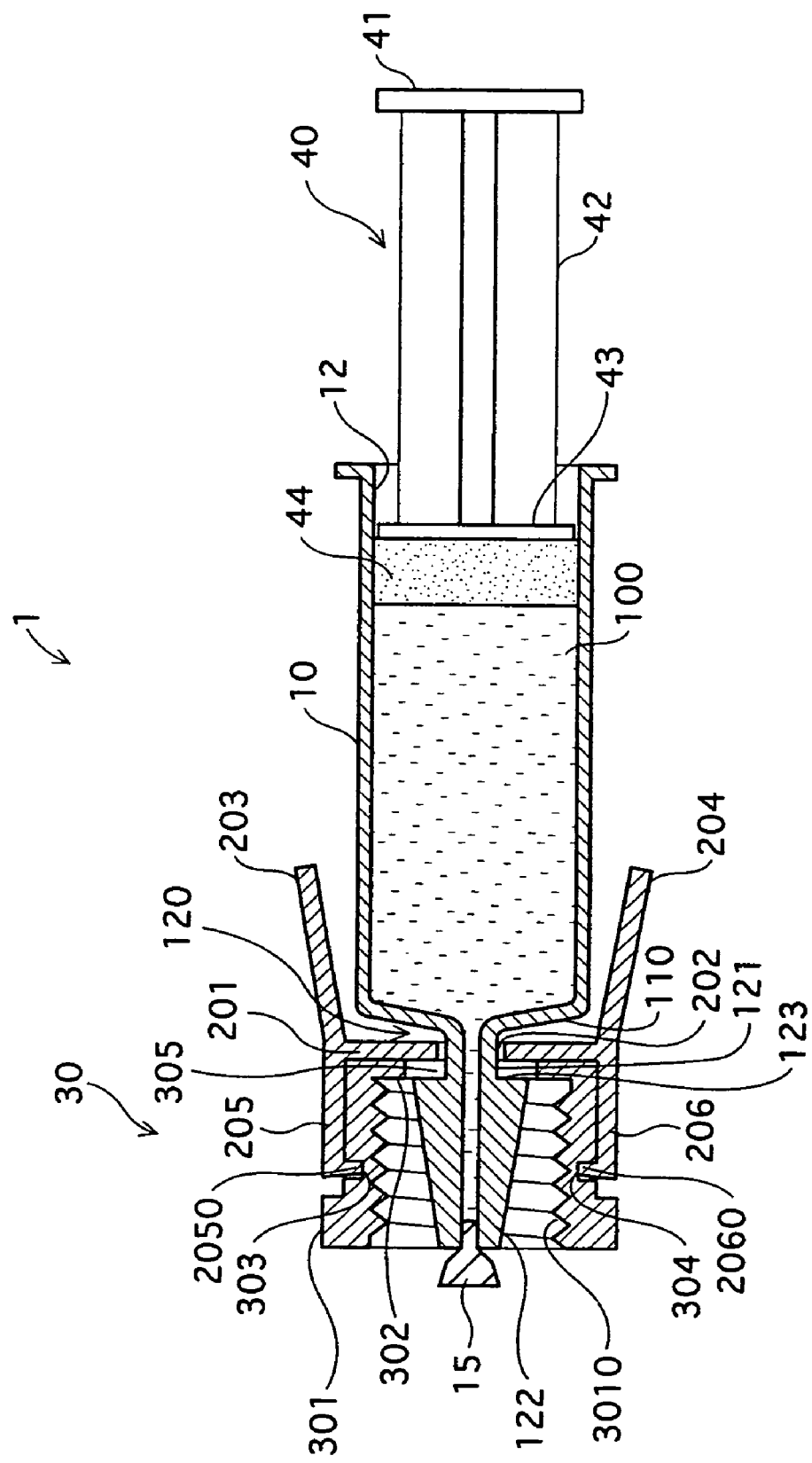
FIG. 19 is a cross sectional view showing a prefilled syringe and a locknut of Embodiment 10.

FIG. 19 is a cross sectional diagram showing structures of a prefilled syringe and a connector (locknut) according to Embodiment 10. For convenience of explanation, the plunger 40 is shown here in normal lateral view rather than in cross section.

The prefilled syringe 1 shown in FIG. 19 may comprise the syringe body 10, the plunger (also referred to as a piston) 40 and the like.

The syringe body 10 may be a tubular body formed by injection molding a material with high chemical resistance, such as polyethylene, polypropylene, polycarbonate or polyvinyl chloride. The tip end of the syringe body 10 is sealed by the top face portion 110, and the luer part 120 juts out from the center of the top face portion 110.

On the other hand, the opening 12 is formed at the posterior end of the syringe body 10. Although the luer part 120 is formed by drawing to basically give a tapered shape, the stepped portion 123 is provided in a part of the tapered shape, which thereby forms the luer base portion 121 having a smaller diameter and the luer tip portion 122 located on the tip side of the luer part 120 and having a larger diameter. A fixture 20, to be hereinafter described, is fitted to the stepped portion 123. In addition, the luer tip portion 122 is formed in a tapered shape in compliance with ISO6/100 so that the regular needle hub 20 can be attached thereto easily. In FIG. 19, the cap 15 is attached to the tip of the luer part 120.

In the following description, the longitudinal direction of the syringe body 10 is referred to as an "axial direction" while a direction perpendicular to the axial direction is referred to as a "radial direction".

The plunger 40 is made of a resin material with high chemical resistance, similarly to the syringe body 10, and includes the plunger body 42 having a cruciform cross sectional shape for the purpose of reinforcement, at each end of which are formed disk-shaped end pieces having main surfaces in the radial direction. One of the end pieces is the pressing end portion 41 to be pressed by the user with a thumb, and the other end piece is the head portion 43 that is inserted inside the syringe body 10 in the axial direction.

The packing 44 is provided at the tip of the head portion 43 in a manner to make tight contact with the internal wall of the syringe body 10. Here, medication 100 is held in the syringe body 10, which is internally sealed by the packing 44 and the cap 20.

When using the prefilled syringe 1 having such a structure, the user removes the cap 20 to enable discharge of the medication 100. As the user pushes the pressing end portion of the plunger 40 into the syringe body 10 with a thumb, the medication 100 is discharged from the tip of the luer part 120 according to the depressed amount of the plunger.

10-2. Structures of Fixture and Locknut

The prefilled syringe 1 of Embodiment 10 is constructed such that the locknut 30, which is a connector easily detachable from the syringe body 10, is inserted onto the luer part 120 in the axial direction and attached thereto so as to be engaged with the fixture 20 positioned at the stepped portion 123. The locknut 30 is used in the medical field as a connection implement for connecting the prefilled syringe 10 to a fixed connection port of a transfusion line system or blood collection line system. Note that, here, the prefilled syringe 1 is adopted as a syringe for engaging with the locknut 30; however, the present invention may be applied to syringes other than prefilled syringes.

The fixture 20 is formed by injection molding a resin material with mechanical strength and appropriate elasticity. As shown in the assembly drawing of FIG. 20, the fixture 20 comprises: a platy fixture body 201 having an insertion hole 202; two platy arms 205 and 206 extending in one direction from the periphery of the fixture body 201; and two platy levers 203 and 204 also extending in the opposite direction from the periphery of the fixture body 201.

The diameter of the insertion hole 202 of the fixture body 201 is slightly smaller than that of the luer tip portion 122 of the luer part 120, but larger than that of the luer base portion 121. The fixture 20 is inserted onto the luer part 120 through the insertion hole 202 and then forcedly shifted to fit at the luer base portion, and whereby the stepped portion 123 abuts on the periphery of the insertion hole 202 and the fixture 20 is held so as to be not easily separated from the luer part 120. In order to favorably hold the fixture body 201 by "forced fit" at the stepped portion 123 using the insertion hole 202, it is desirable to make the insertion hole 202 have the minimum possible diameter that enables the luer base portion 121 to pass therethrough. In addition, the diameter enabling the "forced fit" varies according to the elasticity of the material of the fixture body 201, and therefore it is desirable to take into account the size of the luer base portion 121 and the material properties of the fixture 20 for designing the insertion hole 202.

The two arms 205 and 206 extend in the syringe axial direction, and projections 2050 and 2060, each having a triangular cross section, are formed inside the tip ends of the arms 205 and 206. Note that the cross-sectional shape of the projections 2050 and 2060 may be rectangular, semicircular, or other forms.

Figure 20:
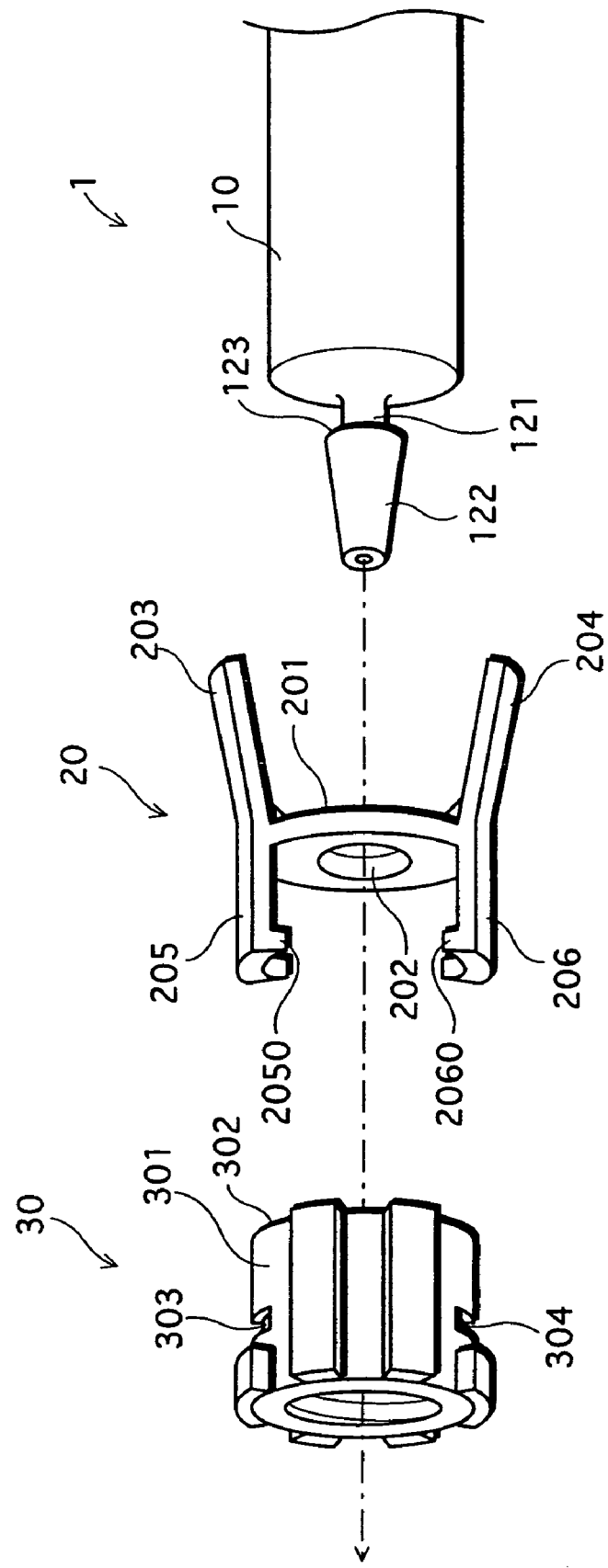
FIG. 20 is an assembly drawing of the prefilled syringe, a fixture and the lockout of Embodiment 10.

The two levers 203 and 204 and the arms 205 and 206 are formed swayable so that each of these sets warps away from the syringe axis, with portions thereof adjacent to the fixture body 201 being fixed points and their tip ends spreading like open tweezers. As shown in FIG. 20, the levers 203 and 204 are formed to be symmetric with the two arms 205 and 206, respectively, around the fixed points of the fixture 201, and thereby when the levers 203 and 204 are pressed, the arms 205 and 206 open up, warping away from the syringe axis. This mechanism is for detaching the locknut 30. Note that it is desirable to use a material having appropriate elasticity (polypropylene, for example) for the fixture 20 in order to favorably design the insertion hole 202 and achieve the swayable mechanism.

The locknut 30 has a cylindrical shape having a bottom, and is formed by injection molding a resin material with high mechanical strength. A screw thread is cut on the internal surface of the lateral side portion (outer surface) 301, which corresponds to the cylindrical part of the locknut 30, to thereby form the female screw 3010 in compliance with, for example, ISO594-2. The female screw 3010 engages with the male screw to be hereinafter described.

An insertion hole 305 is provided on the main surface portion 302 that is the bottom of the locknut 30. The insertion hole 305 is formed to have a diameter at least larger than that of the luer tip portion 122 so that the entire luer part 120 of the prefilled syringe 1 is inserted thereto with clearance therebetween. Concave portions 303 and 304 are formed on the lateral side portion 301 of the lockout. These concave portions 303 and 304 have, for example, a rectangular cross section, and their locations and sizes are determined so that the concave portions 303 and 304 can engage with the projections 2050 and 2060 provided on the arms 205 and 206 of the fixture 20.

10-3. Engagement of Syringe and Locknut

As a characteristic of Embodiment 10, the engagement of the syringe body 10 and locknut 30 using the fixture 20 is described with reference to the assembly drawing of FIG. 20. Note that FIG. 20 shows an operation of attaching the fixture 20 to the luer part 120, and this operation takes place only when the fixture 20 is attached to the syringe body 10 for the first time. Once the luer part 120 and fixture 20 are attached to each other, the present invention does not require to detach them again.

Figure 22:
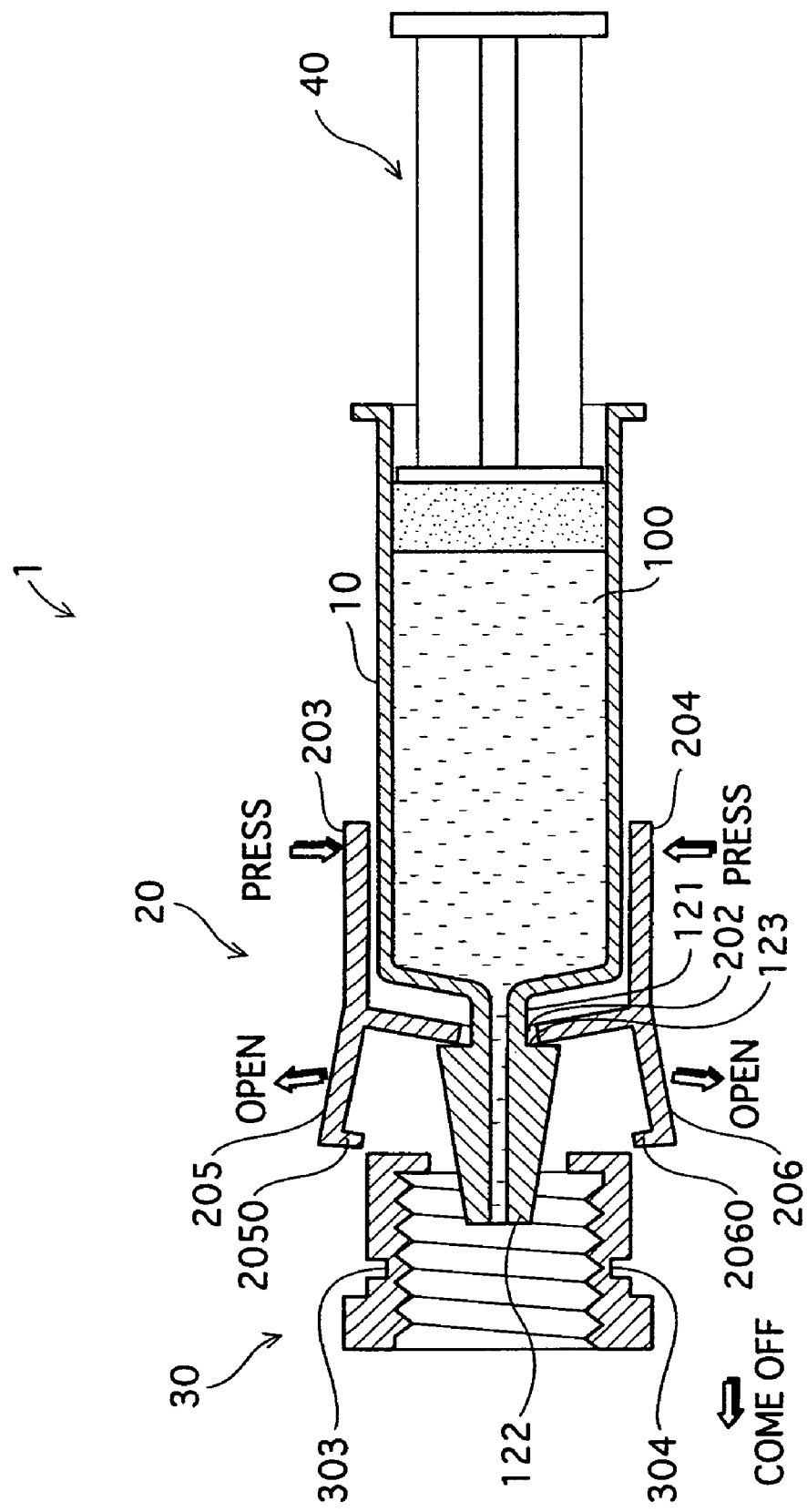
FIG. 22 shows the state of the locknut being disengaged from the fixture of Embodiment 10.

As to the locknut 30 having the above structure and the fixture 20 fitted with the luer base portion 121 of the luer part 120 and held at the stepped portion 123, the user first presses the levers 203 and 204 by gripping them with fingers so as to open the tip ends of the arms 205 and 206 away from the axial direction, as shown in FIG. 22. While this state is maintained, the user inserts, into the insertion hole 305 along the axial direction, the luer tip portion 122 of the luer part 120 to which the fixture 20 is attached. At this point, since the insertion hole 305 has a sufficiently large diameter as compared to the luer tip portion 122 of the luer part 120, the user can smoothly insert the luer part 120 into the lockout 30. Note that the size of the insertion hole 305 may be set so that the insertion hole 305 is slidable over the luer tip portion 122 to some degree, and then a device preventing the locknut 30 from easily disengaging from the luer tip portion 122 may be provided.

After shifting the lockout 30 sufficiently to the luer part 120 side, as the second step, the user checks on the relative positions of the concave portions 303 and 304 provided on the lockout's lateral side portion 301 and the projections 2050 and 2060 of the fixture 20, and releases the pressure applied on the levers 203 and 204. Herewith, the projections 2050 and 2060 of the arms 205 and 206 engage with the concave portions 303 and 304 of the locknut 30, and whereby the locknut 30 is favorably held on the syringe body 10 by means of the fixture 20.

On the other hand, the fixture 20 and locknut 30 can, after being engaged with each other, be again detached by performing a predetermined operation (i.e. applying an external force an the fixture 20 in a direction different from the syringe axial direction) in the following manner. That is, when the user presses the levers 203 and 204 while grasping the fixture 20, the projections 2050 and 2060 of the arms 205 and 206 are released from the concave portions 303 and 304 of the locknut 30 according to so-called "the principle of leverage", and in this state of things, the user can pull the locknut 30 out along the axial direction. This operation can be performed in a reversible and simple fashion (for example, in one hand), and the user is therefore able to easily attach the locknut 30 to the prefilled syringe 1 when required, and detach the locknut 30, when not required, to thereby use the prefilled syringe 1 alone.

Figure 21:
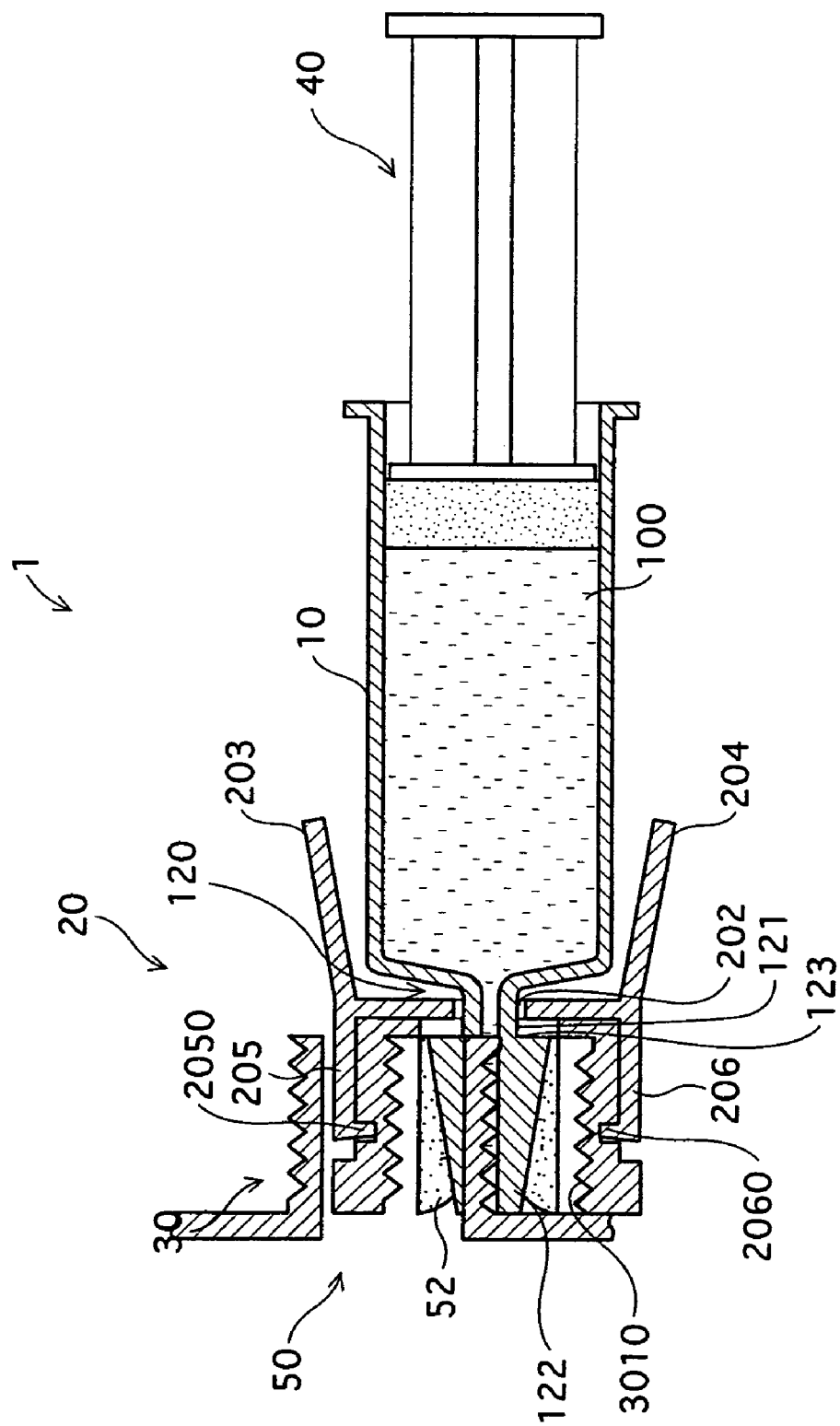
FIG. 21 shows the way to connect the prefilled syringe of Embodiment 10 to the fixed connection port.

FIG. 21 is a cross sectional view showing that the prefilled syringe 1 may be connected, using the locknut 30, to the fixed connection port 50 of a transfusion line system. The male screw of the port 50 is screwed into the female screw 3010 of the locknut 30 shown in FIG. 21, and herewith the luer tip portion 122 of the luer part 120 of the prefilled syringe 1 is in close contact with the packing 52 provided inside the port 50 and is inserted into the transfusion line. The locknut 30 is tightly engaged with the syringe 1 by the projections 2050 and 2060 of the arms 205 and 206 and the concave portions 303 and 304 of the locknut 30 so that the prefilled syringe 1 does not come apart from the port 50 along the axial direction even if some degree of tension is applied to the prefilled syringe 1. As a result, the user is able to leave the prefilled syringe 1 connected to the port 50 over a long period of time and deliver a required amount of medication 100 to the inside of the port 50 by safely pushing the plunger 40 into the syringe body 10.

Figure 23:
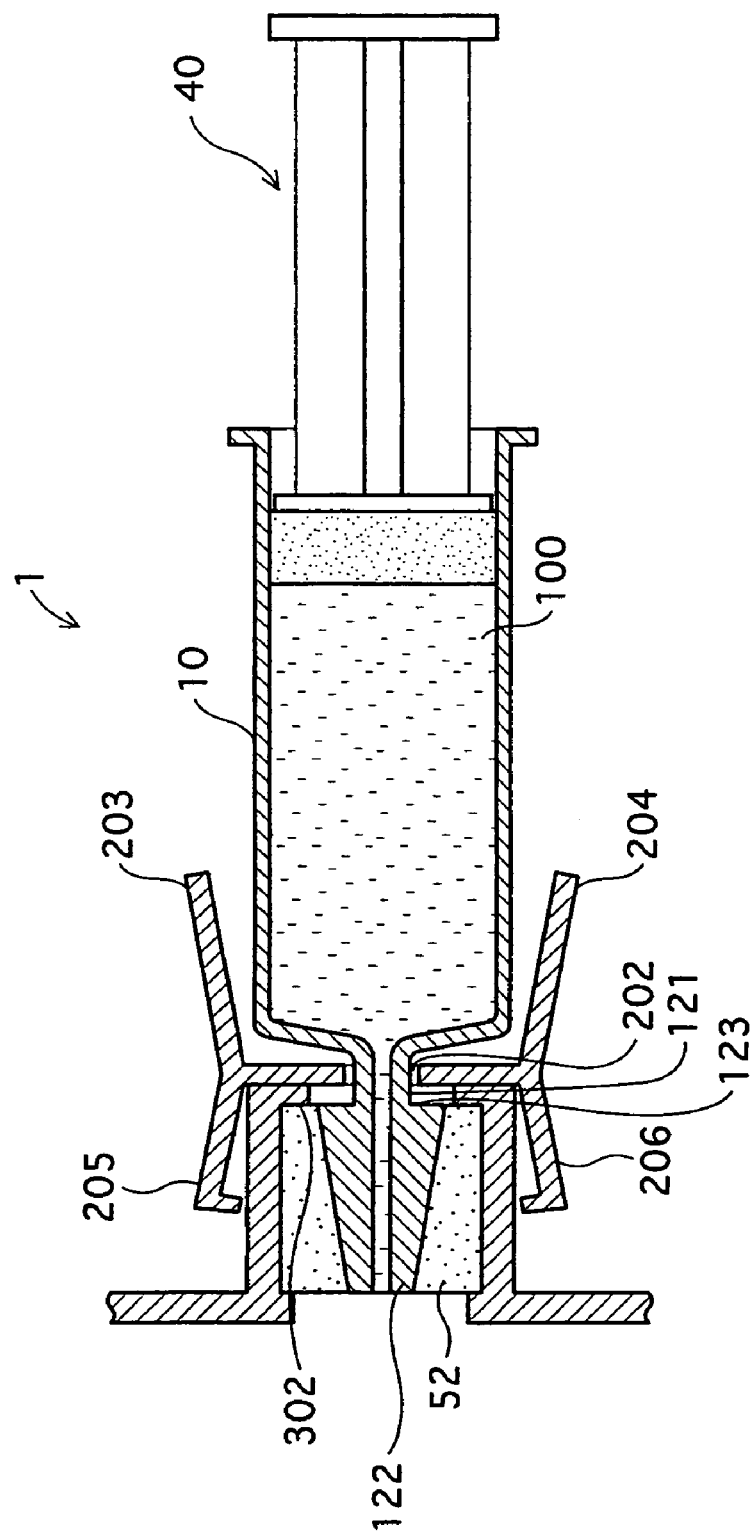
FIG. 23 shows the prefilled syringe of Embodiment 10 connected to the direct connection port.

On the other hand, FIG. 23 is a cross sectional view showing that the prefilled syringe 1 is connected to the direct connection port 500 of a transfusion line system after the locknut 30 has been detached from the prefilled syringe 1. With the prefilled syringe 1 from which the locknut 30 has been detached, no obstacle exists around the luer tip portion. It is therefore possible to, without the interference of the locknut 30, achieve a suitable connection between the prefilled syringe 1 and the port 500 by properly and tightly holding the luer tip portion 122 with the packing 52 in the port 500. As a result, with the direct connection port 500 also, the user is able to leave the prefilled syringe 1 connected to the port 500 over a long period of time and deliver a required amount of medication 100 to the inside of the port 50 by safely pushing the plunger 40 into the syringe body 10.

Figure 24:
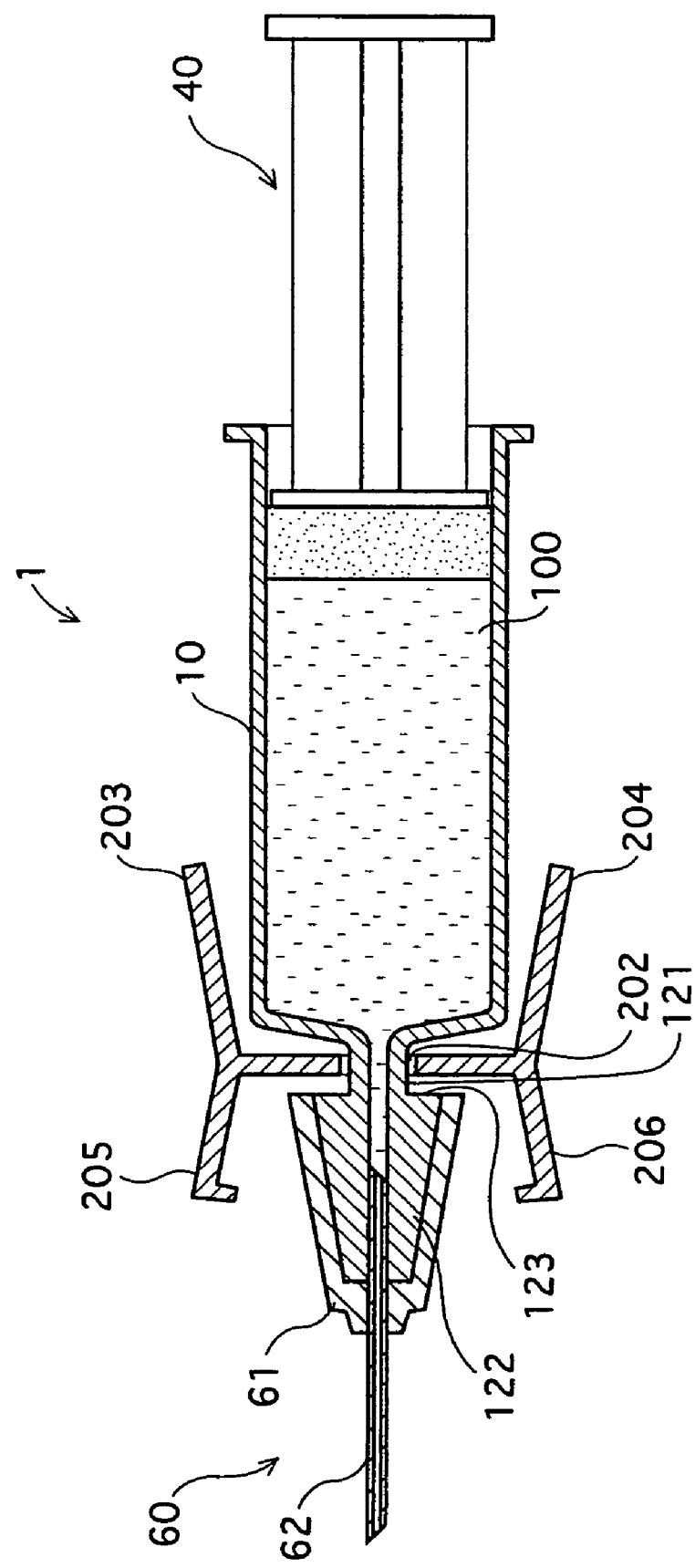
FIG. 24 shows the prefilled syringe of Embodiment 10 to which a conventional needle hub is attached.

FIG. 24 is a cross sectional view showing that the needle hub 60 is attached to the luer tip portion 122 after the locknut 30 has been detached from the prefilled syringe 1. The needle hub 60 has a structure in which the socket portion 61 composed of a resin material and formed to match the shape of the luer tip portion 122 holds the needle tube 62 which is an injection needle. With the conventional prefilled syringe in which the locknut is fixed and cannot be detached therefrom as shown in FIG. 43, the locknut obstructs the view of the user and makes it difficult to visually determine the positioning of the luer and the needle hub, thereby creating the danger of the user mistakenly pricking himself/herself and caning into contact with infectious material. However, Embodiment 1 solves such a conventional problem since allowing for easy Observation of the positional relationship around the luer between the levers 205 and 206 which spread like open tweezers from the fixture 20.

Other Embodiments

Note that although in Embodiment 10 the locknut 30 is attached to the syringe using the arms 205 and 206 and concave portions 303 and 304, the following embodiments are also within the scope of the present invention.

11. Embodiment 11

Figure 25:
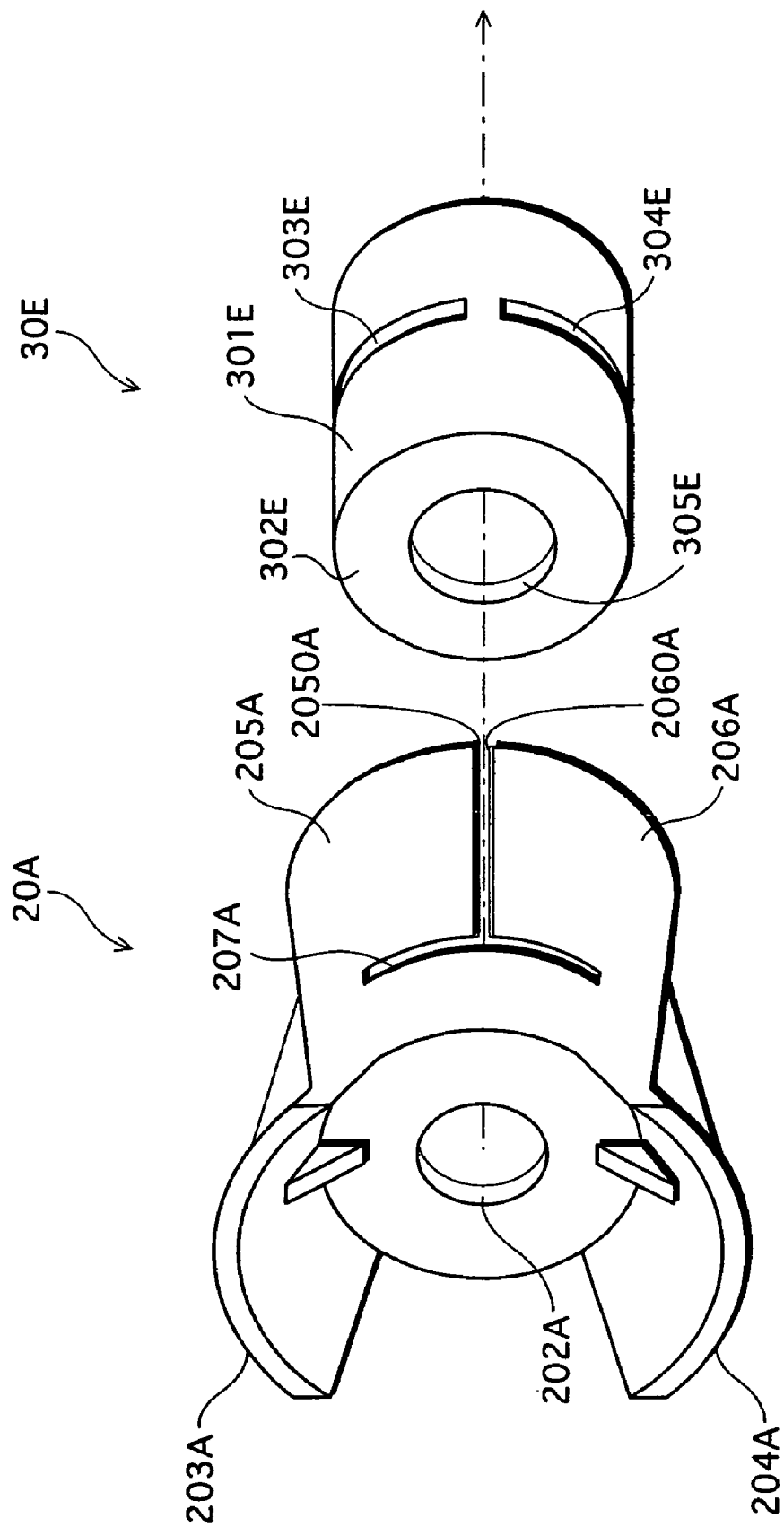
FIG. 25 shows a structure of a lockout of Embodiment 11.

In a structural example of Embodiment 11 shown in FIG. 25, slit-shaped concave portions 303E and 304E are formed on a lateral side portion 301E of a locknut 30E along the circumference thereof. On the other hand, in addition to levers 203A and 204A similar to the levers 203 and 204 of Embodiment 10, arms 205A and 206A are provided, each shaped like an arc of a semicircle in cross section. These arms 205A and 206A extend from a fixture body 20A, and a slit 207A is created on the arms 205A and 206A adjacent to the boundary between the arms 205A and 206A and the fixture body 201A. With the slit 207A, the arms 205A and 206A spread like open tweezers when the user presses the levers 203A and 204A. On the inner side of the tip ends of the arms 205A and 206A, projections 2050A and 2060A are formed to match the shape of the slit-shaped concave portions 303E and 304E.

Embodiment 11 with the fixture 20 and lockout 30 having such structures can achieve an equivalent effect to that of Embodiment 10. In addition, Embodiment 11 has a structure in which the arms 205A and 206A hold the lockout 30E in a manner to encase it, enabling more reliably attachment of the locknut 30E to the syringe 1 without any play. Furthermore, according to Embodiment 11, even if torque is applied to the locknut 30E in the radial direction while in use, the engagement of the slit-shaped concave portions 303E and 304E and the projections 2050A and 2060A favorably prevents the locknut 30A from rotating, which results in maintaining stable engagement of the syringe 1 and locknut 30E.

12. Embodiment 12

Figure 26:
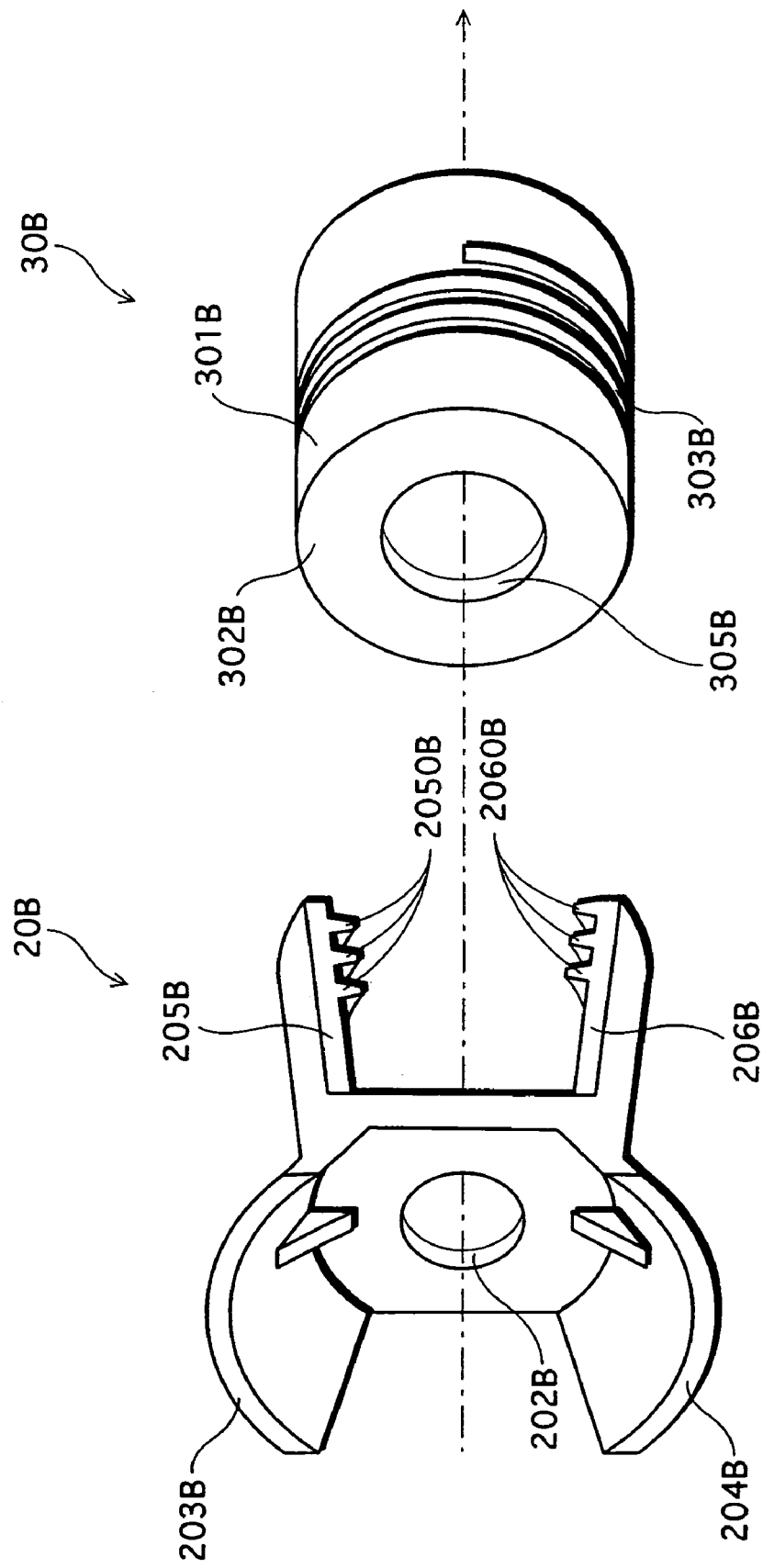
FIG. 26 shows a structure of a lockout of Embodiment 12.

In a structural example of Embodiment 12 shown in FIG. 26, a female screw portion 303B is spirally formed on a lateral side portion 301B of the locknut 30B along the circumference thereof. On the other hand, in addition to levers 203B and 204B similar to the levers 203 and 204 of Embodiment 10, arms 205B and 206B having male screw portions 2050B and 2060B made up of multiple projections are provided. The female screw portion 303B and male screw portions 2050B and 2060B are formed so that they can be screwed with each other. The arms 205B and 206B are provided so as to extend from a fixture body 201B, and spread like open tweezers when the user presses levers 203B and 204B. To attach a fixture 20B to the locknut 30B, the user spreads the male screw portions 2050B and 2060B by pressing the levers 203B and 204B, and brings the male screw portions 2050B and 2060B into contact with the female screw portion 303B provided on the external peripheral surface of the lockout 30B. Subsequently, the male screw portions 2050B and 2060B and the female screw portion 303B are screwed with each other by causing relative rotation between the fixture 20B and locknut 30B.

Embodiment 12 with the fixture 20B and lockout 30B having such structures can achieve an equivalent effect to that of Embodiment 10. In addition, according to Embodiment 12, it is possible to securely attach the locknut 30B to the syringe 1 while preventing play and unwanted rotation between the fixture 20B and locknut 30B by adjusting the degree of screwing of the male screw portions 2050B and 2060B into the female screw portion 303B (i.e. how tightly they are locked together). As a result, even if unwanted torque is applied to the locknut 30B in the radial direction while in use, the engagement of the screw portions favorably prevents the lockout 30B from rotating, which results in maintaining stable engagement of the syringe 1 and lockout 30B.

Additional Particulars Regarding Embodiments 10 through 12

Although the prefilled syringe 1 of the above embodiments has been explained with an example in which the needle hub 60 is attached after the locknut 30 being detached, the present invention is not limited to that case. Instead of a needle hub, a tubelike luer or a tube may be used. It is effective to attach, from the top, a cap or the like to the prefilled syringe 1 with a needle hub attached thereto so as to protectively cover the needle hub and needle tube for the purpose of avoiding accidental pricking. As such a cap, one similar to a cap for a vial container can be used.

The luer part of the syringe used in the present invention does not necessarily have a circular cross section, and either one of the luer tip portion and the luer base portion or both have rectangular, elliptic, or triangle cross sections. In brief, the luer tip portion must have a larger diameter than the luer base portion.

13. Embodiment 13

13-1. Structure of Connecter 1J

The following describes a structure of a connecter 1J which is a connector of Embodiment 13, with reference to FIG. 27.

The connector 1J is used to fixedly hold a syringe 5J, to be hereinafter described, on a port 61J (see FIG. 29). As shown in FIG. 27A, the connector 1J is made up of: a connector body 10J as the main body thereof; and a locknut 20J functioning as a constraint portion which constrains the shape of the connector body 10J. FIG. 27A shows that, in the connecter 1J, the connector body 10J is free from the construction of the locknut 20J.

Of the components of the connector 1J, the connector body 10J is substantially tubular with a bottom, and includes a port connecting portion 11J and a syringe connecting portion 12J which are integrally formed. The port connecting portion 11J is located on the opening side of the substantially tubular connector body 10J, and a male screw 11a for connecting with an instrument is formed on the internal surface of the tubular body. In addition, knurling with straight ridges and grooves is provided on the outer surface of the tubular body so as to prevent slippage in an operation of connecting the connector 1J to an instrument.

The syringe connecting portion 12J is positioned, within the connector body 10J, at the bottom face thereof and part of the lateral wall adjacent to the bottom face. The bottom-face part of the syringe connecting portion 12J is divided by a slit 13J into two, up and down halved an upper bottom member 121J and a lower bottom member 122j—in the y direction in the figure. The halved bottom members 121J and 122J are structured so that the slit 13J therebetween is opened and closed according to the constraint force exerted by the locknut 20J onto the connector body 10J. A single female screw 12a discontinued by the slit 13J is formed on the outer surface of the syringe connecting portion 12J.

Figure 27B:
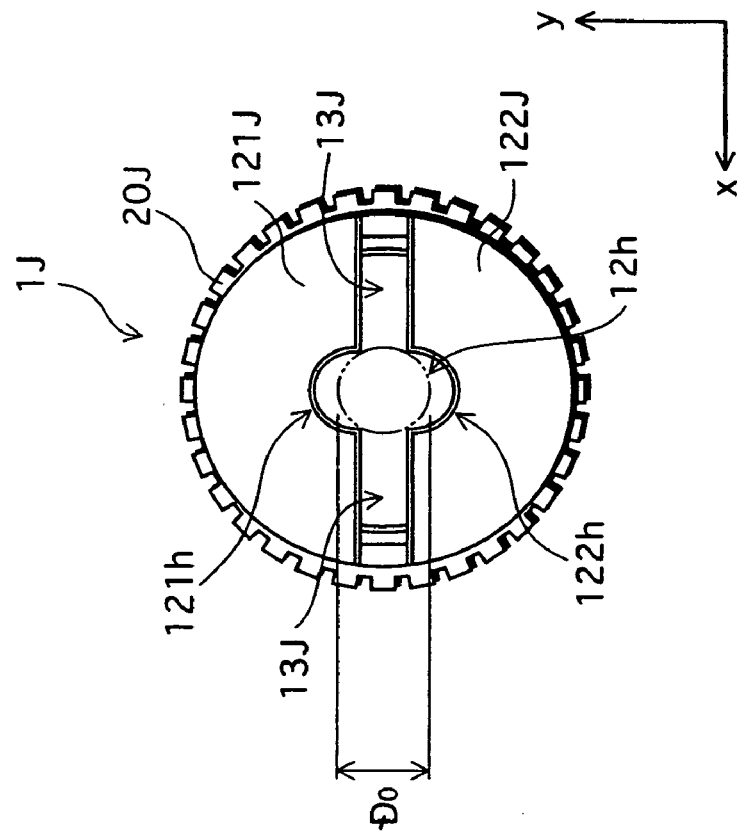
FIG. 27B is a front view of the connector 1.
Figure 27A:
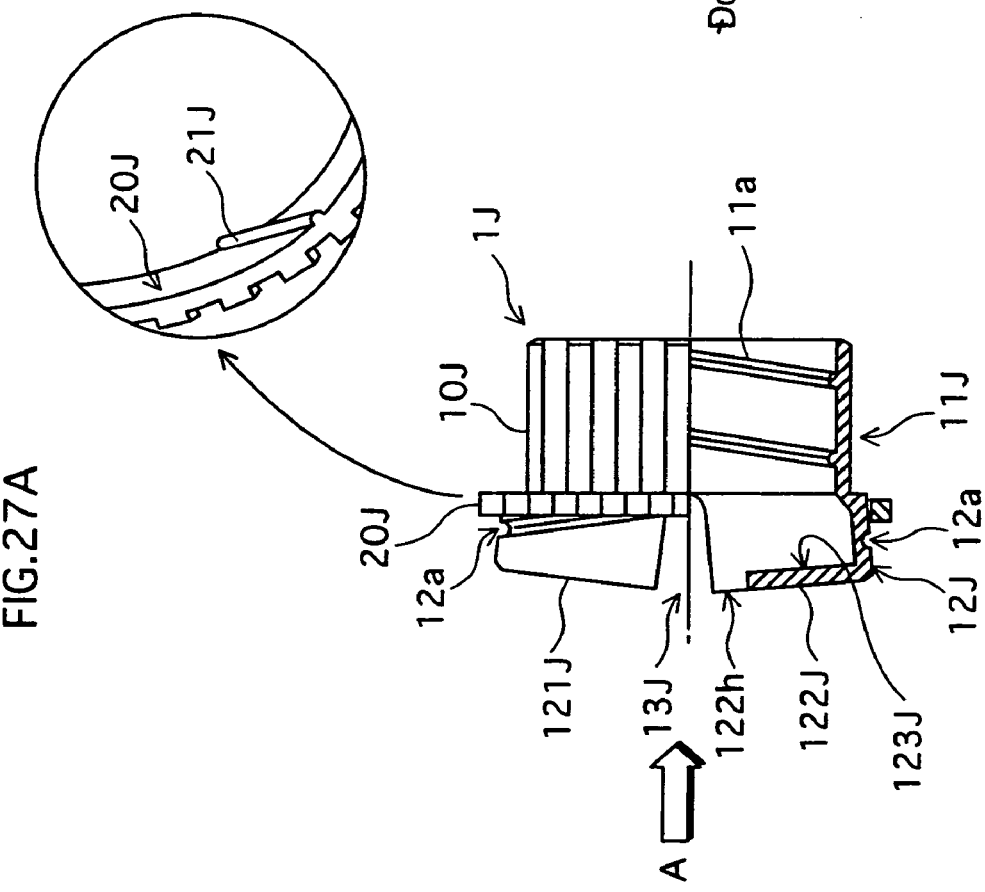
FIG. 27A is a lateral side view (with a partial cross sectional view) of a connector 1 of Embodiment 13.

As shown in FIG. 27B, the upper and lower bottom members 121J and 122J divided by the slit 13J into up and down halves in the y direction respectively have a petal-like shape, and swing in the y direction in the figure when no constraint force is exerted by the locknut 20J. Formed on the respective bottom members 121J and 122J are semicircular cutouts 121h and 122h. The chords of the cutouts 121h and 122h correspond to the lines extending from the edges of the bottom members 121J and 122J exposed to the slit 13J. In the state shown in FIG. 27B, the cutouts 121h and 122h oppose each other across a space, forming an oval shape. Here, a hypothetical inscribed circle 12h of the cutouts 121h and 122h has a diameter of $\phi D0$.

Referring back to FIG. 27A, the lockout 20J is placed to encircle the periphery of the syringe connecting portion 12J in the connector body 10J, and a male screw 21J is provided on the internal peripheral surface as shown in the closeup in the figure. The male screw 21J is to be screwed with the female screw 12a formed on the outer surface of the syringe connecting portion 12J in the connector body 10J. In addition, on the outer peripheral surface of the locknut 20J, knurling, similar to the one provided on the outer surface of the port connecting portion 11, is performed on the outer peripheral surface of the locknut 20J to thereby prevent slippage. When the locknut 20J is positioned, in the x direction, to the right of the syringe connecting portion 12J as shown in FIG. 27, the syringe connecting portion 12J spreads like open tweezers toward the bottom side. Herewith, the cutouts 121h and 122h form an oval shape as described above.

13-2. State-changeable Mechanism of Connector 1J

The following describes a state-changeable mechanism of the connector 1J having the above-mentioned structure.

In FIG. 27A, the locknut 20J is located, in the x direction, on the rightmost side of the syringe connecting portion 12J in the connector body 10J. In this configuration, the locknut 20J does not apply constraint force to the syringe connecting portion 12J.

When the locknut 20J in the configuration shown in FIG. 27A is shifted, in the x direction, to the left of the syringe connecting portion 12J as being screwed into the female screw 12a, the syringe connecting portion 12J becomes subject to constraint force exerted by the locknut 20J in the direction that the slit 13J becomes narrowed—i.e. in the direction that the space between the petal shaped bottom members 121J and 122J becomes narrowed. When the locknut 20J has been shifted to the vicinity of the bottom, the shape of the syringe connecting portion 12J that previously spread like open tweezers has been transformed to be substantially tubular. With the transformation, the space between the cutouts 121h and 122h narrows, and the diameter of the inscribed circle 12h is also reduced to less than the diameter $\phi D0$.

It is preferable that the connector body 10J be made of a material having elastic properties (e.g. a resin material) in consideration for repetitive attachment and detachment. Although the syringe connecting portion 12J changes its shape under the constraint force of the locknut 20J, the transformation is performed within the elastic range of the material constituting the connector body 10J. Accordingly, the syringe connection portion 12J returns to the state shown in FIGS. 27A and 27B without any deformation once the constraint force of the locknut 20J is removed.

Thus, the connector 1J has a mechanism that the space between the cutouts 121h and 122h on the bottom members 121J and 122J widens and narrows simply by tightening and loosening the lockout 20J. This mechanism is reversible and can be operated repeatedly.

The general structure of a syringe 5J is described with reference to FIG. 28.

Figure 28A:
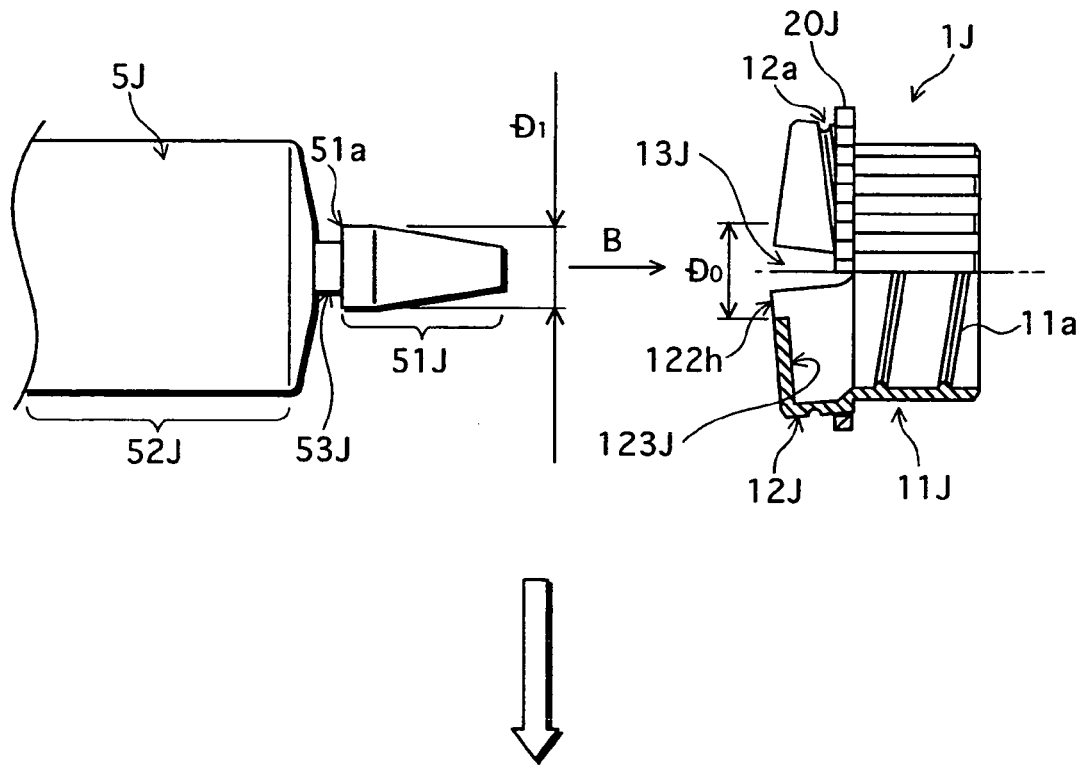
FIG. 28A is a lateral side view (with a partial cross sectional view) of the connector 1 before the connection with a syringe 5 of Embodiment 13.

The syringe 5J, part of which is shown in FIG. 28A, is a prefilled syringe, and a luer part 51J juts or extends out at the right-hand end of a syringe body 52J. Formed on the base side of the luer part 51J is a neck portion 53J having a reduced diameter. Although no illustration is given, the syringe 5J includes a plunger, a packing and the like, and the tubular part of the syringe body 52J is filled with the liquid medication.

Among the components of the syringe 5J, the luer part 51J has a tapered shape and a maximum outer diameter of $\phi D1$. The outer diameter $\phi D1$ is smaller than the diameter D0 of the inscribed circle 12h of the connector 1J in the open state shown in FIG. 27, i.e. ($\phi D1 < \phi D0$). The neck portion 53J on the base side of the luer part 51J is tubular with a diameter smaller than the diameter $\phi D1$.

A step is made in a part of the luer part 51J close to the neck portion 53J so as to form an engaging portion 51a.

The connection of the above-mentioned syringe 5J and connector 1J are described next also with reference to FIG. 28.

As shown in FIG. 28A, the lockout 20J of the connector 1J is set back, within the syringe connecting portion 12J, to the side closest to the port connecting portion 11J, and whereby the connector body 10J is kept free from the constraint force of the lockout 20J in the radial direction, similar to the case of FIG. 27. The luer part 51J of the syringe 5J is inserted toward the inscribed circle 12h (not shown in FIG. 28) of the cutouts 121h and 122h of the connector 1J in this state (arrow B). Here, the maximum outer diameter $\phi D1$ of the luer part 51J and the diameter $\phi D0$ of the inscribed circle 12h satisfy $\phi D1 < \phi D0$, which thereby allows for smooth insertion of the luer part 51J.

The insertion of the luer part 51J into the connector 1J is done when the neck portion 53J reaches an inner bottom surface 123J of the connector 1J. While the center of the syringe 5J in the radial direction is substantially aligned with that of the connector 1J, the locknut 20J of the connector 1J is rotated along the female screw 12a and Shifted to the left in the figure. The shifting is done when the lockout 20J substantially reaches the left end of the connector body 10J.

The female screw 12a on the outer surface of the syringe connection portion 12J is formed up to the bottom members 121J and 122J (see FIG. 1) so that the locknut 20J stops thereat.

Figure 28B:
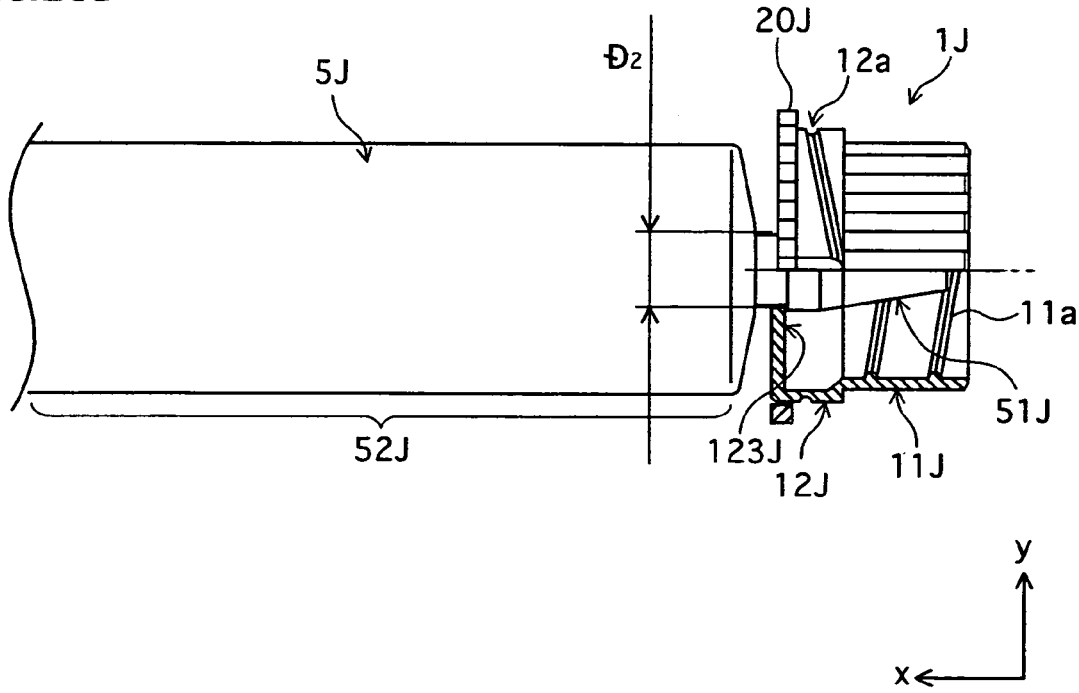
FIG. 28B is a lateral side view (with a partial cross sectional view) of the connector 1 after the connection with the syringe 5 of Embodiment 13.

As shown in FIG. 28B, in a condition where the lockout 20J has been shifted to the leftmost side of the syringe connection portion 12J, the syringe connection portion 12J that previously spread like open tweezers as in FIG. 28A closes under the constraint force exerted by the lockout 20J to be substantially tubular. With the transformation, the space between the cutouts 121h and 122h narrows, and the diameter of the inscribed circle 12h is also reduced. Then, the inscribed circle 12h formed by the cutouts 121h and 122h becomes substantially circular in the state of FIG. 28B. At this point, the diameter of the inscribed circle 12h of the connector 1 is $\phi D2$. The relationship between the diameters $\phi D1$ and $\phi D2$ is $\phi D2 < \phi D1$. Namely, in the state of FIG. 28B, the inner bottom surface 123J of the connector 1J is engaged with the engaging portion 51a of the syringe 5J, and the syringe 5J is fixedly held by the connector 1J.

Note that, in FIG. 28B, the diameter $\phi D2$ of the open hole formed by the cutouts 121h and 122h in the connector 1J is slightly larger than the outer diameter of the neck portion 53J of the syringe 5J so as to have a clearance therebetween. However, this clearance is not necessarily provided.

As has been described, the connector 1J is structured to be freely attachable to and detachable from the syringe 5J by simply handling the lockout 20J. Here, the connector 1J may be provided to the user as an accessory of the syringe 5J, or separately by itself.

In order to change a state of the syringe 5J from one in which the connector 1J is attached, as shown in FIG. 28B, to one in which the connector 1J is detached, as shown in FIG. 28A, a reverse process of the above-mentioned procedure for connecting the connector 1J may be performed.

Figure 29:
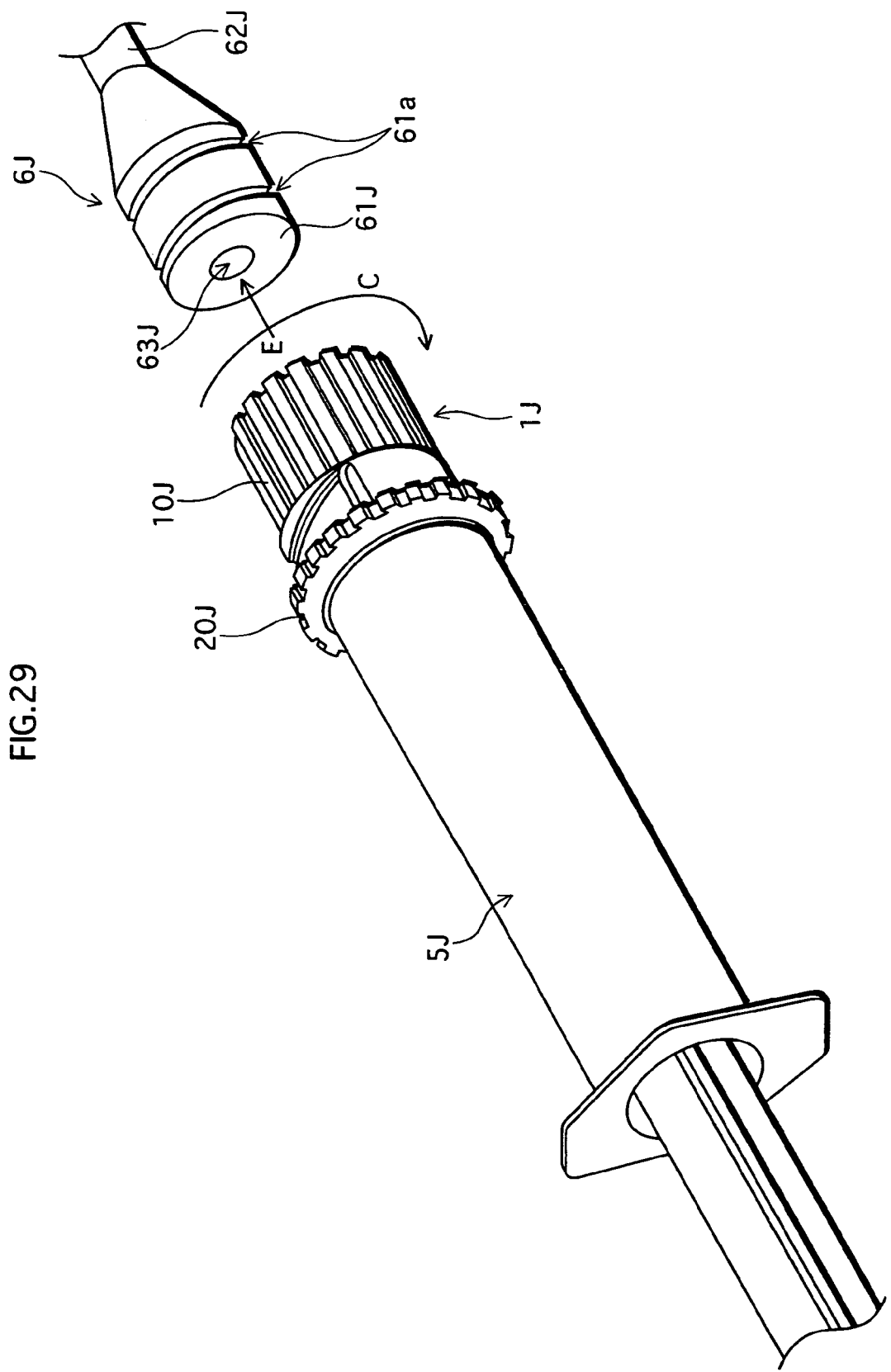
FIG. 29 is a perspective view showing a relation between the connector 1 and an extension tube 6 when they are to be connected to each other, according to Embodiment 13.

Referring to FIG. 29, the following describes a method of connecting the syringe 5J, to which the connector 1J is attached, to a port of a medical instrument in the liner-lock style. In FIG. 29, an extension tube 6J with a port attached thereto is used as an example of a connection target to which the syringe 5J is connected in the luer-lock style.

The extension tube 6J of the connection target includes the port 61J provided at one end of a tube 62J, as shown in FIG. 29. Within the port 61J, a female screw 61a is formed on the outer surface of the tubular body. The female screw 61a corresponds to the male screw 11a (not shown in FIG. 29; refer to FIGS. 27 and 28) of the connector 1J (i.e. the male screw 11a can be screwed into the female screw 61a).

On the end face of the port 61J, a hole 63J is provided in the central region. This hole 63J is connected to the inner duct of the tube 62J. The inner diameter of the hole 63J is set slightly smaller than the maximum outer diameter φD1 of the luer part 51J of the syringe 5J, and a portion of the luer part 51J of the syringe 5J can enter the inner duct through the hole 63J when the syringe 5J is connected to the extension tube 6J.

For connecting the syringe 5J and the extension tube 6J to each other, the user brings the connector 1J attached to the proximity of the luer part 51J of the syringe 5J (see FIG. 28) forward (arrow E) with respect to the extension tube 6J, and when the connector 1J and the port 61 of the extension tube 6J make contacts, the user starts rotating the connector 1J in the direction of arrow C. Herewith, the male screw 11a provided in the connector body 10J (see FIGS. 27 and 28) is progressively screwed into the female screw 61a on the port 61J of the extension tube 6J. At this point, the luer part 51J of the syringe 5J is being inserted into the hole 63J of the extension tube 6J. The male screw 11a is continuously screwed into the female screw 61a until the space between the external peripheral surface of the luer part 51J and the periphery of the hole 63J is closed.

In the above manner, the luer-lock connection of the syringe 5J and extension tube 6J is completed. Since the connection in the luer-lock style is stable, the syringe 5J and the extension tube 6J are less likely to came disengaged or loose from each other over a long period of time.

Figure 30:
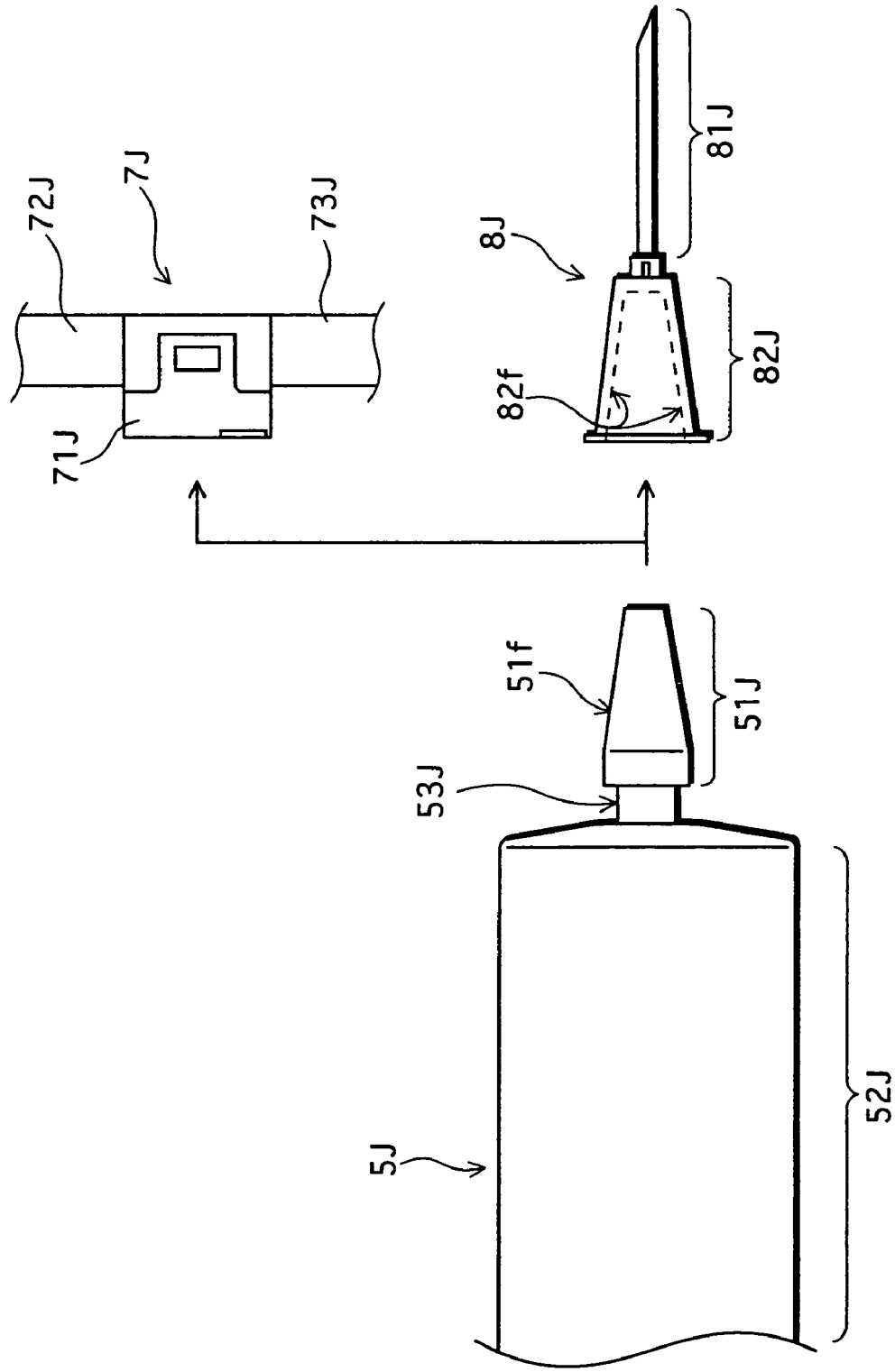
FIG. 30 is a lateral side view showing a coinfusion port 7 or an injection needle is to be connected to the syringe 5J in luer-slip style without using the connector 1, according to Embodiment 13.

Referring to FIG. 30, the following describes a method of connecting the syringe 5J to a port of a medical instrument in the luer-slip style. In FIG. 30, a coinfusion port 7J and an injection needle 8J are used as examples of connection targets to which the syringe 5J is connected.

For the connection in the luer-slip style, the syringe 5J to which the connector 1J is not attached is used, as shown in FIG. 30. As to the syringe 5J, the user may use one to which no connector is originally attached, or alternatively obtain one with the connector 1J attached thereto and use this syringe after detaching the connector 1J therefrom. The connector 1J can be readily detached according to a reverse process of the above-mentioned procedure shown in FIG. 28.

For the connection in the luer-slip style, the luer part 51J of the syringe 5J is simply inserted into a port of a connection-target medical instrument. For example, the connection of the syringe 5J to the coinfusion port 7J is completed simply by inserting the luer part 51J of the syringe 5J into a valve plug (not shown) provided in a cover body 71J. Herewith, the interior of the syringe 5J and the interior of the tubes 72J and 73J of the coinfusion port 7J are communicated to each other.

The valve plug of the coinfusion port 7J is an elastic thin film, and a slit to receive the luer part 51J is formed in a part of the valve plug. Since such matters are public knowledge, the descriptions are omitted here.

Next, for connecting the syringe 5J and the injection needle 8J to each other, a needle hub 82J of the injection needle 8J is mounted on the luer part 51J of the syringe 5J. The syringe 5J and the injection needle 8J are connected to each other when an internal peripheral surface 82f of the needle hub 82J becomes tightly attached to the external peripheral surface 51f of the luer part 51J. Although no graphic representation is given, the needle tube 81J juts out also inside the needle hub 82J, and the jutted part is inserted into an inner hole of the luer part 51J when the syringe 5J and the injection needle 8J are connected to each other. The needle hub 82J and the inner hole of the luer part 51J are tightly fitted to each other while the injection needle 8J being connected to the syringe 5J. That is, the needle hub 81J and the inner hole are designed so that the liquid medication will not leak out therefrom or bacteria will not enter therefrom.

The luer-slip connection of the syringe 5J and another medical instrument has been described by presenting two examples above. The syringe 5J of FIG. 30 does not have the connector 1J attached thereto, allowing for quick luer-slip connection.

Although, there are various medical instruments that can be connected to the syringe 5J in the luer-slip style besides the above two examples, the connection operations for those instruments are the same as Above.

Advantages of Connector 1J and Syringe 5J Having Connector 1J Attached Thereto

As has been described above and also shown in FIG. 28, the connector 1J of Embodiment 13 is attachable to and detachable from the syringe 5J by simply performing the screwing operation of the lockout 20J. Thus, in the medical practices, the user is able to readily attach and detach the connector 1J to/from the syringe 5J according to need.

Thus, since being able to attach and detach the connector 1J functioning as a connector to/from the syringe 5J if necessary, the user can use the detached connector 1J with another syringe. This results in a reduction in the cost burden on the user and allows for an excellent operational performance of the syringe 5. Furthermore, the syringe 5J can be connected to the port of another medical instrument in either the luer-slip or luer-lock style.

When connecting the injection needle 8J to the syringe 5J, the user can use the syringe 5J from which the connector 1J has been detached, as shown in FIG. 30. Thus, the syringe 5J is also effective in preventing the user from mistakenly pricking himself/herself.

Note that the connector 1J, which functions as a connector, does not have to be provided with every syringe 5J when supplied to the user, and may be singularly provided to the user instead. In such a case, the user may attach/detach the connector 1J to/from the syringe 5J according to need. Thus, the connector 1J can be attached and detached, according to the connection style of the syringe 5J with the port, at the stages of treatment and medical care in the medical practices. As a result, operating efficiency can be improved, and the number of syringe types required to be prepared in advance can be reduced.

13. Additional Particulars Regarding Embodiment 13

Although Embodiment 13 is described with an example in which the connector body 10J is fitted to the extension tube 6J by screwing the locknut 20J into the connector body 10J and thereby making the locknut 20J shift toward the connector body 10J, the present invention is not limited to the case. The same effect as that of Embodiment 13 can be achieved, for example, with a connector having, instead of the locknut 20J, a ring body with no screw provided on the internal peripheral surface thereof. Here, the connector body 10J is fitted to the extension tube 6J by sliding the ring body toward the connector body 10J.

Note that, in the case of adopting such a sliding mechanism, it is required to implement a measure that prevents the ring body from shifting back to the original position when the connector body 10J is fitted to the extension tube 6J. Fixing the ring body with a pin is an example of such a measure.

Although, in the above embodiment, the connection target is the (prefilled) syringe 5J filled with liquid medication in advance, the above operation remains the same even if a different type of syringe, other than a prefilled syringe, is used.

14. Embodiment 14

The structure of a connector 1K of Embodiment 14 which functions as a connector is described with the aid of FIG. 31.

Figure 31A:
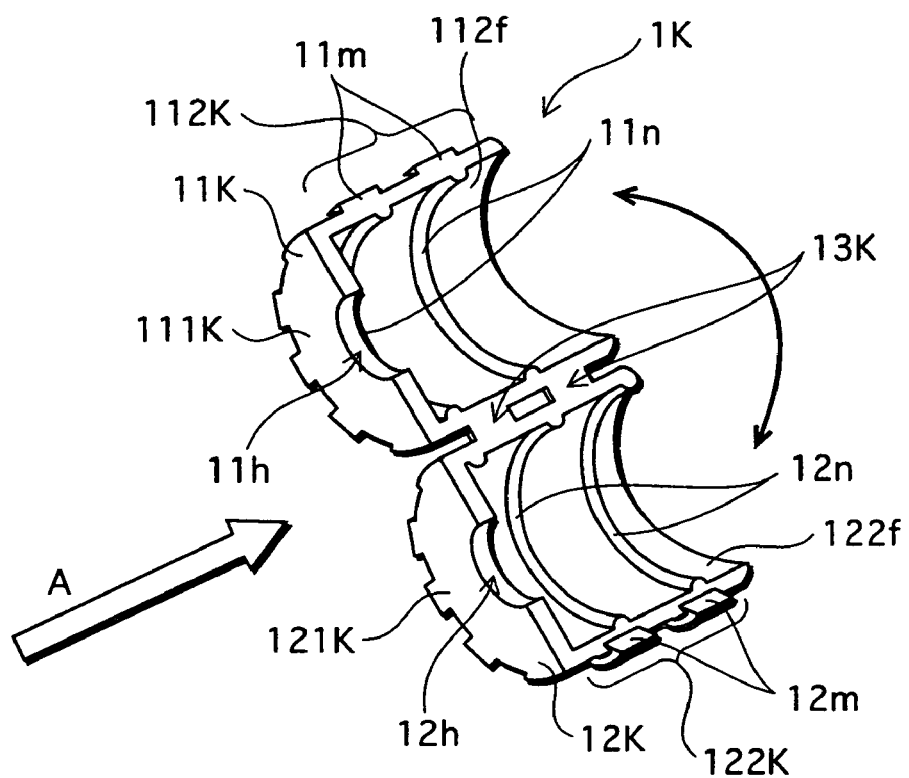
FIG. 31A is a perspective view of a connector 1 of Embodiment 14.
Figure 31B:
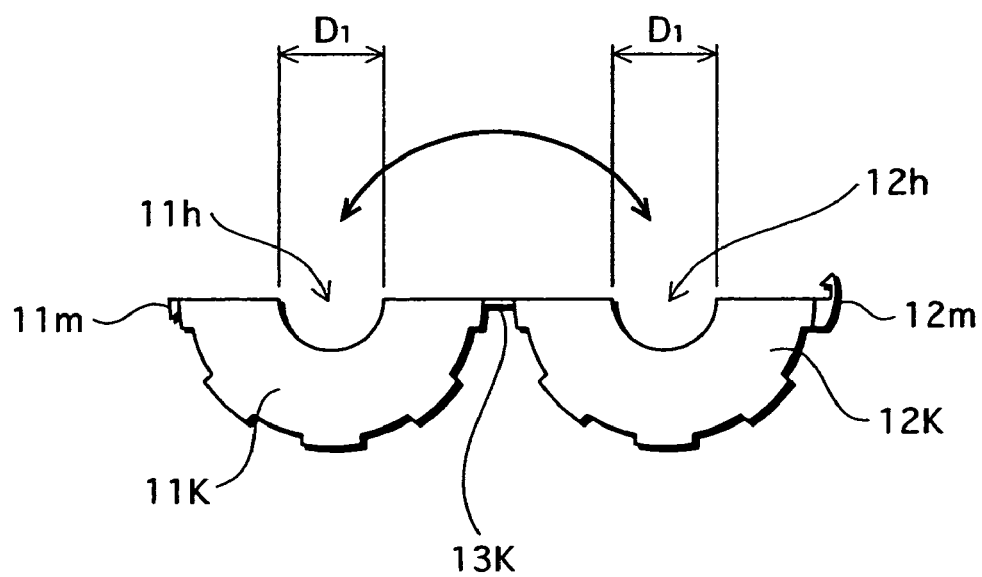
FIG. 31B is a front view of the connector 1.

As shown in FIG. 31A, the connector 1K may be made up of three components: split frames 11K and 12K; and a coupling portion 13K coupling the sides of the split frames 11K and 12K. These three components are integrally formed. Of them, the split frames 11K and 12K have a shape as if created by halving, along the axis, a hollow cylinder having a bottom. FIGS. 31A and 31B show the state where the split frames 11K and 12K are open (hereinafter, "the open position").

Each of the split frames 11K and 12K having a shape as if created by halving a cylinder hollow having a bottom includes a semicylindrical portion 112K/122K and a semicircular bottom portion 111K/121K. Formed on the semicylindrical portions 112K and 122K are sets of tabs 11m and 12m to be interlocked with each other. That is, the tabs 11m and 12m function as coupling members of the split frames 11K and 12K, and become interlocked with each other when the split frames 11K and 12K are coupled. These tabs 11m and 12m are designed so that, when once they are interlocked with each other, the coupling will not be disconnected unless an operation of pulling the tabs 12m outward is performed. Cutouts 11h and 12h are formed on the bottom portions 111K and 112K that butt against each other when the split frames 11K and 12K are engaged using the tabs 11m and 12m (hereinafter, "the closed position"). Each of the cutouts 11h and 12h has the shape of a semicircle with a chord coinciding with the halving line of the split frames 11K and 12K.

Furthermore, male screw portions 11n and 12n are provided on the inner surface of the semicylindrical portions 112K and 122K of the split frames 11K and 12K. These male screw portions 11n and 12n form a single, unbroken male screw when the split frames 11K and 12K are in the closed position.

The wall thickness of the coupling portion 13K is thinner than that of the individual split frames 11K and 12K, and the coupling portion 13K will not be dismembered after repetitive opening and closing of the split frames 11K and 12K.

The opening-and-closing mechanism of the connector 1K having the above structure is described next with the aid of FIG. 31B showing the connector 1K of FIG. 31A, viewed from arrow A.

As shown in FIG. 31B, in an anterior view, each of the split frames 11K and 12K is semicircular. When folded at the coupling portion 13, the split frames 11K and 12K face to each other, and the tabs 11m and 12m interlock with each other. Thus, the connector 1K is substantially in the shape of a cylinder having a bottom when the tabs 11m and 12m engage with each other (i.e. in the closed position).

Thus, when the split frames 11K and 12K are joined together, the cutouts 11h and 12h provided on the split frames 11K and 12K also face to each other to form a circular hole with a diameter of $\phi D1$.

Note that the split frames 11K and 12K and the coupling portion 13K, all of which are integrally formed, are preferably made of, for example, a resin material in order to achieve the above-mentioned functions.

Figure 32:
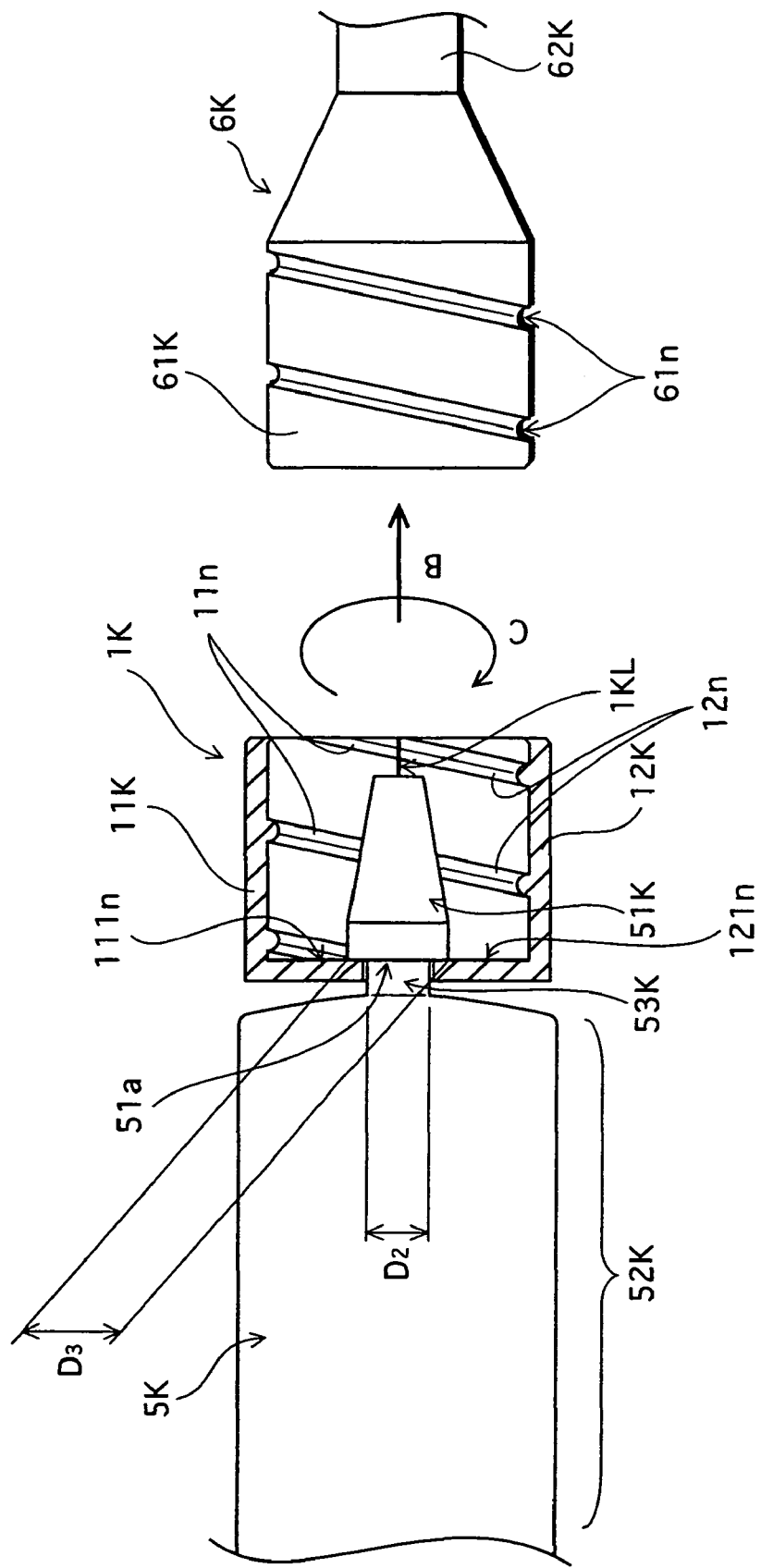
FIG. 32 is a perspective view showing a relationship between the connector 1 and an extension tube 6 when they are to be connected to each other, according to Embodiment 14.

A general structure of a syringe 5K is described with the aid of FIG. 32.

The syringe 5K, a part of which is shown in FIG. 32, is a prefilled syringe, and a luer part 51K juts out at the right-hand end of a syringe body 52K. Formed on the base side of the luer part 51K is a neck portion 53K having a reduced diameter. Although no illustration is given, the syringe 5K includes a plunger, a packing and the like, and the tubular part of the syringe body 52K is filled with the liquid medication.

Among the components of the syringe 5K, the luer part 51K has a tapered shape and a maximum outer diameter of $\phi D3$. The outer diameter $\phi D3$ is larger than the diameter $\phi D1$ of the hole formed by the cutouts 11h and 12h in FIG. 31 (i.e. $\phi D3 > \phi D1$). The neck portion 53K located on the base side of the luer part 51K is in the shape of a cylinder with an outer diameter of $\phi D2$.

A step is made in a part of the luer part 51K close to the neck portion 53K so as to form an engaging portion 51n.

The connection of the above-mentioned syringe 5K and connector 1K is described next with reference to FIGS. 31 and 32.

The luer part 51K of the syringe 5K is inserted into the connector 1K in the open position as shown in FIG. 31A and positioned in a manner that the neck portion 53K sets in the edge of either the cutout 11h or 12h. At this point, the syringe 5K and the connector 1K are maintained so that their axes substantially coincide with each other.

Next, while the syringe 5K is held not to move with respect to the connector 1K, the split frames 11K and 12K are folded at the coupling portion 13K so that the openings of the split frames 11K and 12K face to each other. The connector 1K has the shape of a cylinder having a bottom when the tabs 11m and 12m of the split frames 11K and 12K interlock with each other. At this point, the cutouts 11h and 12h form a circular hole with an inner diameter of $\phi D1$.

The syringe 5K is thus engaged, at the neck portion 53K, with the connector 1K in the closed position. That is, the maximum outer diameter $\phi D3$ of the luer part 51K is larger than the inner diameter $\phi D1$ of the hole formed by the cutouts 11h and 12h, and the engaging portion 51n of the luer part 51K is fixedly held by inner bottom faces 111n and 121n of the connector 1K. Thus, the syringe 5K and the connector 1K are connected to each other. The tabs 11m/12m of each set are provided at two locations on the split frame 11K/12K, and when these tabs 11m and 12m once interlock with each other, the connector 1K does not return to the open position unless the disengagement operation (releasing the coupling of the tabs 11m and 12m) is conducted.

Note that the male screw portions 11n and 12n, each provided on the split frame 11K/12K of the connector 1K, are designed to form one unbroken male screw across a line of junction 1KL of the split frames 11K and 12K.

Referring to FIG. 32, the following describes a method of connecting the syringe 5K, to which the connector 1K is attached, to a port of another medical instrument in the luer-lock style. In FIG. 32, an extension tube 6K with a port attached thereto is used as an example of a connection target to which the syringe 5K is connected.

The extension tube 6K being a connection target includes a port 61K provided at one end of a tube 62K, as shown in FIG. 32. Within the port 61K, a female screw portion 61n is formed on the outer surface of the tubular body. The female screw portion 61n corresponds to the male screw portions 11n and 12n of the connector 1K. Although no illustration is given, a hole is provided in the central region of the end face of the port 61K, and functions as an opening of the inner duct of the tube 62K.

The hole in the central region of the port 61K has an inner diameter slightly smaller than the maximum outer diameter φD3 of the luer part 51K of the syringe 5K. Thus, the hole of the port 61K is designed so that the luer part 51K of the syringe 5K can be inserted thereinto.

For connecting the syringe 5K and the extension tube 6K to each other, the user brings the connector 1K attached to the syringe 5K forward (arrow B) with respect to the port 61K of the extension tube 6K. When the connector 1K and the port 61K of the extension tube 6K make contacts, the user starts rotating the connector 1K in the direction of arrow C and still brings the connector 1K forward. Herewith, the male screw portions 11n and 12n provided in the split frames 11K and 12K are progressively screwed into the female screw portion 61n on the port 61K of the extension tube 6K. In parallel with the screwing operation, the luer part 51K of the syringe 5K is gradually inserted into the hole on the end face of the port 61K of the extension tube 6K. Subsequently, when the male screw portions 11n and 12n of the connector 1K are completely screwed into the female screw portion 61n of the port 61K, the syringe 5K and the extension tube 6K are connected to each other.

Since the connection of the syringe 5K and the extension tube 6K with the connector 1K therebetween (the luer-lock connection) is stable, the syringe 5K and the extension tube 6K are less likely to disengage or loose from each other over a long period of time.

Figure 33:
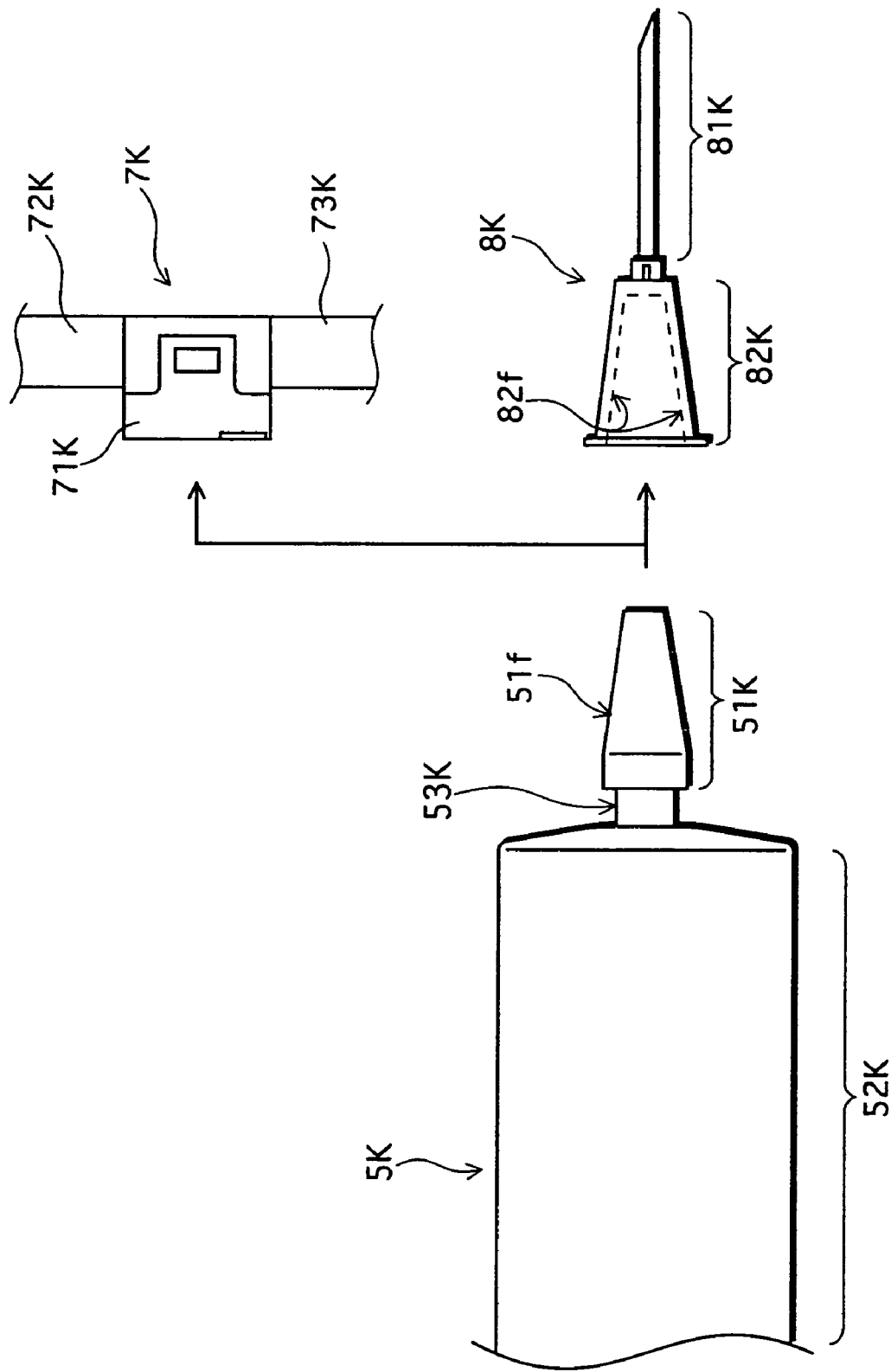
FIG. 33 is a lateral side view showing a coinfusion port 7 or an injection needle 8 is to be connected to the syringe 5K in the luer-slip style without using the connector 1, according to Embodiment 14.

Referring to FIG. 33, the following describes a method of connecting the syringe 5K and another medical instrument in the luer-slip style. In FIG. 33, a coinfusion port 7K and an injection needle 8K are used as examples of connection targets to which the syringe 5K is connected.

For the connection in the luer-slip style, the syringe 5K to which the connector 1K is not attached is used, as shown in FIG. 33. As to the syringe 5K, the user may use a syringe to which no connector is originally attached, or alternatively obtain a syringe with the connector 1K attached and use this after detaching the connector 1K therefrom. The connector 1K can be readily detached by releasing the coupling of the interlocking tabs 11m and 12m.

In the connection in the luer-slip style, the luer part 51K of the syringe 5K is simply inserted into a port of a connection-target medical instrument. For example, the connection of the syringe 5K to the coinfusion port 7K is completed simply by inserting the luer part 51K of the syringe 5K into a valve plug (not shown) provided in a cover body 71K. Herewith, the interior of the syringe 5K and the interior of the tubes 72K and 73K of the coinfusion port 7K are communicated to each other.

The valve plug of the coinfusion port 7K is an elastic thin film, and a slit to receive the luer part 51K is formed in a part of the valve plug. Since such matters are public knowledge, the descriptions are omitted here.

Next, for connecting the syringe 5K and the injection needle 8K to each other, a needle hub 82K of the injection needle 8K is mounted on the luer part 51K of the syringe 5K. The syringe 5K and the injection needle 8K are connected to each other when an internal peripheral surface 82f of the needle hub 82K becomes tightly attached to the external peripheral surface 51f of the luer part 51K. Although no graphic representation is given, the needle tube 81K juts out also inside the needle hub 82K, and the jutted part is inserted into an inner hole of the luer part 51K when the syringe 5K and the injection needle 8K are connected to each other. The needle hub 82K and the inner hole of the luer part 51K are tightly fitted to each other while the injection needle 8K being connected to the syringe 5K. That is, the needle hub 81K and the inner hole are designed so that the liquid medication will not leak out therefrom or bacteria will not enter therefrom.

The luer-slip connection of the syringe 5K and another medical instrument has been described by presenting two examples above. The syringe 5K of FIG. 33 does not have the connector 1K attached thereto, allowing for quick luer-slip connection.

Although there are various medical instruments can be connected to the syringe 5K in the luer-slip style besides the above two examples, the connection operations for those instruments are the same as above.

Advantages of Connector 1K and Syringe 5K Having Connector 1K Attached Thereto

As has been described above and also shown in FIG. 31, the connector 1K of Embodiment 14 is composed of the split frames 11K and 12K and the coupling portion 13K, and allows for easy attachment to the syringe 5K by the coupling operation of the two split frames 11K and 12K as well as easy detachment from the syringe 5K by releasing the interlocking tabs 11m and 12m and opening the split frames 11K and 12K. On the other hand, unless the interlocking tabs 11m and 12m are released, an incident in which the split frames 11K and 12K open up during the use of the syringe 5K or the like is avoided.

Thus, since the user is able to attach and detach the connector 1K to/from the syringe 5K as the need arises, the connector 1K has advantageous effects of (1) reducing the cost burden on the user, (2) not causing hindrance to the work performance when the syringe 5K is used, and (3) enabling connection of the syringe 5K to the port of another instrument in either the luer-slip or luer-lock style. The syringe 5K having the connector 1K attached thereto also exhibits these advantages.

When connecting the injection needle 8K to the syringe 5K, the user can use the syringe 5K from which the connector 1K has been detached, as shown in FIG. 33. Thus, the syringe 5K is also effective in preventing the user from mistakenly pricking himself/herself.

Note that the connector 1K does not have to be provided with every syringe 5K when supplied to the user, and may be singularly provided to the user instead. In such a case, the user may attach/detach the connector 1K to/from the syringe 5K according to need.

If using the syringe 5K having the connector 1K attached thereto for treatment and testing in the medical practices, the user is able to select whether to attach or detach the connector 1K according to the connection style of the syringe to the port. Thus, using the syringe 5K with the connector 1K attached thereto achieves high efficiency in the medical practices.

15. Embodiment 15

Figure 34:
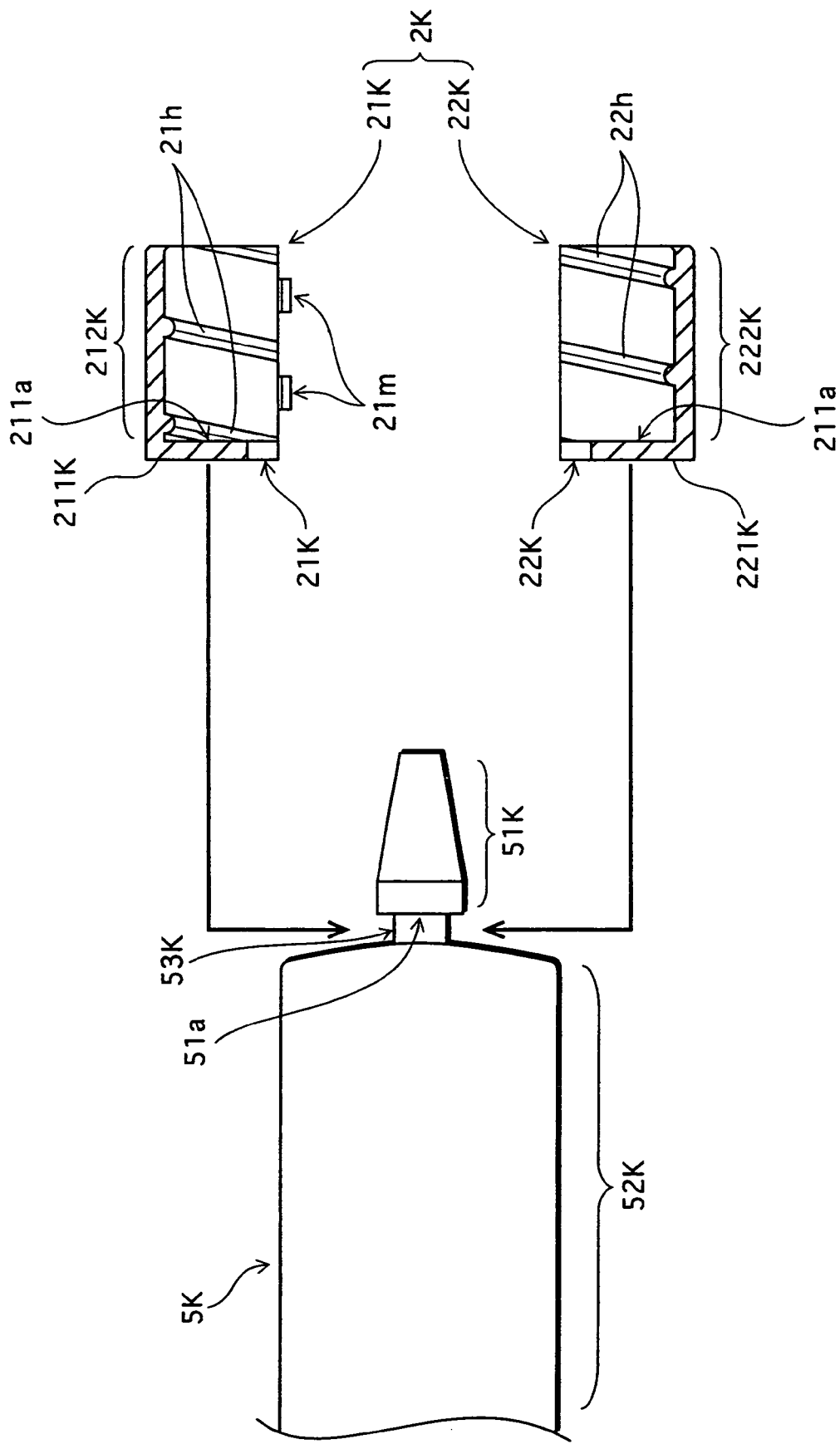
FIG. 34 is a perspective view showing a relation between a connector 2 of Embodiment 15 and the syringe 5.

A connector 2 of Embodiment 15 is described with the aid of FIG. 34.

The connector 2K is composed of split frames 21K and 22K as shown in FIG. 34, and differs from the connector 1K in that these split frames 21K and 22K are separated from each other. That is, the connector 2K can be said to be the connector 1K of Embodiment 14 from which the coupling portion 13K is removed. Note however that the connector 2 has additional tabs 11m and 12m formed on the split frames 21K and 22K at the locations corresponding to where the coupling portion 13K is attached.

Since other components of the connector 2K are the same as those of the connector 1K, the descriptions are omitted here.

Attachment of the connector 2K to the syringe 5K is achieved by setting the neck portion 53K of the syringe 5 in the cutouts 21h and 22h while the split frames 21K and 22K are separated from each other, and then interlocking the tabs 11m of the split frame 21K and the tabs 12m of the split frame 22K. Here, the relationships of the inner diameter of the hole formed by the cutouts 21h and 22h with the maximum outer diameter of the luer part 51K of the syringe 5K, and with the outer diameter of the neck portion 53K are the same as those of connector 1K of Embodiment 14 above.

The connector 2K is easily detached from the syringe 5K by doing the reverse of the above procedure, i.e. releasing the interlocking tabs 11m and 12m. Accordingly, also when using the connector 2K according to the present embodiment, the user is able to easily attach and detach the connector 2K to/from the syringe 5K as the need arises.

As a result, the connector 2K of Embodiment 15 also has advantageous effects of (1) reducing the cost burden on the user, (2) not causing hindrance to the work performance when the syringe 5K is used, and (3) enabling connection of the syringe 5K to the port of another instrument in either the luer-slip or luer-lock style.

16. Embodiment 16

A connector 3K of Embodiment 16 is described next with the aid of FIG. 35.

Figure 35:
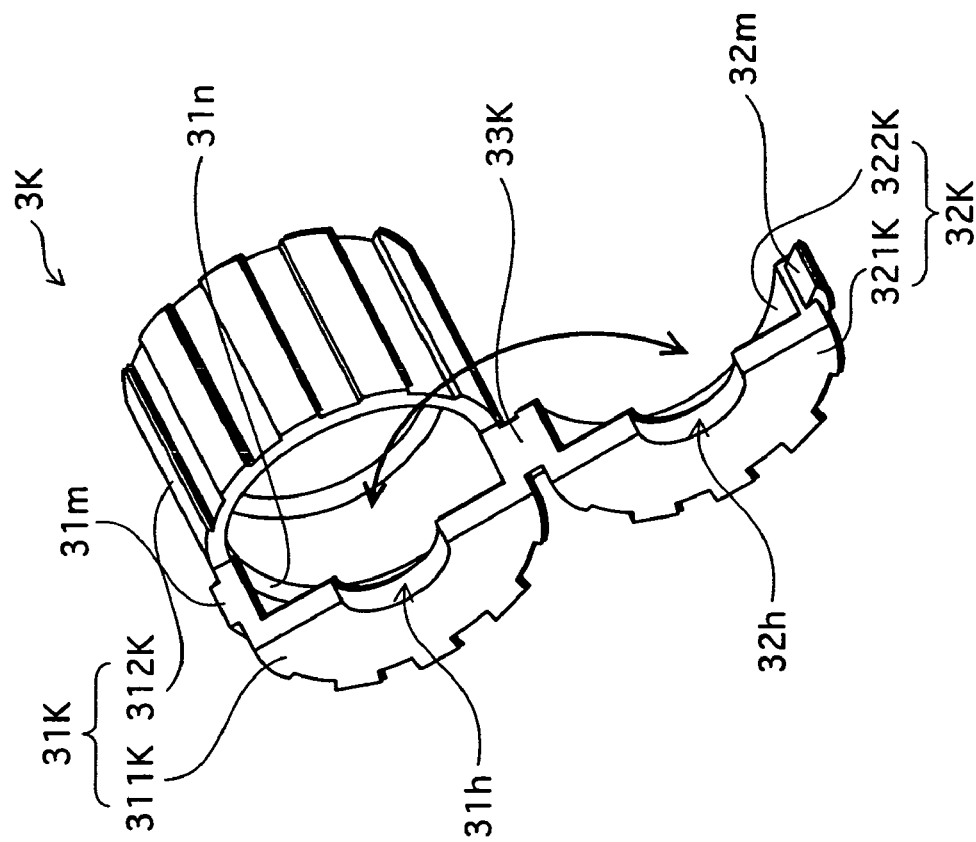
FIG. 35 is a perspective view showing a shape of a connector 3 of Embodiment 16.

The connector 3K is characterized by the split balance of split frames 31K and 32K different from that of split frames 11K and 12K of the connector 1K, as shown in FIG. 35. That is, while the split frames 11K and 12K of the connector 1K have a shape as if they were formed by halving, along the axis, a hollow cylinder with a bottom, the split frame 32K of the connector 3K according to the present embodiment has a shape as if it was formed by halving only the bottom face and the vicinity thereof of a hollow cylinder with a bottom.

The opening and closing of the connector 3K is basically the same as that of the connector 1K shown in FIG. 31.

Besides the advantageous effects of the connector 1K, the connector 3K has an additional advantage of having a cylindrical part which exhibits higher stiffness when the connector 3K is being screwed on another medical instrument (e.g. the extension tube 6K of FIG. 32), as compared to that of the connector 1K. That is, when a male screw 31n of the connector 3K is screwed into the female screw of the medical instrument to thereby join the connector 3K with the medical instrument, the cylindrical part of the connector 3K receives a force also in the outer radial direction. At this point, the connector 3K whose cylindrical part is not split has an advantage in exhibiting higher stiffness in the radial direction than the connector 1K whose cylindrical part is split.

This means that the connector 3K enables to set the syringe more firmly on the port of another medical instrument.

Additional Particulars Regarding Embodiments 14 through 16

In Embodiments 14 to 16 above, the features, functions and effects of the present invention are described by taking as examples three kinds of connectors 1K, 2K and 3K, however, the present invention is not limited to those.

Although, in Embodiment 14 above, a prefilled syringe filled with liquid medication in advance is used as an example of the syringe, the above-mentioned functions and effects remain the same even if a syringe of a different type is used.

In Embodiments 14 to 16, the connector 1K, 2K or 3K is connected to the syringe 5K by using the neck portion 53K formed on the base side of the luer part 51K of the syringe 5K. However, it is not necessary that the neck portion 53K is formed on the base side of the luer part 51K. For example, similar functions and effects to the above can be achieved by providing a narrowed part (which corresponds to the neck portion) on a part of the external peripheral surface of the syringe body 52K and forming a connector to correspond to the narrowed part.

17. Embodiment 17

FIGS. 36A, 36B, 36C and 36D illustrate a structure of a syringe of Embodiment 17.

A syringe 100L is a prefilled syringe filled with liquid medication 110L in advance, and allows for speedy insertion and removal into/out of either the luer-lock coinfusion port or the luer-slip coinfusion port.

Regarding the syringe 100, as shown in FIG. 36A, a cylindrical syringe portion 120L is filled with the liquid medication 110L and subsequently sealed by a plunger portion 150L, and a lock part 130L (which is an example of a connection supporting member) is freely rotatably coupled to one end of the syringe portion 120L by means of a coupling pin 160L (which is an example of a pin).

In the syringe part 120L, a cylindrical luer part 140L extends from one end (hereinafter referred to as "the first end") of a cylindrical syringe body 121L, and a flange 121a is provided at the opposite end to the first end (hereinafter referred to as "the second end").

The luer part 140L is cylindrical, and may be composed of: a $1^{st}$ luer portion 144L with a diameter d1 on the base side; and a tapered $2^{nd}$ luer portion 141L located on the tip side of the luer part 140L and having a tip-end diameter d2 and a rear-end diameter d3. With this arrangement, d3>d2 and d3>d1.

The lock part 130L is made of a resin material, and is a cylindrical nut with a bottom for engaging the syringe 100L and a connection-target instrument. A through hole 134L of a diameter d4 is provided on the bottom face of the lock part 130L, and through holes 132a and 132b with rectangular openings are provided on the lateral side of the cylindrical body.

Note that d4 is larger than d3 to enable the $2^{nd}$ luer portion 141L to pass through the through hole 134L.

The coupling pin 160L is a substantially U-shaped pin for engaging the lock part 130L and the luer part 140L, and has a function of engaging with the $1^{st}$ luer portion 144L while penetrating through the hull of the lock part 130L to be thereby fitted with the lock part 130L.

To be more specific, as shown in FIG. 36D which is a cutaway view of the coupling pin 160L fitted with the lock part 130L and cut parallel to the main surface thereof, the coupling pin 160L is a substantially U-shaped pin having two symmetric extending portions 163L extending from a rectangular fuse portion 161L. Stepped portions 162L, which abut against the lock part 130L when inserted thereinto, are provided at the base of the extending portions 163L, and a projecting portion 163a is provided on the outer side of each extending portion 163L, towards the tip end thereof.

Provided in the center of the groove 164L formed between these two extending portions 163L is a concave portion 165L to which the 1st luer portion 144L is fitted.

There is no problem whether the lock part 130L and coupling pin 160L are detached or attached from/to the syringe 100L when the syringe 100L is delivered to a medical practice site. Here, for convenience of explanation, the syringe 100L is used from which the lock part 130L and coupling pin 160L have been detached at the time of delivery.

The following explains how to use the syringe 100L.

Connection with Luer-Lock Coinfusion Port

When a coinfusion port to which the syringe 100L is to be connected is a luer-lock coinfusion port, a person (hereinafter, the "operator") inserts the luer part 140L into the through hole 134L of the lock part 130L, as shown in FIG. 36A. Subsequently, the operator inserts the coupling pin 160L into the through holes 132a and 132b of the lock part 130L as shown in FIG. 36B, and pushes the coupling pin 160L thereinto until the edges of the stepped portions 162L of the lock part 130L make contacts with edges 162a of both sides of the through hole 132a, as shown in FIGS. 37A to 37F.

At this point, the projecting portions 163a of the coupling pin 160L go over contact points 162b an both sides of the through hole 132b and thereby prohibit the coupling pins 160L from shifting in the reverse direction of the insertion. At the same time, the $1^{st}$ luer portion 144L is fitted into the concave portion 165L.

Here, the 1st luer portion 144L and the lock part 130L are engaged with each other to be positioned concentrically.

In addition, since the contact faces of the 1st luer portion 144L and the concave portion 165L of the coupling pin 160L slip against each other in the circumferential direction, the 1st luer portion 144L and the lock part 130L rotate relatively to each other around the central axis of the 1st luer portion 144L.

As to the above-mentioned coinfusion port 200L which is a luer-lock coinfusion port, on the lateral side of a port body 201L functioning as a transfusion line or a similar flow path, a rubber valve 204 having a hole 204a is held in place by being covered with a cylindrical cover body 202L. A screw thread is cut on the external periphery of the cover body. 202L to thereby form a thread groove 203L.

When connecting the syringe 100L to the coinfusion port 200L, the operator rotates the lock part 130L and screws the lock part 130L onto the thread groove 203L while inserting the 2nd luer portion 141L of the syringe 100L into the hole 204a of the coinfusion port 200L, as shown in FIG. 36C, and whereby the syringe 100L is securely connected to the coinfusion port 200L.

Figure 38:
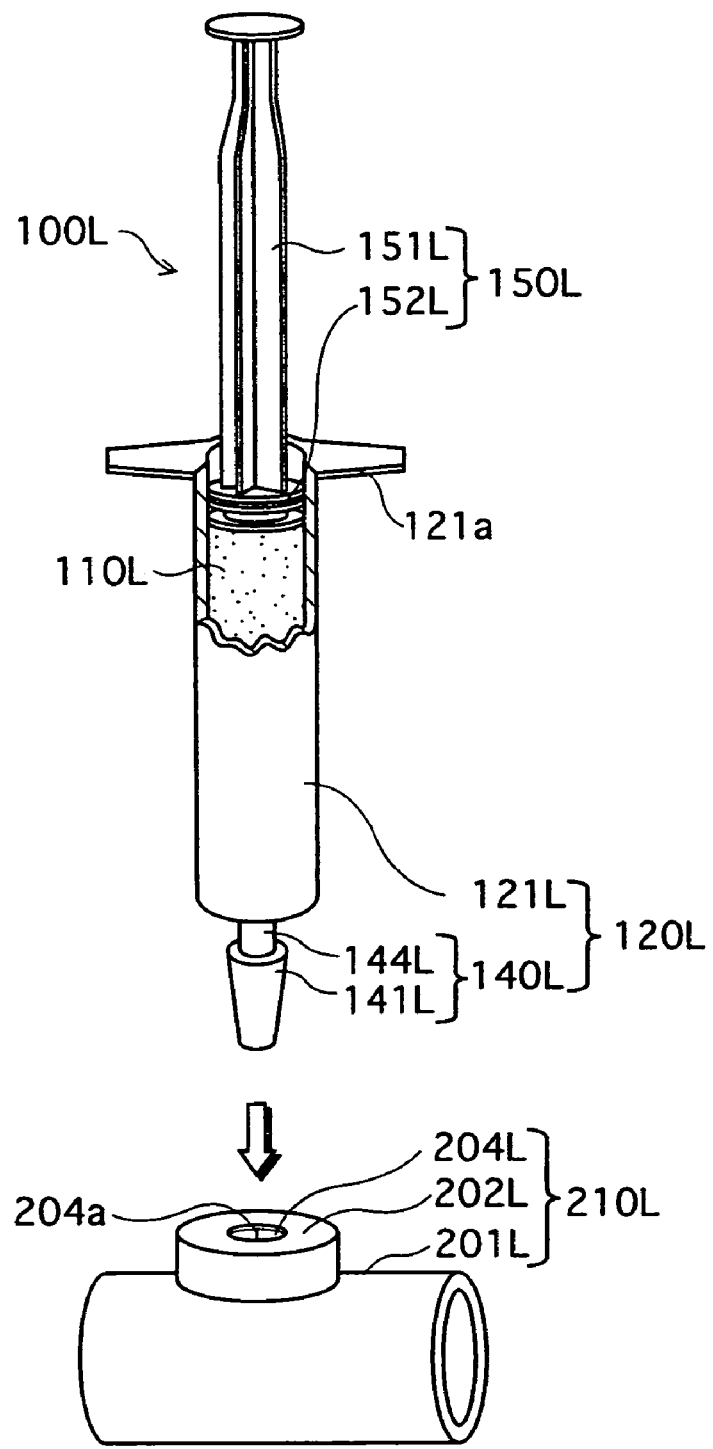
FIG. 38 shows the way of the syringe of Embodiment 17 being inserted into a coinfusion port in the luer-slip style.

When connecting the syringe 100L to the luer-slip coinfusion port 210L, the operator is able to rapidly connect the syringe 100L, to which the lock part 130L is not attached, to a coinfusion port 210L by inserting the 2nd luer portion 141L into the hole 204a of the coinfusion port 210L, as shown in FIG. 38.

Thus, since the syringe 100L of the present embodiment allows for easy attachment and detachment of the lock part 130L by insertion and pullout of the coupling pin 160L, the syringe 100L is smoothly connected to a luer-slip style instrument by detaching the lock part 130L from the syringe 100L, similarly to the case of a conventional luer-slip syringe.

When the syringe 100L is connected to an instrument in the luer-lock style, secure connection can be established by attaching the lock part 130L to the syringe 100L, similarly to the case of a conventional luer-lock syringe.

In Embodiment 17, the $1^{st}$ luer portion 144L and the lock part 130L are designed to rotate relatively to each other, however, the present invention is not limited to this. For example, the following structure may be employed: a spline parallel to the syringe axis direction (hereinafter, "the $1^{st}$ spline) is provided on the outer surface of the $1^{st}$ luer portion 144L of the syringe 100L, and another spline (hereinafter, "the $2^{nd}$ spline") corresponding to the $1^{st}$ spline is provided on the concave portion 165L of the coupling pin 160L. Herewith, when the $1^{st}$ luer portion 144L is fitted into the concave portion 165L, the $1^{st}$ and $2^{nd}$ splines are fitted with each other so that the $1^{st}$ luer portion 144L is positionally fixed in relation to the concave portion 165L.

In this case, although the syringe 100L and the lock part 130L cannot rotate relative to each other, the above-mentioned nut can be screwed by rotating the entire syringe 100L while inserting the $2^{nd}$ luer Portion 141L into a target location since the lock part 130L and the $1^{st}$ luer portion 144L are in a concentric configuration.

Note also that, although in Embodiment 17 the lock part 130L of the syringe 100L is a nut that engages with an instrument such as a coinfusion port, this is merely an example and the part does not have to be a nut.

Figure 39:
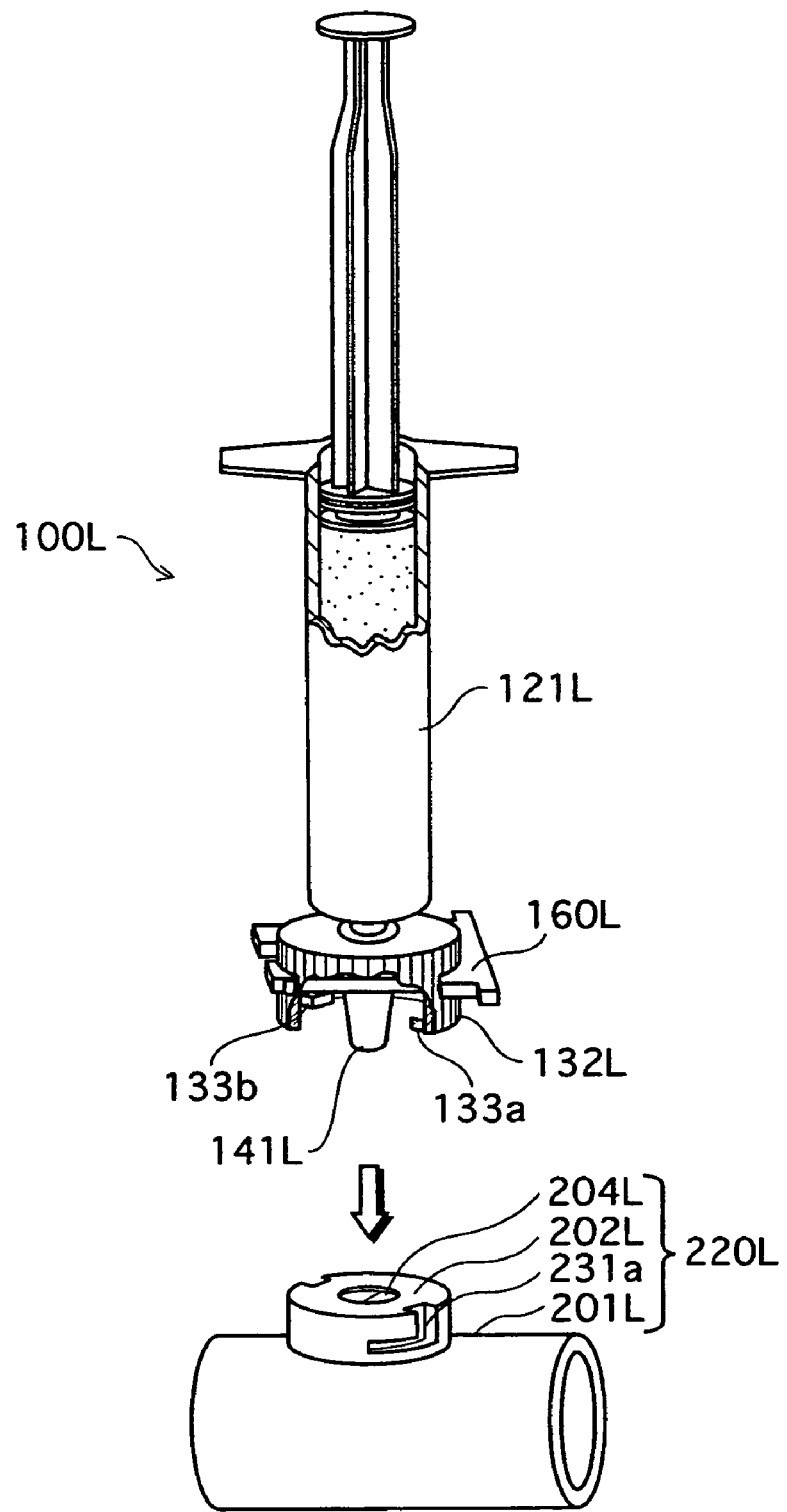
FIG. 39 shows an example of realizing a lock mechanism of a syringe of Embodiment 18, using another structure other than a screw nut.

For instance, as in Embodiment 18 shown in FIG. 39, a lock part 132L having claw portions 133a and 133b may be used instead of the lock part 130L having a thread.

In this case, the change in the locking mechanism of the syringe necessitates a change in the structure of the engaging portion of the luer-lock coinfusion port. A coinfusion port 220L having two L-shaped grooves 231a is one example of such a structural change.

Note that, although the coupling pin 160L is substantially U-shaped, this is merely an example. If a pin fulfills a similar function, i.e. enabling the lock part 130L and the luer part 140L to be fixed at a determined position, the pin may take any shape.

Figure 40:
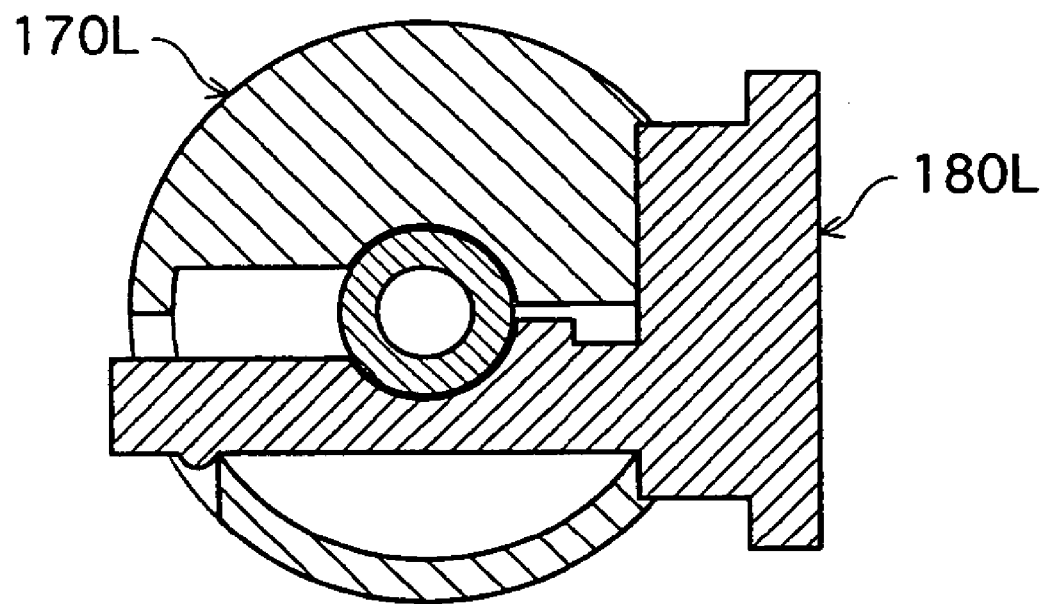
FIG. 40 shows an example where the lock part and syringe are engaged with each other using a coupling pin of Embodiment 19, the shape of which is different from that of the coupling pin of Embodiment 17.
Figures 41A, 41B, 41C:
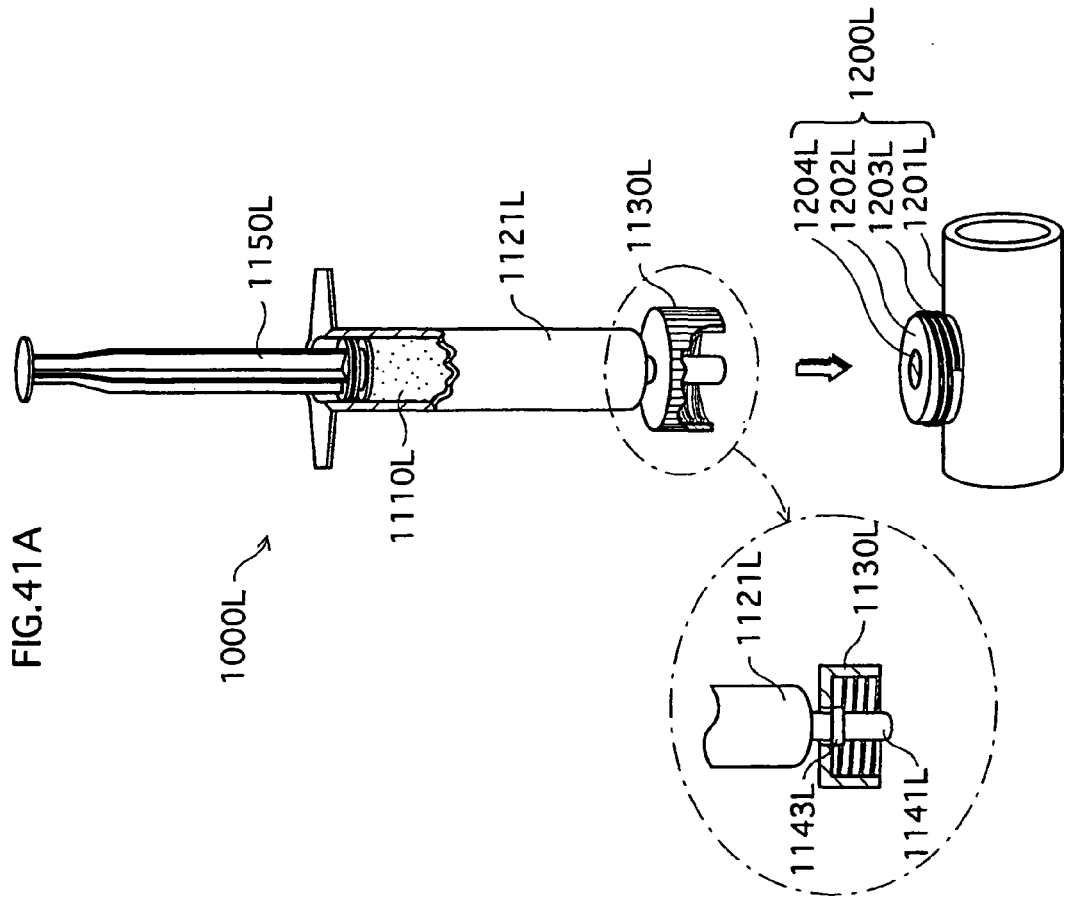
FIG. 41 illustrates usage of a conventional luer-lock syringe.
Figure 42:
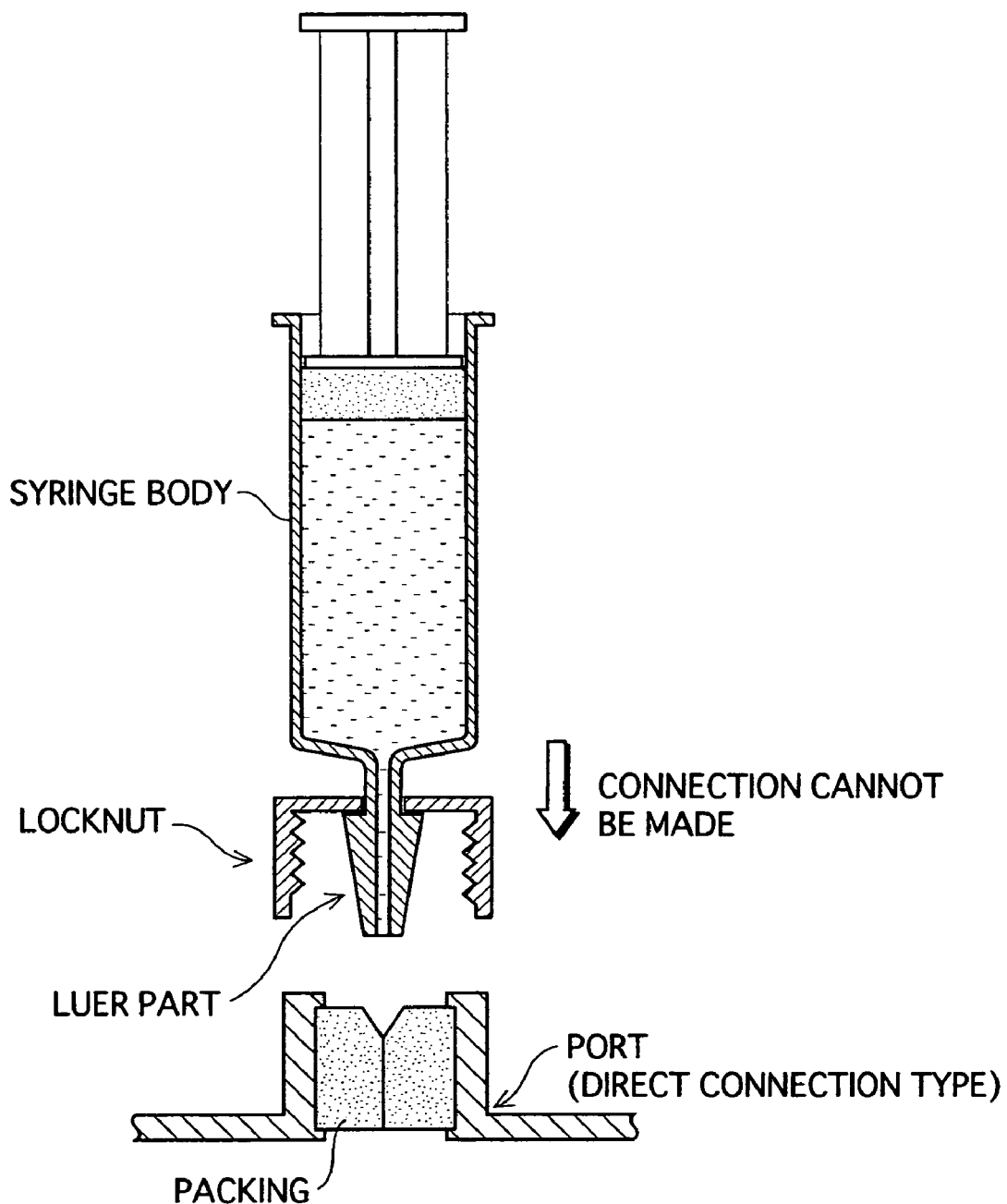
FIG. 42 shows a structure of a conventional locknut and a prefilled syringe.

For example, a coupling pin 180 of Embodiment 19 shown in FIG. 40 (corresponding to FIG. 36D) may be used. Here, a lock part 170L has been formed by partially revising the cross-sectional shape of the lock part 130L so that the lock part 170L serves the function fulfilled by one of the two extending portions 163L of the coupling pin 160L, and the coupling pin 180L has only one extending portion 163L.

INDUSTRIAL APPLICABILITY

The connector-attached syringes, connectors used for syringes, and syringes of the present invention can be used to apply liquid medication to patients and collect blood in medical practices.

The connector-attached syringes and connectors of the present invention are adaptable for both luer-slip and luer-lock style ports, providing a cost reduction to the users.

The present invention is applicable to manufacturing medical syringes used in medical practices in which various types of connection ports are used.

The invention claimed is:

1. A system for connecting a a syringe unit to a port, said system comprising:
a syringe unit having a syringe body and a luer part disposed at a first axial position, the syringe body having a plunger and a first engaging portion disposed on an outer peripheral surface thereof, the first engaging portion being separated from the luer part; and
a connector configured to be externally disposed at the luer part and extending from the syringe unit, and including a second engaging portion configured to engage the first engaging portion disposed on the outer peripheral surface of the syringe body, such that the engagement of the second engaging portion with the first engaging portion substantially prevents movement of the connector relative to the syringe body, when engaging the first engaging portion, the second engaging portion is disposed in a second axial position on the syringe body such that the second axial position is not disposed along the same radial plane as the first axial position,
wherein engagement of the first and second engaging portions is released when an external force is applied, according to a predetermined operation, to one of the connector and the syringe unit in a direction different from a syringe axial direction, and
wherein the first and second engaging portions are configured and arranged to enable the luer part to be removably attached to the connector so as to enable selective discharge of medication through the port.

2. The system of claim 1, wherein
a body of the connector is tubular,
the second engaging portion is on an extension portion which extends from the body of the connector, and
the first and second engaging portions are engaged with each other by inserting the luer part into the body of the connector and elastically contacting the extension portion with the outer peripheral surface of the syringe body, and the engagement is released by detaching the second engaging portion from the outer peripheral surface of the syringe body.

3. A connector for fixedly holding a syringe unit on a port and being disposed at an outer surface of a luer part extending from the syringe unit which includes a syringe body and a plunger, comprising:
a tubular body portion with a base, the base having first thread members thereon; and
a constraint portion having second thread members, the constraint portion encircling a periphery of the body portion and being configured to exert constraint effects on the base by shifting in an axial direction of the body portion via engagement of the first and second thread members, wherein
the base of the body portion includes a plurality of swingable petal-shaped members, the petal-shaped members being opposed to each other so as to form a space therebetween,
in a first state, the petal-shaped members are closed so as to narrow the space formed therebetween due to the constraint effects exerted on the base, and the luer part is engaged with the petal-shaped members in a syringe axial direction such that movement of the connector relative to the syringe body is substantially prevented, and
in a second state, the petal-shaped members are open due to the base being free from the constraint effects, and the luer part is freely insertable and removable into and from the connector via an open hole formed in a substantially central region of the base when the petal-shaped members are open, and wherein
the petal-shaped members are configured to enable the luer part to be removably attached to the connector so as to enable selective discharge of medication through the port.

4. The connector of claim 3, wherein
the constraint portion is a nut having the second thread members on an internal peripheral surface thereof,
the body portion is in a shape of a substantial cylinder, the first thread members, which correspond to the nut, being disposed on a section of an outer peripheral surface of the cylinder, the section being a range where the constraint portion is movable,
in the first state, part of the body portion corresponding to the section is closed, taking on a shape of a cylinder, and
in the second state, the part of the body portion is open, spreading like open tweezers towards the base in the axial direction.

5. A connector for fixedly holding a syringe unit on a port and being disposed at a luer part extending from the syringe unit which includes a syringe body and a plunger, comprising:
a plurality of components, which individually have interlocking members for coupling mechanisms, the interlocking members interlocking with each other to thereby couple the components, making the connector in a shape of a tube having a base and screw portions, wherein
when made in the shape of the tube, the connector engages with the luer part, such that movement of the connector relative to the syringe body is substantially prevented, and the connector is configured to engage and axially move the port via the screw portions so as to connect the syringe unit to the port,
when the coupling of the components is released, the luer part is freely insertable and removable into and from the connector, and wherein
the components are configured to enable the luer part to be removably attached to the connector so as to enable selective discharge of medication through the port.

6. The connector of claim 5, wherein
the components are symmetrical to each other and have end portions facing to each other, a cutout is disposed on each of the end portions, and
the cutouts face to each other to form an engaging hole, which engages with an engaging portion of the luer part.

7. The connector of claim 5, wherein
at least one of the coupling mechanisms includes a locking tab and a locked tab which interlock with each other when the components are coupled.

8. The system of claim 1, wherein the connector is configured so as to connect the luer to the port.

9. The connector of claim 3, wherein the connector is configured so as to connect the luer to the port.

10. The connector of claim 5, wherein the connector is configured so as to connect the luer to the port.

11. A connector for connecting a syringe unit to a port and being externally disposed at a luer part extending from the syringe unit, the luer part being disposed at a first axial position, the syringe unit including a syringe body and a plunger, the syringe body having a first engaging portion disposed on an outer peripheral surface thereof, the engaging portion being separated from the luer part, the connector comprising:
a second engaging portion configured to engage the first engaging portion disposed on the outer peripheral surface of the syringe body, such that the engagement of the second engaging portion with the first engaging portion substantially prevents movement of the connector relative to the syringe body, when engaging the first engaging portion, the second engaging portion is disposed in a second axial position on the syringe body such that the second axial position is not disposed along the same radial plane as the first axial position, wherein engagement of the first and second engaging portions is released when an external force is applied, according to a predetermined operation, to one of the connector and the syringe unit in a direction different from a syringe axial direction, wherein the first and second engaging portions are configured and arranged to enable the luer part to be removably attached to the connector so as to enable selective discharge of medication through the port, and wherein a body of the connector is tubular, the second engaging portion is on an extension portion which extends from the body of the connector, and the first and second engaging portions are engaged with each other by inserting the luer part into the body of the connector and elastically contacting the extension portion with the outer peripheral surface of the syringe body, and the engagement is released by detaching the second engaging portion from the outer peripheral surface of the syringe body.

* * * * *